US006969595B2

(12) United States Patent
Brzostowicz et al.

(10) Patent No.: US 6,969,595 B2
(45) Date of Patent: Nov. 29, 2005

(54) CAROTENOID PRODUCTION FROM A SINGLE CARBON SUBSTRATE

(75) Inventors: Patricia C. Brzostowicz, West Chester, PA (US); Qiong Cheng, Wilmington, DE (US); Deana DiCosimo, Rockland, DE (US); Mattheos Koffas, Wilmington, DE (US); Edward S. Miller, Wilmington, DE (US); James M. Odom, Kennett Square, PA (US); Stephen K. Picataggio, Landenberg, PA (US); Pierre E. Rouviere, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 728 days.

(21) Appl. No.: 09/941,947

(22) Filed: Aug. 29, 2001

(65) Prior Publication Data

US 2003/0003528 A1 Jan. 2, 2003

Related U.S. Application Data

(60) Provisional application No. 60/229,907, filed on Sep. 1, 2000, and provisional application No. 60/229,858, filed on Sep. 1, 2000.

(51) Int. Cl.$^7$ .............................................. G01N 33/72
(52) U.S. Cl. ..................... 435/67; 435/252.3; 536/23.2; 536/23.7
(58) Field of Search ....................... 435/67, 183, 252.3; 536/23.2, 23.7

(56) References Cited

U.S. PATENT DOCUMENTS

| | | | |
|---|---|---|---|
| 5,182,208 A | 1/1993 | Johnson et al. | 435/255.1 |
| 5,429,929 A | 7/1995 | Latov et al. | 435/7.9 |
| 5,429,939 A | 7/1995 | Misawa et al. | |
| 5,466,599 A | 11/1995 | Jacobson et al. | 435/255.1 |
| 5,530,188 A | 6/1996 | Ausich et al. | 860/298 |
| 5,530,189 A | 6/1996 | Ausich et al. | 800/298 |
| 5,545,816 A | 8/1996 | Ausich et al. | 800/298 |
| 5,656,472 A | 8/1997 | Ausich et al. | 435/193 |
| 5,691,190 A | 11/1997 | Girard et al. | 435/255.1 |
| 5,750,821 A | 5/1998 | Inomata et al. | 585/312 |
| 5,972,642 A | 10/1999 | Flen.o slashed. et al. | 435/67 |
| 6,015,684 A | 1/2000 | Jacobson et al. | 435/67 |
| 6,124,113 A | 9/2000 | Hohmann et al. | 435/67 |

FOREIGN PATENT DOCUMENTS

| | | |
|---|---|---|
| EP | 0747483 A2 | 12/1996 |
| EP | 0872554 A2 | 10/1998 |
| WO | WO 97 23633 A1 | 7/1997 |
| WO | WO 9907867 A1 | 2/1999 |
| WO | WO 9961652 A1 | 12/1999 |
| WO | WO 2000007718 A1 | 2/2000 |
| WO | WO 01/66703 A1 | 9/2001 |
| WO | WO 0220733 A2 | 3/2002 |
| WO | WO 02/41833 A2 | 5/2002 |
| WO | WO 02079395 A2 | 10/2002 |

OTHER PUBLICATIONS

Hundle et al., Functional Assignment of *Erwinia herbicola* Eh010 Carotenoid Genes Expressed in *Escherichia coli*, Molecular and General Genetics, Springer Verlag, Berlin, DE, vol. 245, 1994, pp. 406–416, XP002947192.

Pasamontes et al., Isolation and characterization of the carotenoid biosynthesis genes of *Flavobacterium* sp. Strain R1534, Gene: An International Journal on Genes and Genomes, Elsevier Science Publishers, Braking, GB, vol. 185, No. 1, Jan. 31, 1997, pp. 35–41, XP004093151.

Harker et al., Biosynthesis of Ketocarotenoids in transgenic cyanobacteria expressing the algal gene for beta–C–4–oxygenase, crt0, FEBS Letters, Elsevier Science Publishers, Amsterdam, NL. Vol. 404, Mar. 1, 1997, pp. 129–134, XP002087149.

Fernandez–Gonzalez Blanca et al., A new type of asymmetrically acting beta–carotene ketolase is required for the synthesis of echinenone in the cyanobacterium *Synechocystis* sp. PCC 6803., Journal of Biological Chemistry vol. 272, No. 15, 1997, pp. 9728–9733, XP002222602.

Hirschberg, Production of high–value compounds: Carotenoids and vitamin E, Current Opinion in biotechnology, London GB, vol. 10, No. 2, Apr. 1999, pp. 186–191, XP002162837.

Misawa et al., Expression of an Wrwinia Phytoene Desaturase Gene not only confers Multiple Resistance to Herbicides Interfering with Carotenoid Biosynthesis but also alters Xanthophyll Metabolism in Transgenic Plants, Plant Journal, Blackwell Scientific Publications, Oxford, GB, vol. 6, No. 4, 1994, pp. 481–489, XP002012919.

Scolnik et al., A Table of Some Cloned Plant Genes Involved in Isoprenoid Biosynthesis, Plant Molecular Biology Reporter, New York, NY vol. 14, No. 4, Dec. 1996, pp. 305–319, XP000884796.

Bartley et al., Molecular Biology of Carotenoid Biosynthesis in Plants, Annual Review of Plant Physiology and Plant Molecular Biology, Annual Reviews Inc, vol. 45, 1994, pp. 287–301, XP000881128.

Rohmer, Isoprenoid Biosynthesis via the Mevalonate–Independent Route, A novel Target for Antibacterial Drugs?, Progress in Drug Research, Basel, vol. 50, 1998, pp. 135–154, XP000906878.

Hanson et al., Methanotrophic bacteria, Microbiological Reviews, American Societyfor Microbiology, Washington, D.C., vol. 60, No. 2, Jun. 1996, pp. 439–471.

Zhu Xufen et al., Geranylgeranyl pyrophosphate synthase encoded by the newly isolated gene GGPS6 from *Arabidopsis thaliana* is localized in mitochondria, Plant Molecular Biology, Nijhoff Publishers, Dordrecht, NL, vol. 35, No. 3, 1997, pp. 331–341, XP002153683.

(Continued)

Primary Examiner—Nashaat T. Nashed

(57) ABSTRACT

A method for the production of carotenoid compounds is disclosed. The method relies on the use of microorganisms which metabolize single carbon substrates for the production of carotenoid compounds in high yields.

22 Claims, 14 Drawing Sheets

OTHER PUBLICATIONS

Misawa et al., "Elucidation of the *Erwinia uredovora* Carenoid Biosynthetic Pathway by Functional Analysis of Gene Products Expressed in *Escherichia coli*", Journal of Bacteriology, Washington, D.C., vol. 172, No. 12, Dec. 1990, pp. 6704–6712.

Armstrong, J. Bact. 176: pp. 4795–4802.

Armstrong, Annu. Rev. Microbiol. 51: 629–659, 1997.

Nelis and Leenheer, Appl. Bacteriol. 70:181–191, 1991.

Farmer, W. R. and J. C. Liao, 2001, Biotechnol. Prog. 17: 57–61.

Wang, C. et al., 2000 Biotechnol. Prog. 16: 922–926.

Misawa, N. and H. Shimada, 1998, J. Biotechnol. 59: 169–181.

Shimada, H. et al., 1998, Appl. Environm. Microbiol. 64:2676–2680.

Miura, Y. et al., 1998. Appl. Environm. Microbiol. 64: 1226–1229.

Albrecht, M. et al., 1999, Biotechnol. Lett. 21: 791–795.

Lidstrom and Stirling (Annu. Rev. Microbiol. 44:27–58, 1990.

Murrell et al., Arch. Microbiol., 2000, 173(5–6), 325–332.

Grigoryan, E. A., Kinet. Catal., 1999, 40(3), 350–363.

Beschastnyi et al., Inst. Biochem. Physiol. Microor., Pushchino, Russia, Biokhimiya (Moscow) 1992, 57(8), pp. 1215–1221.

Shishkina et al., Inst. Bikhim. Fiziol. Mikroorg., Pushchino, Russia, Mlkrobiologiya, 1990, 59(4), 533–8.

Trotsenko et al., Studies on Phosphate metabolism in obligate methanotrophs, Fems Microbiology Reviews 87, 1990, pp. 267–272.

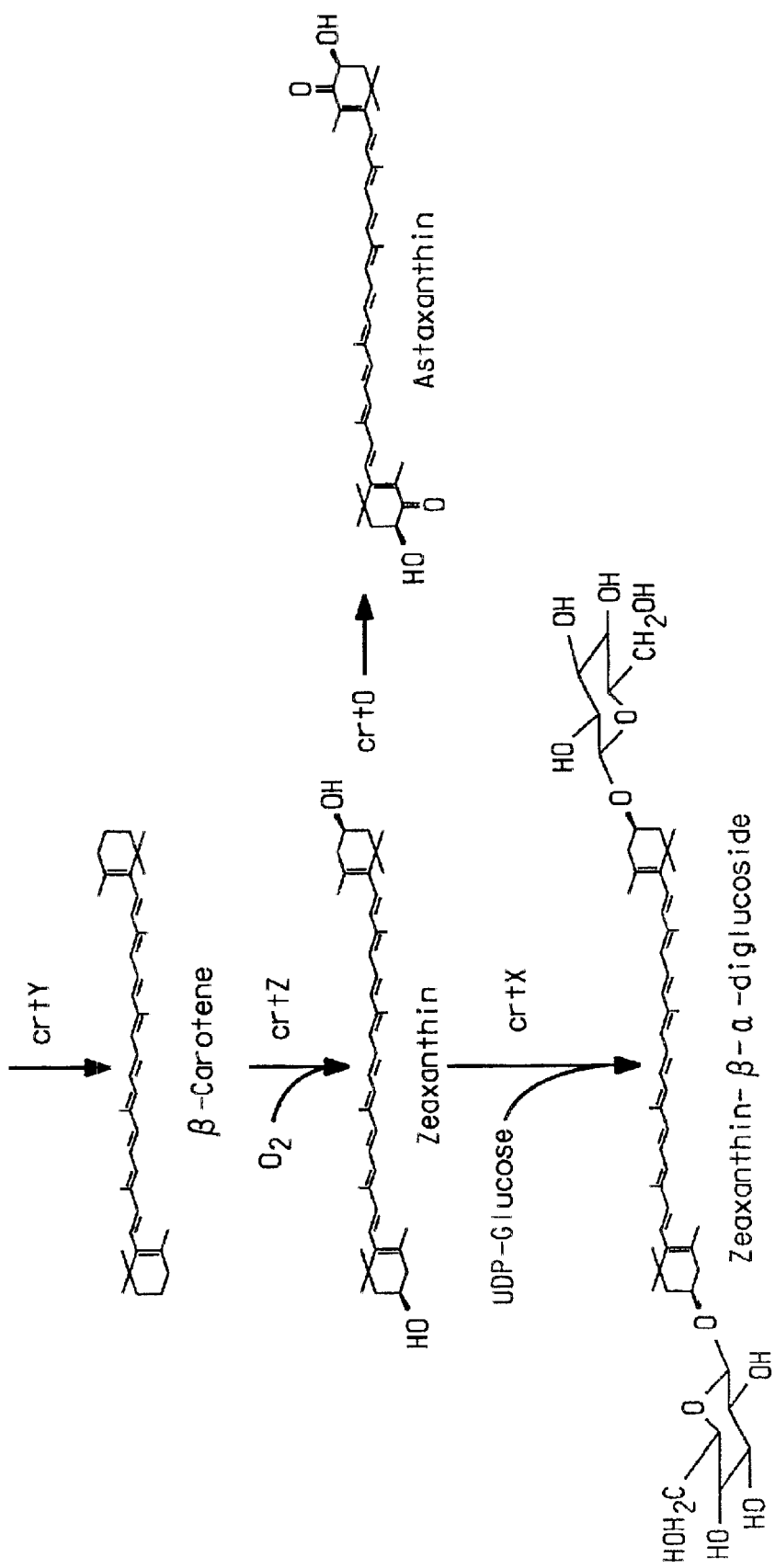

SEQUENCE LISTING

<160> NUMBER OF SEQ ID NOS: 60

<210> SEQ ID NO 1
<211> LENGTH: 1311
<212> TYPE: DNA
<213> ORGANISM: Methylomonas 16a

<400> SEQUENCE: 1

```
gatgtggtca catggcccta tcacttaacg gctgatattc gattttgtca ttggttttt      60
cttaacttta acttctacac gctcatgaac aaacctaaaa aagttgcaat actgacagca    120
ggcggcttgg cgccttgttt gaattccgca atcggtagtt tgatcgaacg ttataccgaa    180
atcgatccta gcatagaaat catttgctat cgcggcggtt ataaaggcct gttgctgggc    240
gattcttatc cagtaacggc cgaagtgcgt aaaaaggcgg tgttctgca acgttttggc     300
ggttctgtga tcggcaacag ccgcgtcaaa ttgaccaatg tcaaagactg cgtgaaacgc    360
ggtttggtca agagggtga agatccgcaa aaagtcgcgg ctgatcaatt ggttaaggat     420
ggtgtcgata ttctgcacac catcggcggc gatgatacca atacggcagc agcggatttg    480
gcagcattcc tggccagaaa taattacgga ctgaccgtca ttggtttacc taaaaccgtc    540
gataacgacg tatttccgat caagcaatca ctaggtgctt ggactgccgc cgagcaaggc    600
gcgcgttatt tcatgaacgt ggtggccgaa acaacgcca acccacgcat gctgatcgta     660
cacgaagtga tgggccgtaa ctgcggctgg ctgaccgctg caaccgcgca ggaatatcgc    720
aaattactgg accgtgccga gtggttgccg gaattgggtt tgactcgtga atcttatgaa    780
gtgcacgcgg tattcgttcc ggaaatggcg atcgacctgg aagccgaagc caagcgcctg    840
cgcgaagtga tggacaaagt cgattgcgtc aacatcttcg tttccgaagg tgccggcgtc    900
gaagctatcg tcgcggaaat gcaggccaaa ggccaggaag tgccgcgcga tgcgttcggc    960
cacatcaaac tggatgcggt caaccctggt aaatggttcg gcgagcaatt cgcgcagatg   1020
ataggcgcgg aaaaaccct ggtacaaaaa tcgggatact tcgcccgtgc ttctgcttcc    1080
aacgttgacg acatgcgttt gatcaaatcg tgcgccgact tggcggtcga gtgcgcgttc   1140
cgccgcgagt ctggcgtgat cggtcacgac gaagacaacg gcaacgtgtt gcgtgcgatc   1200
gagtttccgc gcatcaaggg cggcaaaccg ttcaatatcg acaccgactg gttcaatagc   1260
atgttgagcg aaatcggcca gcctaaaggc ggtaaagtcg aagtcagcca c            1311
```

<210> SEQ ID NO 2
<211> LENGTH: 437
<212> TYPE: PRT
<213> ORGANISM: Methylomonas 16a

<400> SEQUENCE: 2

```
Asp Val Val Thr Trp Pro Tyr His Leu Thr Ala Asp Ile Arg Phe Cys
 1               5                  10                  15

His Trp Phe Phe Leu Asn Phe Asn Phe Tyr Thr Leu Met Asn Lys Pro
            20                  25                  30

Lys Lys Val Ala Ile Leu Thr Ala Gly Gly Leu Ala Pro Cys Leu Asn
        35                  40                  45

Ser Ala Ile Gly Ser Leu Ile Glu Arg Tyr Thr Glu Ile Asp Pro Ser
    50                  55                  60

Ile Glu Ile Ile Cys Tyr Arg Gly Gly Tyr Lys Gly Leu Leu Leu Gly
65                  70                  75                  80
```

-continued

```
Asp Ser Tyr Pro Val Thr Ala Glu Val Arg Lys Lys Ala Gly Val Leu
                 85                  90                  95
Gln Arg Phe Gly Gly Ser Val Ile Gly Asn Ser Arg Val Lys Leu Thr
            100                 105                 110
Asn Val Lys Asp Cys Val Lys Arg Gly Leu Val Lys Glu Gly Glu Asp
        115                 120                 125
Pro Gln Lys Val Ala Ala Asp Gln Leu Val Lys Asp Gly Val Asp Ile
    130                 135                 140
Leu His Thr Ile Gly Gly Asp Thr Asn Thr Ala Ala Asp Leu
145                 150                 155                 160
Ala Ala Phe Leu Ala Arg Asn Asn Tyr Gly Leu Thr Val Ile Gly Leu
                165                 170                 175
Pro Lys Thr Val Asp Asn Asp Val Phe Pro Ile Lys Gln Ser Leu Gly
            180                 185                 190
Ala Trp Thr Ala Ala Glu Gln Gly Ala Arg Tyr Phe Met Asn Val Val
        195                 200                 205
Ala Glu Asn Asn Ala Asn Pro Arg Met Leu Ile Val His Glu Val Met
    210                 215                 220
Gly Arg Asn Cys Gly Trp Leu Thr Ala Ala Thr Ala Gln Glu Tyr Arg
225                 230                 235                 240
Lys Leu Leu Asp Arg Ala Glu Trp Leu Pro Glu Leu Gly Leu Thr Arg
                245                 250                 255
Glu Ser Tyr Glu Val His Ala Val Phe Val Pro Glu Met Ala Ile Asp
            260                 265                 270
Leu Glu Ala Glu Ala Lys Arg Leu Arg Glu Val Met Asp Lys Val Asp
        275                 280                 285
Cys Val Asn Ile Phe Val Ser Glu Gly Ala Gly Val Glu Ala Ile Val
    290                 295                 300
Ala Glu Met Gln Ala Lys Gly Gln Glu Val Pro Arg Asp Ala Phe Gly
305                 310                 315                 320
His Ile Lys Leu Asp Ala Val Asn Pro Gly Lys Trp Phe Gly Glu Gln
                325                 330                 335
Phe Ala Gln Met Ile Gly Ala Glu Lys Thr Leu Val Gln Lys Ser Gly
            340                 345                 350
Tyr Phe Ala Arg Ala Ser Ala Asn Val Asp Asp Met Arg Leu Ile
        355                 360                 365
Lys Ser Cys Ala Asp Leu Ala Val Glu Cys Ala Phe Arg Arg Glu Ser
    370                 375                 380
Gly Val Ile Gly His Asp Glu Asp Asn Gly Asn Val Leu Arg Ala Ile
385                 390                 395                 400
Glu Phe Pro Arg Ile Lys Gly Gly Lys Pro Phe Asn Ile Asp Thr Asp
                405                 410                 415
Trp Phe Asn Ser Met Leu Ser Glu Ile Gly Gln Pro Lys Gly Gly Lys
            420                 425                 430
Val Glu Val Ser His
        435
```

<210> SEQ ID NO 3
<211> LENGTH: 636
<212> TYPE: DNA
<213> ORGANISM: Methylomonas 16a

<400> SEQUENCE: 3
gaaaatacta tgtccgtcac catcaaagaa gtcatgacca cctcgcccgt tatgccggtc    60

```
atggtcatca atcatctgga acatgccgtc cctctggctc gcgcgctagt cgacggtggc    120
ttgaaagttt tggagatcac attgcgcacg ccggtggcac tggaatgtat ccgacgtatc    180
aaagccgaag taccggacgc catcgtcggc gcgggcacca tcatcaaccc tcataccttg    240
tatcaagcga ttgacgccgg tgcggaattc atcgtcagcc ccggcatcac cgaaaatcta    300
ctcaacgaag cgctagcatc cggcgtgcct atcctgcccg gcgtcatcac acccagcgag    360
gtcatgcgtt tattggaaaa aggcatcaat gcgatgaaat tctttccggc tgaagccgcc    420
ggcggcatac cgatgctgaa atcccttggc ggccccttgc cgcaagtcac cttctgtccg    480
accggcggcg tcaatcccaa aaacgcgccc gaatatctgg cattgaaaaa tgtcgcctgc    540
gtcggcggct cctggatggc gccggccgat ctggtagatg ccgaagactg gcggaaatc     600 acgcggcggg cgagcgaggc cgcggcattg aaaaaa                              636
```

<210> SEQ ID NO 4
<211> LENGTH: 212
<212> TYPE: PRT
<213> ORGANISM: Methylomonas 16a

<400> SEQUENCE: 4

```
Glu Asn Thr Met Ser Val Thr Ile Lys Glu Val Met Thr Thr Ser Pro
1               5                   10                  15

Val Met Pro Val Met Val Ile Asn His Leu Glu His Ala Val Pro Leu
            20                  25                  30

Ala Arg Ala Leu Val Asp Gly Gly Leu Lys Val Leu Glu Ile Thr Leu
        35                  40                  45

Arg Thr Pro Val Ala Leu Glu Cys Ile Arg Arg Ile Lys Ala Glu Val
    50                  55                  60

Pro Asp Ala Ile Val Gly Ala Gly Thr Ile Ile Asn Pro His Thr Leu
65                  70                  75                  80

Tyr Gln Ala Ile Asp Ala Gly Ala Glu Phe Ile Val Ser Pro Gly Ile
                85                  90                  95

Thr Glu Asn Leu Leu Asn Glu Ala Leu Ala Ser Gly Val Pro Ile Leu
            100                 105                 110

Pro Gly Val Ile Thr Pro Ser Glu Val Met Arg Leu Leu Glu Lys Gly
        115                 120                 125

Ile Asn Ala Met Lys Phe Phe Pro Ala Glu Ala Ala Gly Gly Ile Pro
    130                 135                 140

Met Leu Lys Ser Leu Gly Gly Pro Leu Pro Gln Val Thr Phe Cys Pro
145                 150                 155                 160

Thr Gly Gly Val Asn Pro Lys Asn Ala Pro Glu Tyr Leu Ala Leu Lys
                165                 170                 175

Asn Val Ala Cys Val Gly Gly Ser Trp Met Ala Pro Ala Asp Leu Val
            180                 185                 190

Asp Ala Glu Asp Trp Ala Glu Ile Thr Arg Arg Ala Ser Glu Ala Ala
        195                 200                 205

Ala Leu Lys Lys
    210
```

<210> SEQ ID NO 5
<211> LENGTH: 1860
<212> TYPE: DNA
<213> ORGANISM: Methylomonas 16a

<400> SEQUENCE: 5

```
atgaaactga ccaccgacta tcccttgctt aaaaacatcc acacgccggc ggacatacgc    60
```

```
gcgctgtcca aggaccagct ccagcaactg gctgacgagg tgcgcggcta tctgacccac      120
acggtcagca tttccggcgg ccattttgcg gccggcctcg caccgtgga actgaccgtg       180
gccttgcatt atgtgttcaa taccccgtc gatcagttgg tctgggacgt gggccatcag       240
gcctatccgc acaagattct gaccggtcgc aaggagcgca tgccgaccat tcgcaccctg      300
ggcggggtgt cagcctttcc ggcgcgggac gagagcgaat acgatgcctt cggcgtcggc      360
cattccagca cctcgatcag cgcggcactg gcatggcca ttgcgtcgca gctgcgcggc       420
gaagacaaga gatggtagc catcatcggc gacggttcca tcaccggcgg catggcctat       480
gaggcgatga atcatgccgg cgatgtgaat gccaacctgc tggtgatctt gaacgacaac      540
gatatgtcga tctcgccgcc ggtcggggcg atgaacaatt atctgaccaa ggtgttgtcg      600
agcaagtttt attcgtcggt gcgggaagag agcaagaaag ctctggccaa gatgccgtcg      660
gtgtgggaac tggcgcgcaa gaccgaggaa cacgtgaagg gcatgatcgt gcccggtacc      720
ttgttcgagg aattgggctt caattatttc ggcccgatcg acggccatga tgtcgagatg      780
ctggtgtcga ccctgaaaaa tctgaaggat ttgaccgggc cggtattcct gcatgtggtg      840
accaagaagg gcaaaggcta tgcgccagcc gagaaagacc cgttggccta ccatggcgtg      900
ccggctttcg atccgaccaa ggatttcctg cccaaggcgg cgccgtcgcc gcatccgacc      960
tataccgagg tgttcggccg ctggctgtgc gacatggcgc tcaagacga gcgcttgctg     1020
ggcatcacgc cggcgatgcg cgaaggctct ggtttggtgg aattctcaca gaaatttccg     1080
aatcgctatt tcgatgtcgc catcgccgag cagcatgcg tgaccttggc cgccggccag      1140
gcctgccagg gcgccaagcc ggtggtggcg atttattcca ccttcctgca acgcggttac     1200
gatcagttga tccacgacgt ggccttgcag aacttagata tgctctttgc actggatcgt     1260
gccggcttgg tcggcccgga tggaccgacc catgctggcg ccttcgatta cagctacatg     1320
cgctgtattc cgaacatgct gatcatggct ccagccgacg agaacgagtg caggcagatg     1380
ctgaccaccg gcttccaaca ccatggcccg gcttcggtgc gctatccgcg cggcaaaggg     1440
cccgggggcgg caatcgatcc gaccctgacc gcgctggaga tcggcaaggc cgaagtcaga     1500
caccacggca gccgcatcgc cattctggcc tggggcagca tggtcacgcc tgccgtcgaa     1560
gccggcaagc agctgggcgc gacggtggtg aacatgcgtt tcgtcaagcc gttcgatcaa     1620
gccttggtgc tggaattggc caggacgcac gatgtgttcg tcaccgtcga ggaaaacgtc     1680
atcgccggcg cgctggcag tgcgatcaac accttcctgc aggcgcagaa ggtgctgatg     1740
ccggtctgca acatcggcct gcccgaccgc ttcgtcgagc aaggtagtcg cgaggaattg     1800
ctcagcctgg tcggcctcga cagcaagggc atcctcgcca ccatcgaaca gttttgcgct     1860
```

<210> SEQ ID NO 6
<211> LENGTH: 620
<212> TYPE: PRT
<213> ORGANISM: Methylomonas 16a

<400> SEQUENCE: 6

```
Met Lys Leu Thr Thr Asp Tyr Pro Leu Leu Lys Asn Ile His Thr Pro
1               5                   10                  15

Ala Asp Ile Arg Ala Leu Ser Lys Asp Gln Leu Gln Gln Leu Ala Asp
            20                  25                  30

Glu Val Arg Gly Tyr Leu Thr His Thr Val Ser Ile Ser Gly Gly His
        35                  40                  45

Phe Ala Ala Gly Leu Gly Thr Val Glu Leu Thr Val Ala Leu His Tyr
```

```
            50                  55                  60
Val Phe Asn Thr Pro Val Asp Gln Leu Val Trp Asp Val Gly His Gln
 65                  70                  75                  80

Ala Tyr Pro His Lys Ile Leu Thr Gly Arg Lys Glu Arg Met Pro Thr
                 85                  90                  95

Ile Arg Thr Leu Gly Gly Val Ser Ala Phe Pro Ala Arg Asp Glu Ser
                100                 105                 110

Glu Tyr Asp Ala Phe Gly Val Gly His Ser Ser Thr Ser Ile Ser Ala
                115                 120                 125

Ala Leu Gly Met Ala Ile Ala Ser Gln Leu Arg Gly Glu Asp Lys Lys
130                 135                 140

Met Val Ala Ile Ile Gly Asp Gly Ser Ile Thr Gly Gly Met Ala Tyr
145                 150                 155                 160

Glu Ala Met Asn His Ala Gly Asp Val Asn Ala Asn Leu Leu Val Ile
                165                 170                 175

Leu Asn Asp Asn Asp Met Ser Ile Ser Pro Pro Val Gly Ala Met Asn
                180                 185                 190

Asn Tyr Leu Thr Lys Val Leu Ser Ser Lys Phe Tyr Ser Ser Val Arg
                195                 200                 205

Glu Glu Ser Lys Lys Ala Leu Ala Lys Met Pro Ser Val Trp Glu Leu
                210                 215                 220

Ala Arg Lys Thr Glu Glu His Val Lys Gly Met Ile Val Pro Gly Thr
225                 230                 235                 240

Leu Phe Glu Glu Leu Gly Phe Asn Tyr Phe Gly Pro Ile Asp Gly His
                245                 250                 255

Asp Val Glu Met Leu Val Ser Thr Leu Glu Asn Leu Lys Asp Leu Thr
                260                 265                 270

Gly Pro Val Phe Leu His Val Val Thr Lys Lys Gly Lys Gly Tyr Ala
                275                 280                 285

Pro Ala Glu Lys Asp Pro Leu Ala Tyr His Gly Val Pro Ala Phe Asp
                290                 295                 300

Pro Thr Lys Asp Phe Leu Pro Lys Ala Ala Pro Ser Pro His Pro Thr
305                 310                 315                 320

Tyr Thr Glu Val Phe Gly Arg Trp Leu Cys Asp Met Ala Ala Gln Asp
                325                 330                 335

Glu Arg Leu Leu Gly Ile Thr Pro Ala Met Arg Glu Gly Ser Gly Leu
                340                 345                 350

Val Glu Phe Ser Gln Lys Phe Pro Asn Arg Tyr Phe Asp Val Ala Ile
                355                 360                 365

Ala Glu Gln His Ala Val Thr Leu Ala Ala Gly Gln Ala Cys Gln Gly
                370                 375                 380

Ala Lys Pro Val Val Ala Ile Tyr Ser Thr Phe Leu Gln Arg Gly Tyr
385                 390                 395                 400

Asp Gln Leu Ile His Asp Val Ala Leu Gln Asn Leu Asp Met Leu Phe
                405                 410                 415

Ala Leu Asp Arg Ala Gly Leu Val Gly Pro Asp Gly Pro Thr His Ala
                420                 425                 430

Gly Ala Phe Asp Tyr Ser Tyr Met Arg Cys Ile Pro Asn Met Leu Ile
                435                 440                 445

Met Ala Pro Ala Asp Glu Asn Glu Cys Arg Gln Met Leu Thr Thr Gly
                450                 455                 460

Phe Gln His His Gly Pro Ala Ser Val Arg Tyr Pro Arg Gly Lys Gly
465                 470                 475                 480
```

Pro Gly Ala Ala Ile Asp Pro Thr Leu Thr Ala Leu Glu Ile Gly Lys
            485                 490                 495
Ala Glu Val Arg His His Gly Ser Arg Ile Ala Ile Leu Ala Trp Gly
        500                 505                 510
Ser Met Val Thr Pro Ala Val Glu Ala Gly Lys Gln Leu Gly Ala Thr
    515                 520                 525
Val Val Asn Met Arg Phe Val Lys Pro Phe Asp Gln Ala Leu Val Leu
    530                 535                 540
Glu Leu Ala Arg Thr His Asp Val Phe Val Thr Val Glu Glu Asn Val
545                 550                 555                 560
Ile Ala Gly Gly Ala Gly Ser Ala Ile Asn Thr Phe Leu Gln Ala Gln
            565                 570                 575
Lys Val Leu Met Pro Val Cys Asn Ile Gly Leu Pro Asp Arg Phe Val
            580                 585                 590
Glu Gln Gly Ser Arg Glu Glu Leu Leu Ser Leu Val Gly Leu Asp Ser
            595                 600                 605
Lys Gly Ile Leu Ala Thr Ile Glu Gln Phe Cys Ala
610                 615                 620

<210> SEQ ID NO 7
<211> LENGTH: 1182
<212> TYPE: DNA
<213> ORGANISM: Methylomonas 16a

<400> SEQUENCE: 7

```
atgaaaggta tttgcatatt gggcgctacc ggttcgatcg gtgtcagcac gctggatgtc      60
gttgccaggc atccggataa atatcaagtc gttgcgctga ccgccaacgg caatatcgac     120
gcattgtatg aacaatgcct ggcccaccat ccggagtatg cggtggtggt catggaaagc     180
aaggtagcag agttcaaaca gcgcattgcc gcttcgccgg tagcggatat caaggtcttg     240
tcgggtagcg aggccttgca acaggtggcc acgctggaaa acgtcgatac ggtgatggcg     300
gctatcgtcg gcgcggccgg attgttgccg accttggccg cggccaaggc cggcaaaacc     360
gtgctgttgg ccaacaagga agccttggtg atgtcgggac aaatcttcat gcaggccgtc     420
agcgattccg gcgctgtgtt gctgccgata gacagcgagc acaacgccat ctttcagtgc     480
atgccggcgg gttatacgcc aggccataca gccaaacagg cgcgccgcat tttattgacc     540
gcttccggtg gcccatttcg acggacgccg atagaaacgt tgtccagcgt cacgccggat     600
caggccgttg cccatcctaa atgggacatg gggcgcaaga tttcggtcga ttccgccacc     660
atgatgaaca aggtctcgaa actgatcgaa gcctgcttgt tgttcaacat ggagcccgac     720
cagattgaag tcgtcattca tccgcagagc atcattcatt cgatggtgga ctatgtcgat     780
ggttcggttt tggcgcagat gggtaatccc gacatgcgca cgccgatagc gcacgcgatg     840
gcctggccgg aacgctttga ctctggtgtg gcgccgctgg atattttcga agtagggcac     900
atggatttcg aaaaacccga cttgaaacgg tttccttgtc tgagattggc ttatgaagcc     960
atcaagtctg gtggaattat gccaacggta ttgaacgcag ccaatgaaat tgctgtcgaa    1020
gcgttttttaa atgaagaagt caaattcact gacatcgcgg tcatcatcga gcgcagcatg    1080
gcccagttta aaccggacga tgccggcagc ctcgaattgg ttttgcaggc cgatcaagat    1140
gcgcgcgagg tggctagaga catcatcaag accttggtag ct                       1182
```

<210> SEQ ID NO 8
<211> LENGTH: 394

```
<212> TYPE: PRT
<213> ORGANISM: Methylomonas 16a

<400> SEQUENCE: 8

Met Lys Gly Ile Cys Ile Leu Gly Ala Thr Gly Ser Ile Gly Val Ser
 1               5                  10                  15

Thr Leu Asp Val Val Ala Arg His Pro Asp Lys Tyr Gln Val Val Ala
            20                  25                  30

Leu Thr Ala Asn Gly Asn Ile Asp Ala Leu Tyr Glu Gln Cys Leu Ala
        35                  40                  45

His His Pro Glu Tyr Ala Val Val Met Glu Ser Lys Val Ala Glu
    50                  55                  60

Phe Lys Gln Arg Ile Ala Ala Ser Pro Val Ala Asp Ile Lys Val Leu
65                  70                  75                  80

Ser Gly Ser Glu Ala Leu Gln Gln Val Ala Thr Leu Glu Asn Val Asp
                85                  90                  95

Thr Val Met Ala Ala Ile Val Gly Ala Ala Gly Leu Leu Pro Thr Leu
            100                 105                 110

Ala Ala Ala Lys Ala Gly Lys Thr Val Leu Ala Asn Lys Glu Ala
        115                 120                 125

Leu Val Met Ser Gly Gln Ile Phe Met Gln Ala Val Ser Asp Ser Gly
130                 135                 140

Ala Val Leu Leu Pro Ile Asp Ser Glu His Asn Ala Ile Phe Gln Cys
145                 150                 155                 160

Met Pro Ala Gly Tyr Thr Pro Gly His Thr Ala Lys Gln Ala Arg Arg
                165                 170                 175

Ile Leu Leu Thr Ala Ser Gly Gly Pro Phe Arg Arg Thr Pro Ile Glu
            180                 185                 190

Thr Leu Ser Ser Val Thr Pro Asp Gln Ala Val Ala His Pro Lys Trp
        195                 200                 205

Asp Met Gly Arg Lys Ile Ser Val Asp Ser Ala Thr Met Met Asn Lys
    210                 215                 220

Gly Leu Glu Leu Ile Glu Ala Cys Leu Leu Phe Asn Met Glu Pro Asp
225                 230                 235                 240

Gln Ile Glu Val Val Ile His Pro Gln Ser Ile Ile His Ser Met Val
                245                 250                 255

Asp Tyr Val Asp Gly Ser Val Leu Ala Gln Met Gly Asn Pro Asp Met
            260                 265                 270

Arg Thr Pro Ile Ala His Ala Met Ala Trp Pro Glu Arg Phe Asp Ser
        275                 280                 285

Gly Val Ala Pro Leu Asp Ile Phe Glu Val Gly His Met Asp Phe Glu
    290                 295                 300

Lys Pro Asp Leu Lys Arg Phe Pro Cys Leu Arg Leu Ala Tyr Glu Ala
305                 310                 315                 320

Ile Lys Ser Gly Gly Ile Met Pro Thr Val Leu Asn Ala Ala Asn Glu
                325                 330                 335

Ile Ala Val Glu Ala Phe Leu Asn Glu Val Lys Phe Thr Asp Ile
            340                 345                 350

Ala Val Ile Ile Glu Arg Ser Met Ala Gln Phe Lys Pro Asp Asp Ala
        355                 360                 365

Gly Ser Leu Glu Leu Val Leu Gln Ala Asp Gln Asp Ala Arg Glu Val
    370                 375                 380

Ala Arg Asp Ile Ile Lys Thr Leu Val Ala
385                 390
```

<210> SEQ ID NO 9
<211> LENGTH: 693
<212> TYPE: DNA
<213> ORGANISM: Methylomonas 16a

<400> SEQUENCE: 9

```
atgaacccaa ccatccaatg ctgggccgtc gtgcccgcag ccggcgtcgg caaacgcatg      60
caagccgatc gccccaaaca atatttaccg cttgccggta aaacggtcat cgaacacaca     120
ctgactcgac tacttgagtc cgacgccttc caaaaagttg cggtggcgat ttccgtcgaa     180
gacccttatt ggcctgaact gtccatagcc aaacaccccg acatcatcac cgcgcctggc     240
ggcaaggaac gcgccgactc ggtgctgtct gcactgaagg ctttagaaga tatagccagc     300
gaaaatgatt gggtgctggt acacgacgcc gcccgcccct gcttgacggg cagcgacatc     360
cacctttcaaa tcgatacctt aaaaaatgac ccggtcggcg gcatcctggc cttgagttcg     420
cacgacacat tgaaacacgt ggatggtgac acgatcaccg caaccataga cagaaagcac     480
gtctggcgcg ccttgacgcc gcaaatgttc aaatacggca tgttgcgcga cgcgttgcaa     540
cgaaccgaag gcaatccggc cgtcaccgac gaagccagtg cgctggaact tttgggccat     600
aaacccaaaa tcgtggaagg ccgcccggac aacatcaaaa tcacccgccc ggaagatttg     660
gccctggcac aattttatat ggagcaacaa gca                                   693
```

<210> SEQ ID NO 10
<211> LENGTH: 231
<212> TYPE: PRT
<213> ORGANISM: Methylomonas 16a

<400> SEQUENCE: 10

```
Met Asn Pro Thr Ile Gln Cys Trp Ala Val Val Pro Ala Ala Gly Val
1               5                   10                  15

Gly Lys Arg Met Gln Ala Asp Arg Pro Lys Gln Tyr Leu Pro Leu Ala
            20                  25                  30

Gly Lys Thr Val Ile Glu His Thr Leu Thr Arg Leu Leu Glu Ser Asp
        35                  40                  45

Ala Phe Gln Lys Val Ala Val Ala Ile Ser Val Glu Asp Pro Tyr Trp
    50                  55                  60

Pro Glu Leu Ser Ile Ala Lys His Pro Asp Ile Ile Thr Ala Pro Gly
65                  70                  75                  80

Gly Lys Glu Arg Ala Asp Ser Val Leu Ser Ala Leu Lys Ala Leu Glu
                85                  90                  95

Asp Ile Ala Ser Glu Asn Asp Trp Val Leu Val His Asp Ala Ala Arg
            100                 105                 110

Pro Cys Leu Thr Gly Ser Asp Ile His Leu Gln Ile Asp Thr Leu Lys
        115                 120                 125

Asn Asp Pro Val Gly Gly Ile Leu Ala Leu Ser Ser His Asp Thr Leu
    130                 135                 140

Lys His Val Asp Gly Asp Thr Ile Thr Ala Thr Ile Asp Arg Lys His
145                 150                 155                 160

Val Trp Arg Ala Leu Thr Pro Gln Met Phe Lys Tyr Gly Met Leu Arg
                165                 170                 175

Asp Ala Leu Gln Arg Thr Glu Gly Asn Pro Ala Val Thr Asp Glu Ala
            180                 185                 190

Ser Ala Leu Glu Leu Leu Gly His Lys Pro Lys Ile Val Glu Gly Arg
        195                 200                 205
```

```
Pro Asp Asn Ile Lys Ile Thr Arg Pro Glu Asp Leu Ala Leu Ala Gln
    210                 215                 220

Phe Tyr Met Glu Gln Gln Ala
225                 230
```

<210> SEQ ID NO 11
<211> LENGTH: 855
<212> TYPE: DNA
<213> ORGANISM: Methylomonas 16a

<400> SEQUENCE: 11

```
atggattatg cggctgggtg gggcgaaaga tggcctgctc cggcaaaatt gaacttaatg      60
ttgaggatta ccggtcgcag gccagatggc tatcatctgt tgcaaacggt gtttcaaatg    120
ctcgatctat gcgattggtt gacgtttcat ccggttgatg atggccgcgt gacgctgcga    180
aatccaatct ccggcgttcc agagcaggat gacttgactg ttcgggcggc taatttgttg    240
aagtctcata ccggctgtgt gcgcggagtt tgtatcgata tcgagaaaaa tctgcctatg    300
ggtggtggtt tgggtggtgg aagttccgat gctgctacaa ccttggtagt tctaaatcgg    360
ctttggggct tgggcttgtc gaagcgtgag ttgatggatt tgggcttgag gcttggtgcc    420
gatgtgcctg tgtttgtgtt tggttgttcg gcctggggcg aaggtgtgag cgaggatttg    480
caggcaataa cgttgccgga caatggtttt gtcatcatta accggattg ccatgtgaat     540
actggagaaa ttttttctgc agaaaatttg acaaggaata gtgcagtcgt tacaatgagc    600
gactttcttg cagggataa tcggaatgat tgttcggaag tggtttgcaa gttatatcga     660
ccggtgaaag atgcaatcga tgcgttgtta tgctatgcgg aagcgagatt gacggggacc    720
ggtgcatgtg tgttcgctca gttttgtaac aaggaagatg ctgagagtgc gttagaagga    780
ttgaaagatc ggtggctggt gttcttggct aaaggcttga atcagtctgc gctctacaag    840
aaattagaac aggga                                                    855
```

<210> SEQ ID NO 12
<211> LENGTH: 285
<212> TYPE: PRT
<213> ORGANISM: Methylomonas 16a

<400> SEQUENCE: 12

```
Met Asp Tyr Ala Ala Gly Trp Gly Glu Arg Trp Pro Ala Pro Ala Lys
  1               5                  10                  15

Leu Asn Leu Met Leu Arg Ile Thr Gly Arg Arg Pro Asp Gly Tyr His
             20                  25                  30

Leu Leu Gln Thr Val Phe Gln Met Leu Asp Leu Cys Asp Trp Leu Thr
         35                  40                  45

Phe His Pro Val Asp Asp Gly Arg Val Thr Leu Arg Asn Pro Ile Ser
     50                  55                  60

Gly Val Pro Glu Gln Asp Asp Leu Thr Val Arg Ala Ala Asn Leu Leu
 65                  70                  75                  80

Lys Ser His Thr Gly Cys Val Arg Gly Val Cys Ile Asp Ile Glu Lys
                 85                  90                  95

Asn Leu Pro Met Gly Gly Gly Leu Gly Gly Ser Ser Asp Ala Ala
            100                 105                 110

Thr Thr Leu Val Val Leu Asn Arg Leu Trp Gly Leu Gly Leu Ser Lys
        115                 120                 125

Arg Glu Leu Met Asp Leu Gly Leu Arg Leu Gly Ala Asp Val Pro Val
    130                 135                 140
```

```
Phe Val Phe Gly Cys Ser Ala Trp Gly Glu Gly Val Ser Glu Asp Leu
145                 150                 155                 160

Gln Ala Ile Thr Leu Pro Glu Gln Trp Phe Val Ile Ile Lys Pro Asp
                165                 170                 175

Cys His Val Asn Thr Gly Glu Ile Phe Ser Ala Glu Asn Leu Thr Arg
                180                 185                 190

Asn Ser Ala Val Val Thr Met Ser Asp Phe Leu Ala Gly Asp Asn Arg
            195                 200                 205

Asn Asp Cys Ser Glu Val Val Cys Lys Leu Tyr Arg Pro Val Lys Asp
        210                 215                 220

Ala Ile Asp Ala Leu Leu Cys Tyr Ala Glu Ala Arg Leu Thr Gly Thr
225                 230                 235                 240

Gly Ala Cys Val Phe Ala Gln Phe Cys Asn Lys Glu Asp Ala Glu Ser
                245                 250                 255

Ala Leu Glu Gly Leu Lys Asp Arg Trp Leu Val Phe Leu Ala Lys Gly
            260                 265                 270

Leu Asn Gln Ser Ala Leu Tyr Lys Lys Leu Glu Gln Gly
        275                 280                 285

<210> SEQ ID NO 13
<211> LENGTH: 471
<212> TYPE: DNA
<213> ORGANISM: Methylomonas 16a

<400> SEQUENCE: 13
atgatacgcg taggcatggg ttacgacgtg caccgtttca cgacggcga ccacatcatt      60
ttgggcggcg tcaaaatccc ttatgaaaaa ggcctggaag cccattccga cggcgacgtg    120
gtgctgcacg cattggccga cgccatcttg ggagccgccg ctttgggcga catcggcaaa    180
catttccccgg acaccgaccc caatttcaag ggcgccgaca gcagggtgct actgcgccac    240
gtgtacggca tcgtcaagga aaaaggctat aaactggtca acgccgacgt gaccatcatc    300
gctcaggcgc cgaagatgct gccacacgtg cccggcatgc cgccaacat tgccgccgat    360
ctggaaaccg atgtcgattt cattaatgta aaagccacga cgaccgagaa actgggcttt    420
gagggccgta aggaaggcat cgccgtgcag gctgtggtgt tgatagaacg c             471

<210> SEQ ID NO 14
<211> LENGTH: 157
<212> TYPE: PRT
<213> ORGANISM: Methylomonas 16a

<400> SEQUENCE: 14

Met Ile Arg Val Gly Met Gly Tyr Asp Val His Arg Phe Asn Asp Gly
1               5                   10                  15

Asp His Ile Ile Leu Gly Gly Val Lys Ile Pro Tyr Glu Lys Gly Leu
            20                  25                  30

Glu Ala His Ser Asp Gly Asp Val Val Leu His Ala Leu Ala Asp Ala
        35                  40                  45

Ile Leu Gly Ala Ala Ala Leu Gly Asp Ile Gly Lys His Phe Pro Asp
    50                  55                  60

Thr Asp Pro Asn Phe Lys Gly Ala Asp Ser Arg Val Leu Leu Arg His
65                  70                  75                  80

Val Tyr Gly Ile Val Lys Glu Lys Gly Tyr Lys Leu Val Asn Ala Asp
                85                  90                  95

Val Thr Ile Ile Ala Gln Ala Pro Lys Met Leu Pro His Val Pro Gly
```

```
                100             105             110
Met Arg Ala Asn Ile Ala Ala Asp Leu Glu Thr Asp Val Asp Phe Ile
            115                 120                 125

Asn Val Lys Ala Thr Thr Thr Glu Lys Leu Gly Phe Glu Gly Arg Lys
        130                 135                 140

Glu Gly Ile Ala Val Gln Ala Val Val Leu Ile Glu Arg
145                 150                 155
```

<210> SEQ ID NO 15
<211> LENGTH: 1632
<212> TYPE: DNA
<213> ORGANISM: Methylomonas 16a

<400> SEQUENCE: 15

| | | | | | |
|---|---|---|---|---|---|
| atgacaaaat | tcatctttat | caccggcggc | gtggtgtcat | ccttgggaaa | agggatagcc | 60 |
| gcctcctccc | tggcggcgat | tctggaagac | cgcggcctca | agtcactat | cacaaaactc | 120 |
| gatccctaca | tcaacgtcga | ccccggcacc | atgagcccgt | tcaacacgg | cgaggtgttc | 180 |
| gtgaccgaag | acgtgccga | aaccgatttg | gaccttggcc | attacgaacg | gtttttgaaa | 240 |
| accacgatga | ccaagaaaaa | caacttcacc | accggtcagg | tttacgagca | ggtattacgc | 300 |
| aacgagcgca | aggtgatta | tcttggcgcg | accgtgcaag | tcattccaca | tatcaccgac | 360 |
| gaaatcaaac | gccgggtgta | tgaaagcgcc | gaagggaaag | atgtggcatt | gatcgaagtc | 420 |
| ggcggcacgg | tgggcgacat | cgaatcgtta | ccgtttctgg | aaaccatacg | ccagatgggc | 480 |
| gtggaactgg | gtcgtgaccg | cgccttgttc | attcatttga | cgctggtgcc | ttacatcaaa | 540 |
| tcggccggcg | aactgaaaac | caagcccacc | cagcattcgg | tcaaagaact | gcgcaccatc | 600 |
| gggattcagc | cggacatttt | gatctgtcgt | tcagaacaac | cgatcccggc | cagtgaacgc | 660 |
| cgcaagatcg | cgctatttac | caatgtcgcc | gaaaaggcgg | tgatttccgc | gatcgatgcc | 720 |
| gacaccattt | accgcattcc | gctattgctg | cgcaacaag | gcctggacga | cctggtggtc | 780 |
| gatcagttgc | gcctggacgt | accagcggcg | gatttatcgg | cctgggaaaa | ggtcgtcgat | 840 |
| ggcctgactc | atccgaccga | cgaagtcagc | attgcgatcg | tcggtaaata | tgtcgaccac | 900 |
| accgatgcct | acaaatcgct | gaatgaagcc | ctgattcatg | ccggcattca | cacgcgccac | 960 |
| aaggtgcaaa | tcagctacat | cgactccgaa | accatagaag | ccgaaggcac | cgccaaattg | 1020 |
| aaaaacgtcg | atgcgatcct | ggtgccgggt | ggtttcggcg | aacgcggcgt | ggaaggcaag | 1080 |
| atttctaccg | tgcgttttgc | ccgcgagaac | aaaatcccgt | atttgggcat | ttgcttgggc | 1140 |
| atgcaatcgg | cggtaatcga | attcgcccgc | aacgtggttg | gcctggaagg | cgcgcacagc | 1200 |
| accgaattcc | tgccgaaatc | gccacaccct | gtgatcggct | tgatcaccga | atggatggac | 1260 |
| gaagccggcg | aactggtcac | acgcgacgaa | gattccgatc | tgggcggcac | gatgcgtctg | 1320 |
| ggcgcgcaaa | aatgccgcct | gaaggctgat | tccttggctt | ttcagttgta | tcaaaaagac | 1380 |
| gtcatcaccg | agcgtcaccg | ccaccgctac | gaattcaaca | atcaatattt | aaaacaactg | 1440 |
| gaagcggccg | gcatgaaatt | ttccggtaaa | tcgctggacg | gccgcctggt | ggagatcatc | 1500 |
| gagctacccg | aacaccccctg | gttcctggcc | tgccagttcc | atcccgaatt | cacctcgacg | 1560 |
| ccgcgtaacg | gccacgccct | attttcgggc | ttcgtcgaag | cggccgccaa | acacaaaaca | 1620 |
| caaggcacag | ca | | | | | 1632 |

<210> SEQ ID NO 16
<211> LENGTH: 544
<212> TYPE: PRT

<213> ORGANISM: Methylomonas 16a

<400> SEQUENCE: 16

```
Met Thr Lys Phe Ile Phe Ile Thr Gly Gly Val Val Ser Ser Leu Gly
  1               5                  10                  15
Lys Gly Ile Ala Ala Ser Ser Leu Ala Ala Ile Leu Glu Asp Arg Gly
                 20                  25                  30
Leu Lys Val Thr Ile Thr Lys Leu Asp Pro Tyr Ile Asn Val Asp Pro
             35                  40                  45
Gly Thr Met Ser Pro Phe Gln His Gly Glu Val Phe Val Thr Glu Asp
 50                  55                  60
Gly Ala Glu Thr Asp Leu Asp Leu Gly His Tyr Glu Arg Phe Leu Lys
 65                  70                  75                  80
Thr Thr Met Thr Lys Asn Asn Phe Thr Thr Gly Gln Val Tyr Glu
                 85                  90                  95
Gln Val Leu Arg Asn Glu Arg Lys Gly Asp Tyr Leu Gly Ala Thr Val
                100                 105                 110
Gln Val Ile Pro His Ile Thr Asp Glu Ile Lys Arg Arg Val Tyr Glu
            115                 120                 125
Ser Ala Glu Gly Lys Asp Val Ala Leu Ile Glu Val Gly Gly Thr Val
130                 135                 140
Gly Asp Ile Glu Ser Leu Pro Phe Leu Glu Thr Ile Arg Gln Met Gly
145                 150                 155                 160
Val Glu Leu Gly Arg Asp Arg Ala Leu Phe Ile His Leu Thr Leu Val
                165                 170                 175
Pro Tyr Ile Lys Ser Ala Gly Glu Leu Lys Thr Lys Pro Thr Gln His
            180                 185                 190
Ser Val Lys Glu Leu Arg Thr Ile Gly Ile Gln Pro Asp Ile Leu Ile
            195                 200                 205
Cys Arg Ser Glu Gln Pro Ile Pro Ala Ser Glu Arg Arg Lys Ile Ala
            210                 215                 220
Leu Phe Thr Asn Val Ala Glu Lys Ala Val Ile Ser Ala Ile Asp Ala
225                 230                 235                 240
Asp Thr Ile Tyr Arg Ile Pro Leu Leu Leu Arg Glu Gln Gly Leu Asp
                245                 250                 255
Asp Leu Val Val Asp Gln Leu Arg Leu Asp Val Pro Ala Ala Asp Leu
                260                 265                 270
Ser Ala Trp Glu Lys Val Val Asp Gly Leu Thr His Pro Thr Asp Glu
            275                 280                 285
Val Ser Ile Ala Ile Val Gly Lys Tyr Val Asp His Thr Asp Ala Tyr
290                 295                 300
Lys Ser Leu Asn Glu Ala Leu Ile His Ala Gly Ile His Thr Arg His
305                 310                 315                 320
Lys Val Gln Ile Ser Tyr Ile Asp Ser Glu Thr Ile Glu Ala Glu Gly
                325                 330                 335
Thr Ala Lys Leu Lys Asn Val Asp Ala Ile Leu Val Pro Gly Gly Phe
            340                 345                 350
Gly Glu Arg Gly Val Glu Gly Lys Ile Ser Thr Val Arg Phe Ala Arg
            355                 360                 365
Glu Asn Lys Ile Pro Tyr Leu Gly Ile Cys Leu Gly Met Gln Ser Ala
        370                 375                 380
Val Ile Glu Phe Ala Arg Asn Val Val Gly Leu Glu Gly Ala His Ser
385                 390                 395                 400
```

Thr Glu Phe Leu Pro Lys Ser Pro His Pro Val Ile Gly Leu Ile Thr
                405                 410                 415

Glu Trp Met Asp Glu Ala Gly Glu Leu Val Thr Arg Asp Glu Asp Ser
            420                 425                 430

Asp Leu Gly Gly Thr Met Arg Leu Gly Ala Gln Lys Cys Arg Leu Lys
        435                 440                 445

Ala Asp Ser Leu Ala Phe Gln Leu Tyr Gln Lys Asp Val Ile Thr Glu
    450                 455                 460

Arg His Arg His Arg Tyr Glu Phe Asn Asn Gln Tyr Leu Lys Gln Leu
465                 470                 475                 480

Glu Ala Ala Gly Met Lys Phe Ser Gly Lys Ser Leu Asp Gly Arg Leu
                485                 490                 495

Val Glu Ile Ile Glu Leu Pro Glu His Pro Trp Phe Leu Ala Cys Gln
            500                 505                 510

Phe His Pro Glu Phe Thr Ser Thr Pro Arg Asn Gly His Ala Leu Phe
        515                 520                 525

Ser Gly Phe Val Glu Ala Ala Lys His Lys Thr Gln Gly Thr Ala
    530                 535                 540

<210> SEQ ID NO 17
<211> LENGTH: 954
<212> TYPE: DNA
<213> ORGANISM: Methylomonas 16a

<400> SEQUENCE: 17
atgcaaatcg tactcgcaaa ccccgtgga ttctgtgccg cgtggaccg ggccattgaa      60 attgtcgatc aagccatcga agcctttggt gcgccgattt atgtgcggca cgaggtggtg    120
cataaccgca ccgtggtcga tggactgaaa caaaaggtg cggtgttcat cgaggaacta    180
agcgatgtgc cggtgggttc ctacttgatt ttcagcgcgc acggcgtatc caaggaggtg    240
caacaggaag ccgaggagcg ccagttgacg gtattcgatg cgacttgtcc gctggtgacc    300
aaagtgcaca tgcaggttgc caagcatgcc aaacagggcc gagaagtgat tttgatcggc    360
cacgccggtc atccggaagt ggaaggcacg atgggccagt atgaaaaatg caccgaaggc    420
ggcggcattt atctggtcga actccggaa gacgtacgca atttgaaagt caacaatccc    480
aatgatctgg cctatgtgac gcagacgacc ttgtcgatga ccgacaccaa ggtcatggtg    540
gatgcgttac gcgaacaatt tccgtccatt aaggagcaaa aaaggacga tatttgttac    600 gcgacgcaaa accgtcagga tgcggtgcat gatctggcca agatttccga cctgattctg    660
gttgtcggct ctcccaatag ttcgaattcc aaccgtttgc gtgaaatcgc cgtgcaactc    720
ggtaaacccg cttatttgat cgatacttac caggatttga agcaagattg gctggaggga    780
attgaagtag tcggggttac cgcgggcgct tcggcgccgg aagtgttggt gcaggaagtg    840
atcgatcaac tgaaggcatg gggcggcgaa accacttcgg tcagagaaaa cagcggcatc    900
gaggaaaagg tagtctttc gattcccaag gagttgaaaa acatatgca agcg    954

<210> SEQ ID NO 18
<211> LENGTH: 318
<212> TYPE: PRT
<213> ORGANISM: Methylomonas 16a

<400> SEQUENCE: 18

Met Gln Ile Val Leu Ala Asn Pro Arg Gly Phe Cys Ala Gly Val Asp
1               5                   10                  15

Arg Ala Ile Glu Ile Val Asp Gln Ala Ile Glu Ala Phe Gly Ala Pro

```
                  20                  25                  30
Ile Tyr Val Arg His Glu Val Val His Asn Arg Thr Val Asp Gly
         35                  40                  45

Leu Lys Gln Lys Gly Ala Val Phe Ile Glu Glu Leu Ser Asp Val Pro
 50                  55                  60

Val Gly Ser Tyr Leu Ile Phe Ser Ala His Gly Val Ser Lys Glu Val
 65                  70                  75                  80

Gln Gln Glu Ala Glu Arg Gln Leu Thr Val Phe Asp Ala Thr Cys
             85                  90                  95

Pro Leu Val Thr Lys Val His Met Gln Val Ala Lys His Ala Lys Gln
                100                 105                 110

Gly Arg Glu Val Ile Leu Ile Gly His Ala Gly His Pro Glu Val Glu
            115                 120                 125

Gly Thr Met Gly Gln Tyr Glu Lys Cys Thr Glu Gly Gly Ile Tyr
            130                 135                 140

Leu Val Glu Thr Pro Glu Asp Val Arg Asn Leu Lys Val Asn Asn Pro
145                 150                 155                 160

Asn Asp Leu Ala Tyr Val Thr Gln Thr Thr Leu Ser Met Thr Asp Thr
                165                 170                 175

Lys Val Met Val Asp Ala Leu Arg Glu Gln Phe Pro Ser Ile Lys Glu
                180                 185                 190

Gln Lys Lys Asp Asp Ile Cys Tyr Ala Thr Gln Asn Arg Gln Asp Ala
            195                 200                 205

Val His Asp Leu Ala Lys Ile Ser Asp Leu Ile Leu Val Val Gly Ser
        210                 215                 220

Pro Asn Ser Ser Asn Ser Asn Arg Leu Arg Glu Ile Ala Val Gln Leu
225                 230                 235                 240

Gly Lys Pro Ala Tyr Leu Ile Asp Thr Tyr Gln Asp Leu Lys Gln Asp
                245                 250                 255

Trp Leu Glu Gly Ile Glu Val Val Gly Val Thr Ala Gly Ala Ser Ala
                260                 265                 270

Pro Glu Val Leu Val Gln Glu Val Ile Asp Gln Leu Lys Ala Trp Gly
            275                 280                 285

Gly Glu Thr Thr Ser Val Arg Glu Asn Ser Gly Ile Glu Glu Lys Val
        290                 295                 300

Val Phe Ser Ile Pro Lys Glu Leu Lys Lys His Met Gln Ala
305                 310                 315
```

<210> SEQ ID NO 19
<211> LENGTH: 891
<212> TYPE: DNA
<213> ORGANISM: Methylomonas 16a

<400> SEQUENCE: 19

```
atgagtaaat tgaaagccta cctgaccgtc tgccaagaac gcgtcgagcg cgcgctggac    60
gcccgtctgc ctgccgaaaa catactgcca caaaccttgc atcaggccat gcgctattcc   120
gtattgaacg gcggcaaacg cacccggccc ttgttgactt atgcgaccgg tcaggctttg   180
ggcttgccgg aaaacgtgct ggatgcgccg gcttgcgcgg tagaattcat ccatgtgtat   240
tcgctgattc acgacgatct gccggccatg gacaacgatg atctgcgccg cggcaaaccg   300
acctgtcaca aggcttacga cgaggccacc gccattttgg ccggcgacgc actgcaggcg   360
ctggcctttg aagttctggc caacgacccc ggcatcaccg tcgatgcccc ggctcgcctg   420
aaaatgatca cggctttgac ccgcgccagc ggctctcaag gcatggtggg cggtcaagcc   480
```

```
atcgatctcg gctccgtcgg ccgcaaattg acgctgccgg aactcgaaaa catgcatatc      540
cacaagactg gcgccctgat ccgcgccagc gtcaatctgg cggcattatc caaacccgat      600
ctggatactt gctcgccaa gaaactggat cactatgcca aatgcatagg cttgtcgttc       660
caggtcaaag acgacattct cgacatcgaa gccgacaccg cgacactcgg caagactcag      720
ggcaaggaca tcgataacga caaaccgacc taccctgcgc tattgggcat ggctggcgcc      780
aaacaaaaag cccaggaatt gcacgaacaa gcagtcgaaa gcttaacggg atttggcagc      840
gaagccgacc tgctgcgcga actatcgctt tacatcatcg agcgcacgca c               891
```

```
<210> SEQ ID NO 20
<211> LENGTH: 297
<212> TYPE: PRT
<213> ORGANISM: Methylomonas 16a

<400> SEQUENCE: 20

Met Ser Lys Leu Lys Ala Tyr Leu Thr Val Cys Gln Glu Arg Val Glu
1               5                   10                  15

Arg Ala Leu Asp Ala Arg Leu Pro Ala Glu Asn Ile Leu Pro Gln Thr
            20                  25                  30

Leu His Gln Ala Met Arg Tyr Ser Val Leu Asn Gly Gly Lys Arg Thr
        35                  40                  45

Arg Pro Leu Leu Thr Tyr Ala Thr Gly Gln Ala Leu Gly Leu Pro Glu
    50                  55                  60

Asn Val Leu Asp Ala Pro Ala Cys Ala Val Glu Phe Ile His Val Tyr
65                  70                  75                  80

Ser Leu Ile His Asp Asp Leu Pro Ala Met Asp Asn Asp Asp Leu Arg
                85                  90                  95

Arg Gly Lys Pro Thr Cys His Lys Ala Tyr Asp Glu Ala Thr Ala Ile
            100                 105                 110

Leu Ala Gly Asp Ala Leu Gln Ala Leu Ala Phe Glu Val Leu Ala Asn
        115                 120                 125

Asp Pro Gly Ile Thr Val Asp Ala Pro Ala Arg Leu Lys Met Ile Thr
    130                 135                 140

Ala Leu Thr Arg Ala Ser Gly Ser Gln Gly Met Val Gly Gly Gln Ala
145                 150                 155                 160

Ile Asp Leu Gly Ser Val Gly Arg Lys Leu Thr Leu Pro Glu Leu Glu
                165                 170                 175

Asn Met His Ile His Lys Thr Gly Ala Leu Ile Arg Ala Ser Val Asn
            180                 185                 190

Leu Ala Ala Leu Ser Lys Pro Asp Leu Asp Thr Cys Val Ala Lys Lys
        195                 200                 205

Leu Asp His Tyr Ala Lys Cys Ile Gly Leu Ser Phe Gln Val Lys Asp
    210                 215                 220

Asp Ile Leu Asp Ile Glu Ala Asp Thr Ala Thr Leu Gly Lys Thr Gln
225                 230                 235                 240

Gly Lys Asp Ile Asp Asn Asp Lys Pro Thr Tyr Pro Ala Leu Leu Gly
                245                 250                 255

Met Ala Gly Ala Lys Gln Lys Ala Gln Glu Leu His Glu Gln Ala Val
            260                 265                 270

Glu Ser Leu Thr Gly Phe Gly Ser Glu Ala Asp Leu Leu Arg Glu Leu
        275                 280                 285

Ser Leu Tyr Ile Ile Glu Arg Thr His
    290                 295
```

<210> SEQ ID NO 21
<211> LENGTH: 1533
<212> TYPE: DNA
<213> ORGANISM: Methylomonas 16a

<400> SEQUENCE: 21

| | | | | | |
|---|---|---|---|---|---|
| atggccaaca | ccaaacacat | catcatcgtc | ggcgcgggtc | ccggcggact | ttgcgccggc | 60 |
| atgttgctga | gccagcgcgg | cttcaaggta | tcgattttcg | acaaacatgc | agaaatcggc | 120 |
| ggccgcaacc | gcccgatcaa | catgaacggc | tttaccttcg | ataccggtcc | gacattcttg | 180 |
| ttgatgaaag | gcgtgctgga | cgaaatgttc | gaactgtgcg | agcgccgtag | cgaggattat | 240 |
| ctggaattcc | tgccgctaag | cccgatgtac | cgcctgctgt | acgacgaccg | cgacatcttc | 300 |
| gtctattccg | accgcgagaa | catgcgcgcc | gaattgcaac | gggtattcga | cgaaggcacg | 360 |
| gacggctacg | aacagttcat | ggaacaggaa | cgcaaacgct | tcaacgcgct | gtatccctgc | 420 |
| atcacccgcg | attattccag | cctgaaatcc | tttttgtcgc | tggacttgat | caaggccctg | 480 |
| ccgtggctgg | cttttccgaa | aagcgtgttc | aataatctcg | gccagtattt | caaccaggaa | 540 |
| aaaatgcgcc | tggccttttg | ctttcagtcc | aagtatctgg | gcatgtcgcc | gtgggaatgc | 600 |
| ccggcactgt | ttacgatgct | gccctatctg | gagcacgaat | acggcattta | tcacgtcaaa | 660 |
| ggcggcctga | accgcatcgc | ggcggcgatg | gcgcaagtga | tcgcggaaaa | cggcggcgaa | 720 |
| attcacttga | cagcgaaat | cgagtcgctg | atcatcgaaa | acggcgctgc | caagggcgtc | 780 |
| aaattacaac | atggcgcgga | gctgcgcggc | gacgaagtca | tcatcaacgc | ggattttgcc | 840 |
| cacgcgatga | cgcatctggt | caaaccgggc | gtcttgaaaa | aatacacccc | ggaaaacctg | 900 |
| aagcagcgcg | agtattcctg | ttcgaccttc | atgctgtatc | tgggtttgga | caagatttac | 960 |
| gatctgccgc | accataccat | cgtgtttgcc | aaggattaca | ccaccaatat | ccgcaacatt | 1020 |
| ttcgacaaca | aaaccctgac | ggacgatttt | tcgttttacg | tgcaaaacgc | cagcgccagc | 1080 |
| gacgacagcc | tagcgccagc | cggcaaatcg | cgctgtacg | tgctggtgcc | gatgcccaac | 1140 |
| aacgacagcg | gcctggactg | gcaggcgcat | tgccaaaacg | tgcgcgaaca | ggtgttggac | 1200 |
| acgctgggcg | cgcgactggg | attgagcgac | atcagagccc | atatcgaatg | cgaaaaaatc | 1260 |
| atcacgccgc | aaacctggga | aacgacgaa | cacgtttaca | agggcgccac | tttcagtttg | 1320 |
| tcgcacaagt | tcagccaaat | gctgtactgg | cggccgcaca | accgtttcga | ggaactggcc | 1380 |
| aattgctatc | tggtcggcgg | cggcacgcat | cccggtagcg | gtttgccgac | catctacgaa | 1440 |
| tcggcgcgga | tttcggccaa | gctgatttcc | cagaaacatc | gggtgaggtt | caaggacata | 1500 |
| gcacacagcg | cctggctgaa | aaaagccaaa | gcc | | | 1533 |

<210> SEQ ID NO 22
<211> LENGTH: 511
<212> TYPE: PRT
<213> ORGANISM: Methylomonas 16a

<400> SEQUENCE: 22

Met Ala Asn Thr Lys His Ile Ile Ile Val Gly Ala Gly Pro Gly Gly
1               5                   10                  15

Leu Cys Ala Gly Met Leu Leu Ser Gln Arg Gly Phe Lys Val Ser Ile
            20                  25                  30

Phe Asp Lys His Ala Glu Ile Gly Gly Arg Asn Arg Pro Ile Asn Met
        35                  40                  45

Asn Gly Phe Thr Phe Asp Thr Gly Pro Thr Phe Leu Leu Met Lys Gly

```
                     -continued
      50                55                60
Val Leu Asp Glu Met Phe Glu Leu Cys Glu Arg Arg Ser Glu Asp Tyr
65                  70                  75                  80

Leu Glu Phe Leu Pro Leu Ser Pro Met Tyr Arg Leu Tyr Asp Asp
                85                  90                  95

Arg Asp Ile Phe Val Tyr Ser Asp Arg Glu Asn Met Arg Ala Glu Leu
              100                 105                 110

Gln Arg Val Phe Asp Glu Gly Thr Asp Gly Tyr Gln Phe Met Glu
              115                 120                 125

Gln Glu Arg Lys Arg Phe Asn Ala Leu Tyr Pro Cys Ile Thr Arg Asp
130                 135                 140

Tyr Ser Ser Leu Lys Ser Phe Leu Ser Leu Asp Leu Ile Lys Ala Leu
145                 150                 155                 160

Pro Trp Leu Ala Phe Pro Lys Ser Val Phe Asn Asn Leu Gly Gln Tyr
              165                 170                 175

Phe Asn Gln Glu Lys Met Arg Leu Ala Phe Cys Phe Gln Ser Lys Tyr
              180                 185                 190

Leu Gly Met Ser Pro Trp Glu Cys Pro Ala Leu Phe Thr Met Leu Pro
              195                 200                 205

Tyr Leu Glu His Glu Tyr Gly Ile Tyr His Val Lys Gly Gly Leu Asn
210                 215                 220

Arg Ile Ala Ala Ala Met Ala Gln Val Ile Ala Glu Asn Gly Gly Glu
225                 230                 235                 240

Ile His Leu Asn Ser Glu Ile Glu Ser Leu Ile Ile Glu Asn Gly Ala
              245                 250                 255

Ala Lys Gly Val Lys Leu Gln His Gly Ala Glu Leu Arg Gly Asp Glu
              260                 265                 270

Val Ile Ile Asn Ala Asp Phe Ala His Ala Met Thr His Leu Val Lys
              275                 280                 285

Pro Gly Val Leu Lys Lys Tyr Thr Pro Glu Asn Leu Lys Gln Arg Glu
290                 295                 300

Tyr Ser Cys Ser Thr Phe Met Leu Tyr Leu Gly Leu Asp Lys Ile Tyr
305                 310                 315                 320

Asp Leu Pro His His Thr Ile Val Phe Ala Lys Asp Tyr Thr Thr Asn
              325                 330                 335

Ile Arg Asn Ile Phe Asp Asn Lys Thr Leu Thr Asp Asp Phe Ser Phe
              340                 345                 350

Tyr Val Gln Asn Ala Ser Ala Ser Asp Asp Ser Leu Ala Pro Ala Gly
              355                 360                 365

Lys Ser Ala Leu Tyr Val Leu Val Pro Met Pro Asn Asn Asp Ser Gly
              370                 375                 380

Leu Asp Trp Gln Ala His Cys Gln Asn Val Arg Glu Gln Val Leu Asp
385                 390                 395                 400

Thr Leu Gly Ala Arg Leu Gly Leu Ser Asp Ile Arg Ala His Ile Glu
                    405                 410                 415

Cys Glu Lys Ile Ile Thr Pro Gln Thr Trp Glu Thr Asp Glu His Val
              420                 425                 430

Tyr Lys Gly Ala Thr Phe Ser Leu Ser His Lys Phe Ser Gln Met Leu
              435                 440                 445

Tyr Trp Arg Pro His Asn Arg Phe Glu Glu Leu Ala Asn Cys Tyr Leu
              450                 455                 460

Val Gly Gly Gly Thr His Pro Gly Ser Gly Leu Pro Thr Ile Tyr Glu
465                 470                 475                 480
```

Ser Ala Arg Ile Ser Ala Lys Leu Ile Ser Gln Lys His Arg Val Arg
                485                 490                 495

Phe Lys Asp Ile Ala His Ser Ala Trp Leu Lys Lys Ala Lys Ala
        500                 505                 510

<210> SEQ ID NO 23
<211> LENGTH: 1491
<212> TYPE: DNA
<213> ORGANISM: Methylomonas 16a

<400> SEQUENCE: 23

```
atgaactcaa atgacaacca acgcgtgatc gtgatcggcg ccggcctcgg cggcctgtcc      60
gccgctattt cgctggccac ggccggcttt tccgtgcaac tcatcgaaaa aaacgacaag     120
gtcggcggca agctcaacat catgaccaaa gacggcttta ccttcgatct ggggccgtcc     180
attttgacga tgccgcacat ctttgaggcc ttgttcacag gggccggcaa aaacatggcc     240
gattacgtgc aaatccagaa agtcgaaccg cactggcgca atttcttcga ggacggtagc     300
gtgatcgact tgtgcgaaga cgccgaaacc cagcgccgcg agctggataa acttggcccc     360
ggcacttacg cgcaattcca gcgctttctg gactattcga aaaacctctg cacggaaacc     420
gaagccggtt acttcgccaa gggcctggac ggcttttggg atttactcaa gttttacggc     480
ccgctccgca gcctgctgag tttcgacgtc ttccgcagca tggaccaggg cgtgcgccgc     540
tttatttccg atcccaagtt ggtcgaaatc ctgaattact tcatcaaata cgtcggctcc     600
tcgccttacg atgcgcccgc cttgatgaac ctgctgcctt acattcaata tcattacggc     660
ctgtggtacg tgaaaggcgg catgtatggc atggcgcagg ccatggaaaa actggccgtg     720
gaattgggcg tcgagattcg tttagatgcc gaggtgtcgg aaatccaaaa acaggacggc     780
agagcctgcg ccgtaaagtt ggcgaacggc gacgtgctgc cggccgacat cgtggtgtcg     840
aacatggaag tgattccggc gatggaaaaa ctgctgcgca gcccggccag cgaactgaaa     900
aaaatgcagc gcttcgagcc tagctgttcc ggcctggtgc tgcacttggg cgtggacagg     960
ctgtatccgc aactggcgca ccacaatttc ttttattccg atcatccgcg cgaacatttc    1020
gatgcggtat tcaaaagcca tcgcctgtcg acgatccga ccatttatct ggtcgcgccg    1080
tgcaagaccg accccgccca ggcgccggcc ggctgcgaga tcatcaaaat cctgccccat    1140
atcccgcacc tcgaccccga caaactgctg accgccgagg attattcagc cttgcgcgag    1200
cgggtgctgg tcaaactcga acgcatgggc ctgacggatt tacgccaaca catcgtgacc    1260
gaagaatact ggacgccgct ggatattcag gccaaatatt attcaaacca gggctcgatt    1320
tacggcgtgg tcgccgaccg cttcaaaaac ctgggtttca aggcacctca acgcagcagc    1380
gaattatcca atctgtattt cgtcggcggc agcgtcaatc ccggcggcgg catgccgatg    1440
gtgacgctgt ccgggcaatt ggtgagggac aagattgtgg cggatttgca a             1491
```

<210> SEQ ID NO 24
<211> LENGTH: 497
<212> TYPE: PRT
<213> ORGANISM: Methylomonas 16a

<400> SEQUENCE: 24

Met Asn Ser Asn Asp Asn Gln Arg Val Ile Val Ile Gly Ala Gly Leu
1               5                   10                  15

Gly Gly Leu Ser Ala Ala Ile Ser Leu Ala Thr Ala Gly Phe Ser Val
            20                  25                  30

-continued

```
Gln Leu Ile Glu Lys Asn Asp Lys Val Gly Lys Leu Asn Ile Met
     35                  40                  45

Thr Lys Asp Gly Phe Thr Phe Asp Leu Gly Pro Ser Ile Leu Thr Met
 50                  55                  60

Pro His Ile Phe Glu Ala Leu Phe Thr Gly Ala Gly Lys Asn Met Ala
 65                  70                  75                  80

Asp Tyr Val Gln Ile Gln Lys Val Glu Pro His Trp Arg Asn Phe Phe
                     85                  90                  95

Glu Asp Gly Ser Val Ile Asp Leu Cys Glu Asp Ala Glu Thr Gln Arg
                100                 105                 110

Arg Glu Leu Asp Lys Leu Gly Pro Gly Thr Tyr Ala Gln Phe Gln Arg
            115                 120                 125

Phe Leu Asp Tyr Ser Lys Asn Leu Cys Thr Glu Thr Glu Ala Gly Tyr
        130                 135                 140

Phe Ala Lys Gly Leu Asp Gly Phe Trp Asp Leu Leu Lys Phe Tyr Gly
145                 150                 155                 160

Pro Leu Arg Ser Leu Leu Ser Phe Asp Val Phe Arg Ser Met Asp Gln
                165                 170                 175

Gly Val Arg Arg Phe Ile Ser Asp Pro Lys Leu Val Glu Ile Leu Asn
            180                 185                 190

Tyr Phe Ile Lys Tyr Val Gly Ser Ser Pro Tyr Asp Ala Pro Ala Leu
        195                 200                 205

Met Asn Leu Leu Pro Tyr Ile Gln Tyr His Tyr Gly Leu Trp Tyr Val
    210                 215                 220

Lys Gly Gly Met Tyr Gly Met Ala Gln Ala Met Glu Lys Leu Ala Val
225                 230                 235                 240

Glu Leu Gly Val Glu Ile Arg Leu Asp Ala Glu Val Ser Glu Ile Gln
                245                 250                 255

Lys Gln Asp Gly Arg Ala Cys Ala Val Lys Leu Ala Asn Gly Asp Val
            260                 265                 270

Leu Pro Ala Asp Ile Val Val Ser Asn Met Glu Val Ile Pro Ala Met
        275                 280                 285

Glu Lys Leu Leu Arg Ser Pro Ala Ser Glu Leu Lys Lys Met Gln Arg
    290                 295                 300

Phe Glu Pro Ser Cys Ser Gly Leu Val Leu His Leu Gly Val Asp Arg
305                 310                 315                 320

Leu Tyr Pro Gln Leu Ala His His Asn Phe Phe Tyr Ser Asp His Pro
                325                 330                 335

Arg Glu His Phe Asp Ala Val Phe Lys Ser His Arg Leu Ser Asp Asp
            340                 345                 350

Pro Thr Ile Tyr Leu Val Ala Pro Cys Lys Thr Asp Pro Ala Gln Ala
        355                 360                 365

Pro Ala Gly Cys Glu Ile Ile Lys Ile Leu Pro His Ile Pro His Leu
    370                 375                 380

Asp Pro Asp Lys Leu Leu Thr Ala Glu Asp Tyr Ser Ala Leu Arg Glu
385                 390                 395                 400

Arg Val Leu Val Lys Leu Glu Arg Met Gly Leu Thr Asp Leu Arg Gln
                405                 410                 415

His Ile Val Thr Glu Glu Tyr Trp Thr Pro Leu Asp Ile Gln Ala Lys
            420                 425                 430

Tyr Tyr Ser Asn Gln Gly Ser Ile Tyr Gly Val Val Ala Asp Arg Phe
        435                 440                 445

Lys Asn Leu Gly Phe Lys Ala Pro Gln Arg Ser Ser Glu Leu Ser Asn
```

```
                   450                  455                  460
Leu Tyr Phe Val Gly Gly Ser Val Asn Pro Gly Gly Met Pro Met
465                 470                  475                 480

Val Thr Leu Ser Gly Gln Leu Val Arg Asp Lys Ile Val Ala Asp Leu
                    485                 490                 495

Gln

<210> SEQ ID NO 25
<211> LENGTH: 912
<212> TYPE: DNA
<213> ORGANISM: Pantoea stewartii

<400> SEQUENCE: 25
ttgacggtct gcgcaaaaaa acacgttcac cttactggca tttcggctga gcagttgctg    60
gctgatatcg atagccgcct tgatcagtta ctgccggttc agggtgagcg ggattgtgtg   120
ggtgccgcga tgcgtgaagg cacgctggca ccgggcaaac gtattcgtcc gatgctgctg   180
ttattaacag cgcgcgatct tggctgtgcg atcagtcacg ggggattact ggatttagcc   240
tgcgcggttg aaatggtgca tgctgcctcg ctgattctgg atgatatgcc ctgcatggac   300
gatgcgcaga tgcgtcgggg cgtcccacc attcacacgc agtacggtga acatgtggcg   360
attctggcgg cggtcgcttt actcagcaaa gcgtttgggg tgattgccga ggctgaaggt   420
ctgacgccga tagccaaaac tcgcgcggtg tcggagctgt ccactgcgat tggcatgcag   480
ggtctggttc agggccagtt taaggacctc tcggaaggcg ataaacccg cagcgccgat   540
gccatactgc taaccaatca gtttaaaacc agcacgctgt tttgcgcgtc aacgcaaatg   600
gcgtccattg cggccaacgc gtcctgcgaa gcgcgtgaga acctgcatcg tttctcgctc   660
gatctcggcc aggcctttca gttgcttgac gatcttaccg atggcatgac cgataccggc   720
aaagacatca atcaggatgc aggtaaatca acgctggtca atttattagg ctcaggcgcg   780
gtcgaagaac gcctgcgaca gcatttgcgc ctggccagtg aacacctttc gcggcatgc   840
caaaacggcc attccaccac ccaactttt attcaggcct ggtttgacaa aaaactcgct   900
gccgtcagtt aa                                                      912

<210> SEQ ID NO 26
<211> LENGTH: 303
<212> TYPE: PRT
<213> ORGANISM: Pantoea stewartii

<400> SEQUENCE: 26

Leu Thr Val Cys Ala Lys Lys His Val His Leu Thr Gly Ile Ser Ala
1               5                  10                  15

Glu Gln Leu Leu Ala Asp Ile Asp Ser Arg Leu Asp Gln Leu Leu Pro
                20                  25                  30

Val Gln Gly Glu Arg Asp Cys Val Gly Ala Ala Met Arg Glu Gly Thr
            35                  40                  45

Leu Ala Pro Gly Lys Arg Ile Arg Pro Met Leu Leu Leu Thr Ala
        50                  55                  60

Arg Asp Leu Gly Cys Ala Ile Ser His Gly Gly Leu Leu Asp Leu Ala
65                  70                  75                  80

Cys Ala Val Glu Met Val His Ala Ala Ser Leu Ile Leu Asp Asp Met
                85                  90                  95

Pro Cys Met Asp Asp Ala Gln Met Arg Arg Gly Arg Pro Thr Ile His
                100                 105                 110
```

```
Thr Gln Tyr Gly Glu His Val Ala Ile Leu Ala Ala Val Ala Leu Leu
        115                 120                 125

Ser Lys Ala Phe Gly Val Ile Ala Glu Ala Glu Gly Leu Thr Pro Ile
130                 135                 140

Ala Lys Thr Arg Ala Val Ser Glu Leu Ser Thr Ala Ile Gly Met Gln
145                 150                 155                 160

Gly Leu Val Gln Gly Gln Phe Lys Asp Leu Ser Glu Gly Asp Lys Pro
                165                 170                 175

Arg Ser Ala Asp Ala Ile Leu Leu Thr Asn Gln Phe Lys Thr Ser Thr
                180                 185                 190

Leu Phe Cys Ala Ser Thr Gln Met Ala Ser Ile Ala Ala Asn Ala Ser
        195                 200                 205

Cys Glu Ala Arg Glu Asn Leu His Arg Phe Ser Leu Asp Leu Gly Gln
210                 215                 220

Ala Phe Gln Leu Leu Asp Asp Leu Thr Asp Gly Met Thr Asp Thr Gly
225                 230                 235                 240

Lys Asp Ile Asn Gln Asp Ala Gly Lys Ser Thr Leu Val Asn Leu Leu
                245                 250                 255

Gly Ser Gly Ala Val Glu Glu Arg Leu Arg Gln His Leu Arg Leu Ala
                260                 265                 270

Ser Glu His Leu Ser Ala Ala Cys Gln Asn Gly His Ser Thr Thr Gln
        275                 280                 285

Leu Phe Ile Gln Ala Trp Phe Asp Lys Lys Leu Ala Ala Val Ser
        290                 295                 300

<210> SEQ ID NO 27
<211> LENGTH: 1296
<212> TYPE: DNA
<213> ORGANISM: Pantoea stewartii

<400> SEQUENCE: 27
atgagccatt ttgcggtgat cgcaccgccc ttttttcagcc atgttcgcgc tctgcaaaac     60
cttgctcagg aattagtggc ccgcggtcat cgtgttacgt ttttttcagca acatgactgc    120 aaagcgctgg taacgggcag cgatatcgga ttccagaccg tcggactgca aacgcatcct    180
cccggttcct atcgcacct gctgcacctg gccgcgcacc cactcggacc ctcgatgtta     240
cgactgatca atgaaatggc acgtaccagc gatatgcttt gccgggaact gcccgccgct    300
tttcatgcgt tgcagataga gggcgtgatc gttgatcaaa tggagccggc aggtgcagta    360
gtcgcagaag cgtcaggtct gccgtttgtt tcggtgcct cgcgctgcc gctcaaccgc      420 gaaccgggtt tgcctctggc ggtgatgcct ttcgagtacg gcaccagcga tgcggctcgg    480
gaacgctata ccaccagcga aaaatttat gactggctga tgcgacgtca cgatcgtgtg     540
atcgcgcatc atgcatgcag aatgggttta gccccgcgtg aaaaactgca tcattgtttt    600
tctccactgg cacaaatcag ccagttgatc cccgaactgg attttccccg caaagcgctg    660
ccagactgct tcatgcggt tggaccgtta cggcaacccc aggggacgcc ggggtcatca     720
acttcttatt ttccgtcccc ggacaaaccc cgtattttg cctcgctggg cacccctgcag    780 ggacatcgtt atggcctgtt caggaccatc gccaaagcct gcgaagaggt ggatgcgcag    840
ttactgttgg cacactgtgg cggcctctca gccacgcagg caggtgaact ggcccggggc    900
ggggacattc aggttgtgga ttttgccgat caatccgcag cactttcaca ggcacagttg    960
acaatcacac atggtgggat gaatacggta ctggacgcta ttgcttcccg cacaccgcta   1020
ctggcgctgc cgctggcatt tgatcaacct ggcgtggcat cacgaattgt ttatcatggc   1080
```

```
atcggcaagc gtgcgtctcg gtttactacc agccatgcgc tggcgcggca gattcgatcg    1140
ctgctgacta acaccgatta cccgcagcgt atgacaaaaa ttcaggccgc attgcgtctg    1200
gcaggcggca caccagccgc cgccgatatt gttgaacagg cgatgcggac ctgtcagcca    1260
gtactcagtg ggcaggatta tgcaaccgca ctatga                              1296
```

<210> SEQ ID NO 28
<211> LENGTH: 431
<212> TYPE: PRT
<213> ORGANISM: Pantoea stewartii

<400> SEQUENCE: 28

```
Met Ser His Phe Ala Val Ile Ala Pro Pro Phe Phe Ser His Val Arg
1               5                   10                  15

Ala Leu Gln Asn Leu Ala Gln Glu Leu Val Ala Arg Gly His Arg Val
            20                  25                  30

Thr Phe Phe Gln Gln His Asp Cys Lys Ala Leu Val Thr Gly Ser Asp
        35                  40                  45

Ile Gly Phe Gln Thr Val Gly Leu Gln Thr His Pro Pro Gly Ser Leu
    50                  55                  60

Ser His Leu Leu His Leu Ala Ala His Pro Leu Gly Pro Ser Met Leu
65                  70                  75                  80

Arg Leu Ile Asn Glu Met Ala Arg Thr Ser Asp Met Leu Cys Arg Glu
                85                  90                  95

Leu Pro Ala Ala Phe His Ala Leu Gln Ile Glu Gly Val Ile Val Asp
            100                 105                 110

Gln Met Glu Pro Ala Gly Ala Val Val Ala Glu Ala Ser Gly Leu Pro
        115                 120                 125

Phe Val Ser Val Ala Cys Ala Leu Pro Leu Asn Arg Glu Pro Gly Leu
    130                 135                 140

Pro Leu Ala Val Met Pro Phe Glu Tyr Gly Thr Ser Asp Ala Ala Arg
145                 150                 155                 160

Glu Arg Tyr Thr Thr Ser Glu Lys Ile Tyr Asp Trp Leu Met Arg Arg
                165                 170                 175

His Asp Arg Val Ile Ala His Ala Cys Arg Met Gly Leu Ala Pro
            180                 185                 190

Arg Glu Lys Leu His His Cys Phe Ser Pro Leu Ala Gln Ile Ser Gln
        195                 200                 205

Leu Ile Pro Glu Leu Asp Phe Pro Arg Lys Ala Leu Pro Asp Cys Phe
    210                 215                 220

His Ala Val Gly Pro Leu Arg Gln Pro Gln Gly Thr Pro Gly Ser Ser
225                 230                 235                 240

Thr Ser Tyr Phe Pro Ser Pro Asp Lys Pro Arg Ile Phe Ala Ser Leu
                245                 250                 255

Gly Thr Leu Gln Gly His Arg Tyr Gly Leu Phe Arg Thr Ile Ala Lys
            260                 265                 270

Ala Cys Glu Glu Val Asp Ala Gln Leu Leu Ala His Cys Gly Gly
        275                 280                 285

Leu Ser Ala Thr Gln Ala Gly Glu Leu Ala Arg Gly Gly Asp Ile Gln
    290                 295                 300

Val Val Asp Phe Ala Asp Gln Ser Ala Ala Leu Ser Gln Ala Gln Leu
305                 310                 315                 320

Thr Ile Thr His Gly Gly Met Asn Thr Val Leu Asp Ala Ile Ala Ser
                325                 330                 335
```

Arg Thr Pro Leu Leu Ala Leu Pro Leu Ala Phe Asp Gln Pro Gly Val
            340                 345                 350

Ala Ser Arg Ile Val Tyr His Gly Ile Gly Lys Arg Ala Ser Arg Phe
            355                 360                 365

Thr Thr Ser His Ala Leu Ala Arg Gln Ile Arg Ser Leu Leu Thr Asn
        370                 375                 380

Thr Asp Tyr Pro Gln Arg Met Thr Lys Ile Gln Ala Ala Leu Arg Leu
385                 390                 395                 400

Ala Gly Gly Thr Pro Ala Ala Asp Ile Val Glu Gln Ala Met Arg
            405                 410                 415

Thr Cys Gln Pro Val Leu Ser Gly Gln Asp Tyr Ala Thr Ala Leu
            420                 425                 430

<210> SEQ ID NO 29
<211> LENGTH: 1149
<212> TYPE: DNA
<213> ORGANISM: Pantoea stewartii

<400> SEQUENCE: 29

```
atgcaaccgc actatgatct cattctggtc ggtgccggtc tggctaatgg ccttatcgcg      60
ctccggcttc agcaacagca tccggatatg cggatcttgc ttattgaggc gggtcctgag     120
gcgggaggga accatacctg gtcctttcac gaagaggatt taacgctgaa tcagcatcgc     180
tggatagcgc cgcttgtggt ccatcactgg cccgactacc aggttcgttt ccccccaacgc    240
cgtcgccatg tgaacagtgg ctactactgc gtgacctccc ggcatttcgc cgggatactc    300
cggcaacagt ttggacaaca tttatggctg cataccgcgg tttcagccgt tcatgctgaa    360
tcggtccagt tagcggatgg ccggattatt catgccagta cagtgatcga cggacggggt    420
tacacgcctg attctgcact acgcgtagga ttccaggcat ttatcggtca ggagtggcaa    480
ctgagcgcgc gcatggtttt atcgtcaccg attatcatgg atgcgacggt cgatcagcaa    540
aatggctacc gctttgtttta taccctgccg cttccgcaa ccgcactgct gatcgaagac    600
acacactaca ttgacaaggc taatcttcag gccgaacggg cgcgtcagaa cattcgcgat    660
tatgctgcgc gacagggttg gccgttacag acgttgctgc gggaagaaca gggtgcattg    720
cccattacgt taacgggcga taatcgtcag ttttggcaac agcaaccgca agcctgtagc    780
ggattacgcg ccgggctgtt tcatccgaca accggctact ccctaccgct cgcggtggcg    840
ctggccgatc gtctcagcgc gctggatgtg tttacctctt cctctgttca ccagacgatt    900
gctcactttg cccagcaacg ttggcagcaa caggggtttt tccgcatgct gaatcgcatg    960
ttgttttag ccggaccggc cgagtcacgc tggcgtgtga tgcagcgttt ctatggctta   1020
cccgaggatt tgattgcccg cttttatgcg ggaaaactca ccgtgaccga tcggctacgc   1080
attctgagcg gcaagccgcc cgttcccgtt ttcgcggcat tgcaggcaat tatgacgact   1140
catcgttga                                                            1149
```

<210> SEQ ID NO 30
<211> LENGTH: 382
<212> TYPE: PRT
<213> ORGANISM: Pantoea stewartii

<400> SEQUENCE: 30

Met Gln Pro His Tyr Asp Leu Ile Leu Val Gly Ala Gly Leu Ala Asn
1               5                   10                  15

Gly Leu Ile Ala Leu Arg Leu Gln Gln Gln His Pro Asp Met Arg Ile

```
                  20                  25                  30
Leu Leu Ile Glu Ala Gly Pro Glu Ala Gly Asn His Thr Trp Ser
         35                  40                  45
Phe His Glu Glu Asp Leu Thr Leu Asn Gln His Arg Trp Ile Ala Pro
 50                  55                  60
Leu Val Val His His Trp Pro Asp Tyr Gln Val Arg Phe Pro Gln Arg
 65                  70                  75                  80
Arg Arg His Val Asn Ser Gly Tyr Tyr Cys Val Thr Ser Arg His Phe
                 85                  90                  95
Ala Gly Ile Leu Arg Gln Gln Phe Gly Gln His Leu Trp Leu His Thr
             100                 105                 110
Ala Val Ser Ala Val His Ala Glu Ser Val Gln Leu Ala Asp Gly Arg
         115                 120                 125
Ile Ile His Ala Ser Thr Val Ile Asp Gly Arg Gly Tyr Thr Pro Asp
     130                 135                 140
Ser Ala Leu Arg Val Gly Phe Gln Ala Phe Ile Gly Gln Glu Trp Gln
145                 150                 155                 160
Leu Ser Ala Pro His Gly Leu Ser Ser Pro Ile Ile Met Asp Ala Thr
                 165                 170                 175
Val Asp Gln Gln Asn Gly Tyr Arg Phe Val Tyr Thr Leu Pro Leu Ser
             180                 185                 190
Ala Thr Ala Leu Leu Ile Glu Asp Thr His Tyr Ile Asp Lys Ala Asn
         195                 200                 205
Leu Gln Ala Glu Arg Ala Arg Gln Asn Ile Arg Asp Tyr Ala Ala Arg
     210                 215                 220
Gln Gly Trp Pro Leu Gln Thr Leu Leu Arg Glu Gln Gly Ala Leu
225                 230                 235                 240
Pro Ile Thr Leu Thr Gly Asp Asn Arg Gln Phe Trp Gln Gln Pro
                 245                 250                 255
Gln Ala Cys Ser Gly Leu Arg Ala Gly Leu Phe His Pro Thr Thr Gly
             260                 265                 270
Tyr Ser Leu Pro Leu Ala Val Ala Leu Ala Asp Arg Leu Ser Ala Leu
         275                 280                 285
Asp Val Phe Thr Ser Ser Ser Val His Gln Thr Ile Ala His Phe Ala
     290                 295                 300
Gln Gln Arg Trp Gln Gln Gln Gly Phe Phe Arg Met Leu Asn Arg Met
305                 310                 315                 320
Leu Phe Leu Ala Gly Pro Ala Glu Ser Arg Trp Arg Val Met Gln Arg
                 325                 330                 335
Phe Tyr Gly Leu Pro Glu Asp Leu Ile Ala Arg Phe Tyr Ala Gly Lys
             340                 345                 350
Leu Thr Val Thr Asp Arg Leu Arg Ile Leu Ser Gly Lys Pro Pro Val
         355                 360                 365
Pro Val Phe Ala Ala Leu Gln Ala Ile Met Thr Thr His Arg
     370                 375                 380

<210> SEQ ID NO 31
<211> LENGTH: 1479
<212> TYPE: DNA
<213> ORGANISM: Pantoea stewartii

<400> SEQUENCE: 31
atgaaaccaa ctacggtaat tggtgcgggc tttggtggcc tggcactggc aattcgttta      60
caggccgcag gtattcctgt tttgctgctt gagcagcgcg acaagccggg tggccgggct     120
```

-continued

```
tatgtttatc aggagcaggg ctttacttttt gatgcaggcc ctaccgttat caccgatccc    180
agcgcgattg aagaactgtt tgctctggcc ggtaaacagc ttaaggatta cgtcgagctg    240
ttgccggtca cgccgtttta tcgcctgtgc tgggagtccg gcaaggtctt caattacgat    300
aacgaccagg cccagttaga agcgcagata cagcagttta atccgcgcga tgttgcgggt    360
tatcgagcgt tccttgacta ttcgcgtgcc gtattcaatg agggctatct gaagctcggc    420
actgtgcctt ttttatcgtt caaagacatg cttcgggccg cgccccagtt ggcaaagctg    480
caggcatggc gcagcgttta cagtaaagtt gccggctaca ttgaggatga gcatcttcgg    540
caggcgtttt cttttcactc gctcttagtg gggggaatc cgtttgcaac ctcgtccatt    600
tatacgctga ttcacgcgtt agaacgggaa tgggcgtct ggtttccacg cggtggaacc    660
ggtgcgctgg tcaatggcat gatcaagctg tttcaggatc tgggcggcga agtcgtgctt    720
aacgcccggg tcagtcatat ggaaaccgtt ggggacaaga ttcaggccgt gcagttggaa    780
gacggcagac ggtttgaaac ctgcgcggtg gcgtcgaacg ctgatgttgt acatacctat    840
cgcgatctgc tgtctcagca tcccgcagcc gctaagcagg cgaaaaaact gcaatccaag    900
cgtatgagta actcactgtt tgtactctat tttggtctca accatcatca cgatcaactc    960
gcccatcata ccgtctgttt tgggccacgc taccgtgaac tgattcacga aattttttaac   1020 catgatggtc tggctgagga ttttttcgctt tatttacacg caccttgtgt cacggatccg   1080
tcactggcac cggaagggtg cggcagctat tatgtgctgg cgcctgttcc acacttaggc   1140
acggcgaacc tcgactgggc ggtagaagga ccccgactgc gcgatcgtat ttttgactac   1200
cttgagcaac attacatgcc tggcttgcga agccagttgg tgacgcaccg tatgtttacg   1260
ccgttcgatt ccgcgacga gctcaatgcc tggcaaggtt cggccttctc ggttgaacct    1320
attctgaccc agagcgcctg gttccgacca cataaccgcg ataagcacat tgataatctt   1380
tatctggttg gcgcaggcac ccatcctggc gcgggcattc ccggcgtaat cggctcggcg    1440
aaggcgacgg caggcttaat gctggaggac ctgattttga                          1479
```

<210> SEQ ID NO 32
<211> LENGTH: 492
<212> TYPE: PRT
<213> ORGANISM: Pantoea stewartii

<400> SEQUENCE: 32

| | | | | | | | | | | | | | | |
|---|---|---|---|---|---|---|---|---|---|---|---|---|---|---|
| Met | Lys | Pro | Thr | Thr | Val | Ile | Gly | Ala | Gly | Phe | Gly | Gly | Leu | Ala | Leu |
| 1 | | | | 5 | | | | | 10 | | | | | 15 | |
| Ala | Ile | Arg | Leu | Gln | Ala | Ala | Gly | Ile | Pro | Val | Leu | Leu | Leu | Glu | Gln |
| | | | 20 | | | | | 25 | | | | | 30 | | |
| Arg | Asp | Lys | Pro | Gly | Gly | Arg | Ala | Tyr | Val | Tyr | Gln | Glu | Gln | Gly | Phe |
| | | 35 | | | | | 40 | | | | | 45 | | | |
| Thr | Phe | Asp | Ala | Gly | Pro | Thr | Val | Ile | Thr | Asp | Pro | Ser | Ala | Ile | Glu |
| | | 50 | | | | | 55 | | | | | 60 | | | |
| Glu | Leu | Phe | Ala | Leu | Ala | Gly | Lys | Gln | Leu | Lys | Asp | Tyr | Val | Glu | Leu |
| 65 | | | | | 70 | | | | | 75 | | | | | 80 |
| Leu | Pro | Val | Thr | Pro | Phe | Tyr | Arg | Leu | Cys | Trp | Glu | Ser | Gly | Lys | Val |
| | | | | 85 | | | | | 90 | | | | | 95 | |
| Phe | Asn | Tyr | Asp | Asn | Asp | Gln | Ala | Gln | Leu | Glu | Ala | Gln | Ile | Gln | Gln |
| | | | 100 | | | | | 105 | | | | | 110 | | |
| Phe | Asn | Pro | Arg | Asp | Val | Ala | Gly | Tyr | Arg | Ala | Phe | Leu | Asp | Tyr | Ser |
| | | | 115 | | | | | 120 | | | | | 125 | | |

```
Arg Ala Val Phe Asn Glu Gly Tyr Leu Lys Leu Gly Thr Val Pro Phe
        130                 135                 140

Leu Ser Phe Lys Asp Met Leu Arg Ala Ala Pro Gln Leu Ala Lys Leu
145                 150                 155                 160

Gln Ala Trp Arg Ser Val Tyr Ser Lys Val Ala Gly Tyr Ile Glu Asp
                165                 170                 175

Glu His Leu Arg Gln Ala Phe Ser Phe His Ser Leu Leu Val Gly Gly
                180                 185                 190

Asn Pro Phe Ala Thr Ser Ser Ile Tyr Thr Leu Ile His Ala Leu Glu
                195                 200                 205

Arg Glu Trp Gly Val Trp Phe Pro Arg Gly Gly Thr Gly Ala Leu Val
        210                 215                 220

Asn Gly Met Ile Lys Leu Phe Gln Asp Leu Gly Gly Glu Val Val Leu
225                 230                 235                 240

Asn Ala Arg Val Ser His Met Glu Thr Val Gly Asp Lys Ile Gln Ala
                245                 250                 255

Val Gln Leu Glu Asp Gly Arg Arg Phe Glu Thr Cys Ala Val Ala Ser
                260                 265                 270

Asn Ala Asp Val Val His Thr Tyr Arg Asp Leu Leu Ser Gln His Pro
                275                 280                 285

Ala Ala Ala Lys Gln Ala Lys Lys Leu Gln Ser Lys Arg Met Ser Asn
        290                 295                 300

Ser Leu Phe Val Leu Tyr Phe Gly Leu Asn His His Asp Gln Leu
305                 310                 315                 320

Ala His His Thr Val Cys Phe Gly Pro Arg Tyr Arg Glu Leu Ile His
                325                 330                 335

Glu Ile Phe Asn His Asp Gly Leu Ala Glu Asp Phe Ser Leu Tyr Leu
                340                 345                 350

His Ala Pro Cys Val Thr Asp Pro Ser Leu Ala Pro Glu Gly Cys Gly
                355                 360                 365

Ser Tyr Tyr Val Leu Ala Pro Val Pro His Leu Gly Thr Ala Asn Leu
        370                 375                 380

Asp Trp Ala Val Glu Gly Pro Arg Leu Arg Asp Arg Ile Phe Asp Tyr
385                 390                 395                 400

Leu Glu Gln His Tyr Met Pro Gly Leu Arg Ser Gln Leu Val Thr His
                405                 410                 415

Arg Met Phe Thr Pro Phe Asp Phe Arg Asp Glu Leu Asn Ala Trp Gln
                420                 425                 430

Gly Ser Ala Phe Ser Val Glu Pro Ile Leu Thr Gln Ser Ala Trp Phe
        435                 440                 445

Arg Pro His Asn Arg Asp Lys His Ile Asp Asn Leu Tyr Leu Val Gly
        450                 455                 460

Ala Gly Thr His Pro Gly Ala Gly Ile Pro Gly Val Ile Gly Ser Ala
465                 470                 475                 480

Lys Ala Thr Ala Gly Leu Met Leu Glu Asp Leu Ile
                485                 490

<210> SEQ ID NO 33
<211> LENGTH: 891
<212> TYPE: DNA
<213> ORGANISM: Pantoea stewartii

<400> SEQUENCE: 33
atggcggttg gctcgaaaag ctttgcgact gcatcgacgc ttttcgacgc caaaacccgt    60
```

```
cgcagcgtgc tgatgcttta cgcatggtgc cgccactgcg acgacgtcat tgacgatcaa    120
acactgggct tcatgccga  ccagccctct tcgcagatgc tgagcagcg  cctgcagcag    180
cttgaaatga aaacgcgtca ggcctacgcc ggttcgcaaa tgcacgagcc cgcttttgcc    240
gcgtttcagg aggtcgcgat ggcgcatgat atcgctcccg cctacgcgtt cgaccatctg    300
gaaggttttg ccatggatgt gcgcgaaacg cgctacctga cactggacga tacgctgcgt    360
tattgctatc acgtcgccgg tgttgtgggc ctgatgatgg cgcaaattat gggcgttcgc    420
gataacgcca cgctcgatcg cgcctgcgat ctcgggctgg ctttccagtt gaccaacatt    480
gcgcgtgata ttgtcgacga tgctcaggtg ggccgctgtt atctgcctga agctggctg    540
gaagaggaag gactgacgaa agcgaattat gctgcgccag aaaaccggca ggccttaagc    600
cgtatcgccg gcgactggt  acgggaagcg gaaccctatt acgtatcatc aatgccggt    660
ctggcacaat taccctttacg ctcggcctgg gccatcgcga cagcgaagca ggtgtaccgt    720
aaaattggcg tgaaagttga acaggccggt aagcaggcct gggatcatcg ccagtccacg    780
tccaccgccg aaaaattaac gcttttgctg acggcatccg gtcaggcagt tacttcccgg    840
atgaagacgt atccaccccg tcctgctcat ctctggcagc gcccgatcta g            891
```

<210> SEQ ID NO 34
<211> LENGTH: 296
<212> TYPE: PRT
<213> ORGANISM: Pantoea stewartii

<400> SEQUENCE: 34

```
Met Ala Val Gly Ser Lys Ser Phe Ala Thr Ala Ser Thr Leu Phe Asp
  1               5                  10                  15

Ala Lys Thr Arg Arg Ser Val Leu Met Leu Tyr Ala Trp Cys Arg His
                 20                  25                  30

Cys Asp Asp Val Ile Asp Asp Gln Thr Leu Gly Phe His Ala Asp Gln
             35                  40                  45

Pro Ser Ser Gln Met Pro Glu Gln Arg Leu Gln Gln Leu Glu Met Lys
         50                  55                  60

Thr Arg Gln Ala Tyr Ala Gly Ser Gln Met His Glu Pro Ala Phe Ala
 65                  70                  75                  80

Ala Phe Gln Glu Val Ala Met Ala His Asp Ile Ala Pro Ala Tyr Ala
                 85                  90                  95

Phe Asp His Leu Glu Gly Phe Ala Met Asp Val Arg Glu Thr Arg Tyr
                100                 105                 110

Leu Thr Leu Asp Asp Thr Leu Arg Tyr Cys Tyr His Val Ala Gly Val
            115                 120                 125

Val Gly Leu Met Met Ala Gln Ile Met Gly Val Arg Asp Asn Ala Thr
        130                 135                 140

Leu Asp Arg Ala Cys Asp Leu Gly Leu Ala Phe Gln Leu Thr Asn Ile
145                 150                 155                 160

Ala Arg Asp Ile Val Asp Asp Ala Gln Val Gly Arg Cys Tyr Leu Pro
                165                 170                 175

Glu Ser Trp Leu Glu Glu Gly Leu Thr Lys Ala Asn Tyr Ala Ala
                180                 185                 190

Pro Glu Asn Arg Gln Ala Leu Ser Arg Ile Ala Gly Arg Leu Val Arg
            195                 200                 205

Glu Ala Glu Pro Tyr Tyr Val Ser Ser Met Ala Gly Leu Ala Gln Leu
        210                 215                 220

Pro Leu Arg Ser Ala Trp Ala Ile Ala Thr Ala Lys Gln Val Tyr Arg
```

```
                225                 230                 235                 240
Lys Ile Gly Val Lys Val Glu Gln Ala Gly Lys Gln Ala Trp Asp His
                    245                 250                 255

Arg Gln Ser Thr Ser Thr Ala Glu Lys Leu Thr Leu Leu Thr Ala
            260                 265                 270

Ser Gly Gln Ala Val Thr Ser Arg Met Lys Thr Tyr Pro Pro Arg Pro
        275                 280                 285

Ala His Leu Trp Gln Arg Pro Ile
    290                 295

<210> SEQ ID NO 35
<211> LENGTH: 528
<212> TYPE: DNA
<213> ORGANISM: Pantoea stewartii

<400> SEQUENCE: 35
atgttgtgga tttggaatgc cctgatcgtg tttgtcaccg tggtcggcat ggaagtggtt      60
gctgcactgg cacataaata tcatcatgcac ggctggggtt ggggctggca tcttcacat    120 catgaaccgc gtaaaggcgc atttgaagtt aacgatctct atgccgtggt attcgccatt    180
gtgtcgattg ccctgattta cttcggcagt acaggaatct ggccgctcca gtggattggt    240
gcaggcatga ccgcttatgg tttactgtat tttatggtcc acgacggact ggtacaccag    300
cgctggccgt tccgctacat accgcgcaaa ggctacctga acggttata catggcccac     360 cgtatgcatc atgctgtaag gggaaaagag ggctgcgtgt cctttggttt tctgtacgcg    420
ccaccgttat ctaaacttca ggcgacgctg agagaaaggc atgcggctag atcgggcgct    480
gccagagatg agcaggacgg ggtggatacg tcttcatccg ggaagtaa                 528

<210> SEQ ID NO 36
<211> LENGTH: 175
<212> TYPE: PRT
<213> ORGANISM: Pantoea stewartii

<400> SEQUENCE: 36

Met Leu Trp Ile Trp Asn Ala Leu Ile Val Phe Val Thr Val Val Gly
1               5                   10                  15

Met Glu Val Val Ala Ala Leu Ala His Lys Tyr Ile Met His Gly Trp
            20                  25                  30

Gly Trp Gly Trp His Leu Ser His His Glu Pro Arg Lys Gly Ala Phe
        35                  40                  45

Glu Val Asn Asp Leu Tyr Ala Val Val Phe Ala Ile Val Ser Ile Ala
    50                  55                  60

Leu Ile Tyr Phe Gly Ser Thr Gly Ile Trp Pro Leu Gln Trp Ile Gly
65                  70                  75                  80

Ala Gly Met Thr Ala Tyr Gly Leu Leu Tyr Phe Met Val His Asp Gly
                85                  90                  95

Leu Val His Gln Arg Trp Pro Phe Arg Tyr Ile Pro Arg Lys Gly Tyr
            100                 105                 110

Leu Lys Arg Leu Tyr Met Ala His Arg Met His Ala Val Arg Gly
            115                 120                 125

Lys Glu Gly Cys Val Ser Phe Gly Phe Leu Tyr Ala Pro Pro Leu Ser
        130                 135                 140

Lys Leu Gln Ala Thr Leu Arg Glu Arg His Ala Ala Arg Ser Gly Ala
145                 150                 155                 160

Ala Arg Asp Glu Gln Asp Gly Val Asp Thr Ser Ser Ser Gly Lys
```

<210> SEQ ID NO 37
<211> LENGTH: 1599
<212> TYPE: DNA
<213> ORGANISM: Rhodococcus erythropolis AN12

<400> SEQUENCE: 37

| | | | | | |
|---|---|---|---|---|---|
| gtgagcgcat | ttctcgacgc | cgtcgtcgtc | ggttccggac | acaacgcgct | cgtttcggcc | 60 |
| gcgtatctcg | cacgtgaggg | ttggtcggtc | gaggttctcg | agaaggacac | ggttctcggc | 120 |
| ggtgccgtct | cgaccgtcga | gcgatttccc | ggatacaagg | tggaccgggg | gtcgtctgcg | 180 |
| cacctcatga | tccgacacag | tggcatcatc | gaggaactcg | gactcggcgc | gcacggcctt | 240 |
| cgctacatcg | actgtgaccc | gtgggcgttc | gctccgcccg | ccctggcac | cgacgggccg | 300 |
| ggcatcgtgt | tcatcgcga | cctcgatgca | acctgccagt | ccatcgaacg | agcttgcggg | 360 |
| acaaaggacg | ccgacgcgta | ccggcggttc | gtcgcggtct | ggtcggagcg | cagccgacac | 420 |
| gtgatgaagg | cattttccac | accgcccacc | ggatcgaacc | tgatcggtgc | gttcggagga | 480 |
| ctggccacag | cgcgcggcaa | cagcgaactg | tcgcggcagt | tcctcgcgcc | gggcgacgca | 540 |
| ctgctggacg | agtatttcga | cagtgaggca | ctcaaggcag | cgttggcgtg | gttcggcgcc | 600 |
| cagtccgggc | ctccgatgtc | ggaaccggga | accgctccga | tggtcggctt | cgcggccctc | 660 |
| atgcacgtcc | tgccgcccgg | gcgagcagtc | ggagggagcg | gcgcactgag | tgctgcgttg | 720 |
| gcatcccgga | tggctgtcga | cggcgccacc | gtcgcgctcg | gtgacggcgt | gacgtcgatc | 780 |
| cgccggaact | cgaatcactg | gaccgtcaca | accgagagcg | gtcgagaagt | tcacgctcgc | 840 |
| aaggtaatcg | cgggttgcca | catcctcacg | acactcgatc | tcctgggcaa | cggaggcttc | 900 |
| gaccgaacca | cgctcgatca | ctggcggcgg | aagatcaggg | tcggcccggg | catcggcgct | 960 |
| gtattgcgac | tggcgacatc | tgcgctcccg | tcctaccgcg | gcgacgccac | gacacgggaa | 1020 |
| agtacctcgg | gattgcaatt | actcgttttcc | gatcgcgccc | acttgcgcac | tgcacacggc | 1080 |
| gcagcactgg | cagggaact | gcctcctcgc | cctgcggttc | tcggaatgag | tttcagcgga | 1140 |
| atcgatccca | cgatcgcccc | ggccgggcgg | catcaggtga | cactgtggtc | gcagtggcag | 1200 |
| ccgtatcgtc | tcagcggaca | tcgcgattgg | gcgtcggtcg | ccgaggccga | ggccgaccgg | 1260 |
| atcgtcggcg | agatggaggc | ttttgcaccc | ggattcaccg | attccgtcct | cgaccgcttc | 1320 |
| attcaaactc | cccgcgacat | cgagtcggaa | ttggggatga | tcggcggaaa | tgtcatgcac | 1380 |
| gtcgagatgt | cactcgatca | gatgatgttg | tggcgaccgc | ttcccgaact | gtccggccat | 1440 |
| cgcgttccgg | gagcagacgg | gttgtatctg | accggagcct | cgacgcatcc | cggtggtggt | 1500 |
| gtgtccggag | ccagtggtcg | cagtgccgct | cgaatcgcac | tgtccgacag | ccgccggggt | 1560 |
| aaagcgagtc | agtggatgcg | tcgttcgagc | aggtcgtga | | | 1599 |

<210> SEQ ID NO 38
<211> LENGTH: 532
<212> TYPE: PRT
<213> ORGANISM: Rhodococcus erythropolis AN12

<400> SEQUENCE: 38

Met Ser Ala Phe Leu Asp Ala Val Val Val Gly Ser Gly His Asn Ala
1               5                   10                  15

Leu Val Ser Ala Ala Tyr Leu Ala Arg Glu Gly Trp Ser Val Glu Val
            20                  25                  30

Leu Glu Lys Asp Thr Val Leu Gly Gly Ala Val Ser Thr Val Glu Arg

```
              35                  40                  45
Phe Pro Gly Tyr Lys Val Asp Arg Gly Ser Ser Ala His Leu Met Ile
 50                  55                  60

Arg His Ser Gly Ile Ile Glu Glu Leu Gly Leu Gly Ala His Gly Leu
 65                  70                  75                  80

Arg Tyr Ile Asp Cys Asp Pro Trp Ala Phe Ala Pro Ala Pro Gly
                 85                  90                  95

Thr Asp Gly Pro Gly Ile Val Phe His Arg Asp Leu Asp Ala Thr Cys
                100                 105                 110

Gln Ser Ile Glu Arg Ala Cys Gly Thr Lys Asp Ala Asp Ala Tyr Arg
            115                 120                 125

Arg Phe Val Ala Val Trp Ser Glu Arg Ser Arg His Val Met Lys Ala
130                 135                 140

Phe Ser Thr Pro Pro Thr Gly Ser Asn Leu Ile Gly Ala Phe Gly Gly
145                 150                 155                 160

Leu Ala Thr Ala Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
            180                 185                 190

Ala Ala Leu Ala Trp Phe Gly Ala Gln Ser Gly Pro Pro Met Ser Glu
        195                 200                 205

Pro Gly Thr Ala Pro Met Val Gly Phe Ala Ala Leu Met His Val Leu
    210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
                245                 250                 255

Val Thr Ser Ile Arg Arg Asn Ser Asn His Trp Thr Val Thr Thr Glu
            260                 265                 270

Ser Gly Arg Glu Val His Ala Arg Lys Val Ile Ala Gly Cys His Ile
        275                 280                 285

Leu Thr Thr Leu Asp Leu Leu Gly Asn Gly Gly Phe Asp Arg Thr Thr
    290                 295                 300

Leu Asp His Trp Arg Arg Lys Ile Arg Val Gly Pro Gly Ile Gly Ala
305                 310                 315                 320

Val Leu Arg Leu Ala Thr Ser Ala Leu Pro Ser Tyr Arg Gly Asp Ala
                325                 330                 335

Thr Thr Arg Glu Ser Thr Ser Gly Leu Gln Leu Leu Val Ser Asp Arg
            340                 345                 350

Ala His Leu Arg Thr Ala His Gly Ala Ala Leu Ala Gly Glu Leu Pro
        355                 360                 365

Pro Arg Pro Ala Val Leu Gly Met Ser Phe Ser Gly Ile Asp Pro Thr
    370                 375                 380

Ile Ala Pro Ala Gly Arg His Gln Val Thr Leu Trp Ser Gln Trp Gln
385                 390                 395                 400

Pro Tyr Arg Leu Ser Gly His Arg Asp Trp Ala Ser Val Ala Glu Ala
                405                 410                 415

Glu Ala Asp Arg Ile Val Gly Glu Met Glu Ala Phe Ala Pro Gly Phe
            420                 425                 430

Thr Asp Ser Val Leu Asp Arg Phe Ile Gln Thr Pro Arg Asp Ile Glu
        435                 440                 445

Ser Glu Leu Gly Met Ile Gly Gly Asn Val Met His Val Glu Met Ser
    450                 455                 460
```

```
Leu Asp Gln Met Met Leu Trp Arg Pro Leu Pro Glu Leu Ser Gly His
465                 470                 475                 480

Arg Val Pro Gly Ala Asp Gly Leu Tyr Leu Thr Gly Ala Ser Thr His
                485                 490                 495

Pro Gly Gly Gly Val Ser Gly Ala Ser Gly Arg Ser Ala Ala Arg Ile
            500                 505                 510

Ala Leu Ser Asp Ser Arg Arg Gly Lys Ala Ser Gln Trp Met Arg Arg
            515                 520                 525

Ser Ser Arg Ser
    530
```

<210> SEQ ID NO 39
<211> LENGTH: 30
<212> TYPE: DNA
<213> ORGANISM: Methylomonas 16a

<400> SEQUENCE: 39
ccgagtactg aagcgggttt ttgcagggag                                    30

<210> SEQ ID NO 40
<211> LENGTH: 25
<212> TYPE: DNA
<213> ORGANISM: Methylomonas 16a

<400> SEQUENCE: 40
gggctagctg ctccgattgt tacag                                         25

<210> SEQ ID NO 41
<211> LENGTH: 38
<212> TYPE: DNA
<213> ORGANISM: Artificial Sequence
<220> FEATURE:
<223> OTHER INFORMATION: primer, derived from Rhodococcus erythropolis
      AN12

<400> SEQUENCE: 41
agcagctagc ggaggaataa accatgagcg catttctc                           38

<210> SEQ ID NO 42
<211> LENGTH: 26
<212> TYPE: DNA
<213> ORGANISM: Artificial Sequence
<220> FEATURE:
<223> OTHER INFORMATION: primer, derived from Rhodococcus erythropolis
      AN12

<400> SEQUENCE: 42
gactagtcac gacctgctcg aacgac                                        26

<210> SEQ ID NO 43
<211> LENGTH: 25
<212> TYPE: DNA
<213> ORGANISM: Artificial Sequence
<220> FEATURE:
<223> OTHER INFORMATION: primer

<400> SEQUENCE: 43
atgacggtct gcgcaaaaaa acacg                                         25

<210> SEQ ID NO 44
<211> LENGTH: 28
<212> TYPE: DNA
<213> ORGANISM: Artificial Sequence

```
<220> FEATURE:
<223> OTHER INFORMATION: primer

<400> SEQUENCE: 44
gagaaattat gttgtggatt tggaatgc                                              28

<210> SEQ ID NO 45
<211> LENGTH: 19
<212> TYPE: DNA
<213> ORGANISM: Artificial Sequence
<220> FEATURE:
<223> OTHER INFORMATION: primer

<400> SEQUENCE: 45
gagtttgatc ctggctcag                                                        19

<210> SEQ ID NO 46
<211> LENGTH: 16
<212> TYPE: DNA
<213> ORGANISM: Artificial Sequence
<220> FEATURE:
<223> OTHER INFORMATION: primer

<400> SEQUENCE: 46
taccttgtta cgactt                                                           16

<210> SEQ ID NO 47
<211> LENGTH: 17
<212> TYPE: DNA
<213> ORGANISM: Artificial Sequence
<220> FEATURE:
<223> OTHER INFORMATION: primer
<221> NAME/KEY: misc_feature
<222> LOCATION: (11)..(11)
<223> OTHER INFORMATION: Y = C or T
<221> NAME/KEY: misc_feature
<222> LOCATION: (12)..(12)
<223> OTHER INFORMATION: M = A or C

<400> SEQUENCE: 47
gtgccagcag ymgcggt                                                          17

<210> SEQ ID NO 48
<211> LENGTH: 21
<212> TYPE: DNA
<213> ORGANISM: Artificial Sequence
<220> FEATURE:
<223> OTHER INFORMATION: primer

<400> SEQUENCE: 48
atgagcgcat ttctcgacgc c                                                     21

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
tcacgacctg ctcgaacgac                                                       20

<210> SEQ ID NO 50
<211> LENGTH: 50
<212> TYPE: DNA
<213> ORGANISM: Artificial Sequence
<220> FEATURE:
```

```
<223> OTHER INFORMATION: primer

<400> SEQUENCE: 50
gagaattggc tgaaaaacca aataaataac aaaatttagc gagtaaatgg         50

<210> SEQ ID NO 51
<211> LENGTH: 50
<212> TYPE: DNA
<213> ORGANISM: Artificial Sequence
<220> FEATURE:
<223> OTHER INFORMATION: primer

<400> SEQUENCE: 51
ttcaattgac aggggggctc gttctgattt agagttgctg ccagcttttt         50

<210> SEQ ID NO 52
<211> LENGTH: 50
<212> TYPE: DNA
<213> ORGANISM: Artificial Sequence
<220> FEATURE:
<223> OTHER INFORMATION: primer

<400> SEQUENCE: 52
gggttgtcca gatgttggtg agcggtcctt ataactataa ctgtaacaat         50

<210> SEQ ID NO 53
<211> LENGTH: 50
<212> TYPE: DNA
<213> ORGANISM: Artificial Sequence
<220> FEATURE:
<223> OTHER INFORMATION: primer

<400> SEQUENCE: 53
ttaatggtct tgccatgaga tgtgctccga ttgttacagt tatagttata         50

<210> SEQ ID NO 54
<211> LENGTH: 50
<212> TYPE: DNA
<213> ORGANISM: Artificial Sequence
<220> FEATURE:
<223> OTHER INFORMATION: primer

<400> SEQUENCE: 54 cccctgtca attgaaagcc cgccatttac tcgctaaatt ttgttattta          50

<210> SEQ ID NO 55
<211> LENGTH: 22
<212> TYPE: DNA
<213> ORGANISM: Artificial Sequence
<220> FEATURE:
<223> OTHER INFORMATION: primer

<400> SEQUENCE: 55
aaggatccgc gtattcgtac tc                                      22

<210> SEQ ID NO 56
<211> LENGTH: 40
<212> TYPE: DNA
<213> ORGANISM: Artificial Sequence
<220> FEATURE:
<223> OTHER INFORMATION: primer

<400> SEQUENCE: 56
ctggatccga tctagaaata ggctcgagtt gtcgttcagg                    40
```

-continued

```
<210> SEQ ID NO 57
<211> LENGTH: 30
<212> TYPE: DNA
<213> ORGANISM: Artificial Sequence
<220> FEATURE:
<223> OTHER INFORMATION: primer

<400> SEQUENCE: 57
aaggatccta ctcgagctga catcagtgct                                    30

<210> SEQ ID NO 58
<211> LENGTH: 22
<212> TYPE: DNA
<213> ORGANISM: Artificial Sequence
<220> FEATURE:
<223> OTHER INFORMATION: primer

<400> SEQUENCE: 58
gctctagatg caaccagaat cg                                            22

<210> SEQ ID NO 59
<211> LENGTH: 24
<212> TYPE: DNA
<213> ORGANISM: Artificial Sequence
<220> FEATURE:
<223> OTHER INFORMATION: primer

<400> SEQUENCE: 59
tggctcgaga gtaaaacact caag                                          24

<210> SEQ ID NO 60
<211> LENGTH: 19
<212> TYPE: DNA
<213> ORGANISM: Artificial Sequence
<220> FEATURE:
<223> OTHER INFORMATION: primer

<400> SEQUENCE: 60
tagctcgagt cacgcttgc                                                19
```

CAROTENOID PRODUCTION FROM A SINGLE CARBON SUBSTRATE

This application claims the benefit of U.S. Provisional Application No. 60/229,907, filed Sep. 1, 2000 and the benefit of U.S. Provisional Application No. 60/229,858 filed Sep. 1, 2000.

FIELD OF THE INVENTION

The invention relates to the field of molecular biology and microbiology. More specifically, the invention describes the production of carotenoid compounds from microorganisms which metabolize single carbon substrates as a sole carbon source.

BACKGROUND OF THE INVENTION

Carotenoids represent one of the most widely distributed and structurally diverse classes of natural pigments, producing pigment colors of light yellow to orange to deep red. Eye-catching examples of carotenogenic tissues include carrots, tomatoes, red peppers, and the petals of daffodils and marigolds. Carotenoids are synthesized by all photosynthetic organisms, as well as some bacteria and fungi. These pigments have important functions in photosynthesis, nutrition, and protection against photooxidative damage. For example, animals do not have the ability to synthesize carotenoids but must instead obtain these nutritionally important compounds through their dietary sources. Structurally, carotenoids are 40-carbon ($C_{40}$) terpenoids derived from the isoprene biosynthetic pathway and its five-carbon universal isoprene building block, isopentenyl pyrophosphate (IPP). This biosynthetic pathway can be divided into two portions: the upper isoprene pathway, which leads to the formation of IPP, and the lower carotenoid biosynthetic pathway, which converts IPP into long $C_{30}$ and $C_{40}$ carotenogenic compounds. Both portions of this pathway are shown in FIG. 1.

Various other crt genes are known, which enable the intramolecular conversion of long $C_{30}$ and $C_{40}$ compounds to produce numerous other carotenoid compounds. It is the degree of the carbon backbone's unsaturation, conjugation and isomerization which determines the specific carotenoids unique absorption characteristics and colors. Several reviews discuss the genetics of carotenoid pigment biosynthesis, such as those of Armstrong (*J. Bact.* 176: 4795–4802 (1994); *Annu. Rev. Microbiol.* 51:629–659 (1997)).

In reference to the availability of carotenoid genes, public domain databases such as GenBank contain sequences isolated from numerous organisms. For example, there are currently 26 GenBank Accession numbers relating to various crtE genes isolated from 19 different organisms. The less frequently encountered crtZ gene boasts 6 GenBank Accession numbers with each gene isolated from a different organism. A similarly wide selection of carotenoid genes is available for each of the genes discussed above.

The genetics of carotenoid pigment biosynthesis has been extremely well studied in the Gram-negative, pigmented bacteria of the genera *Pantoea*, formerly known as *Erwinia*. In both *E. herbicola* EHO-10 (ATCC 39368) and *E. uredovora* 20D3 (ATCC 19321), the crt genes are clustered in two genetic units, crt Z and crt EXYIB (U.S. Pat. Nos. 5,656,472; 5,5545,816; 5,530,189; 5,530,188; 5,429,939). Despite the similarity in operon structure, the DNA sequences of *E. uredovora* and *E. herbicola* show no homology by DNA-DNA hybridization (U.S. Pat. No. 5,429,939).

Although more than 600 different carotenoids have been identified in nature, only a few are used industrially for food colors, animal feeding, pharmaceuticals and cosmetics. Presently, most of the carotenoids used for industrial purposes are produced by chemical synthesis; however, these compounds are very difficult to make chemically (Nelis and Leenheer, *Appl. Bacteriol.* 70:181–191 (1991)). Natural carotenoids can either be obtained by extraction of plant material or by microbial synthesis. At the present time, only a few plants are widely used for commercial carotenoid production. However, the productivity of carotenoid synthesis in these plants is relatively low and the resulting carotenoids are very expensive.

A number of carotenoids have been produced from microbial sources. For example, Lycopene has been produced from genetically engineered *E. coli* and *Candia utilis* (Farmer W. R. and J. C. Liao. (2001) *Biotechnol. Prog.* 17: 57–61; Wang C. et al., (2000) *Biotechnol Prog.* 16: 922–926; Misawa, N. and H. Shimada. (1998). *J. Biotechnol.* 59:169–181; Shimada, H. et al. 1998. *Appl. Environm. Microbiol.* 64:2676–2680). β-carotene has been produced from *E. coli, Candia utilis* and *Pfaffia rhodozyma* (Albrecht, M. et al., (1999). *Biotechnol. Lett.* 21: 791–795; Miura, Y. et al., 1998. *Appl. Environm. Microbiol.* 64:1226–1229; U.S. Pat. No. 5,691,190). Zeaxanthin has been produced from recombinant from *E. coli* and *Candia utilis* (Albrecht, M. et al., (1999). *Biotechnol. Lett.* 21: 791–795; Miura, Y. et al., 1998. *Appl. Environm. Microbiol.* 64:1226–1229). Astaxanthin has been produced from *E. coli* and *Pfaffia rhodozyma* (U.S. Pat. Nos. 5,466,599; 6,015,684; 5,182,208; 5,972,642).

Additionally genes encoding various elements of the carotenoid biosynthetic pathway have been cloned and expressed in various microbes. For example genes encoding lycopene cyclase, geranylgeranyl pyrophosphate synthase, and phytoene dehydrogenase isolated from *Erwinia herbicola* have been expressed recombinantly in *E. coli* (U.S. Pat. Nos. 5,656,472; 5,545,816; 5,530,189; 5,530,188). Similarly genes encoding the carotenoid products geranylgeranyl pyrophosphate, phytoene, lycopene, β-carotene, and zeaxanthin-diglucoside, isolated from *Erwinia uredovora* have been expressed in *E. coli, Zymomonas mobilis*, and *Saccharomyces cerevisiae* (U.S. Pat. No. 5,429,939). Similarly, the Carotenoid biosynthetic genes crtE (1), crtB (3), crtI (5), crtY (7), and crtZ isolated from *Flavobacterium* have been recombinantly expressed (U.S. Pat. No. 6,124,113).

Although the above methods of propducing carotenoids are useful, these methods suffer from low yields and reliance on expensive feedstock's. A method that produces higher yields of carotenoids from an inexpensive feedstock is needed.

There are a number of microorganisms that utilize single carbon substrates as sole energy sources. These substrates include, methane, methanol, formate, methylated amines and thiols, and various other reduced carbon compounds which lack any carbon-carbon bonds and are generally quite inexpensive. These organisms are referred to as methylotrophs and herein as "C1 metabolizers". These organisms are characterized by the ability to use carbon substrates lacking carbon to carbon bonds as a sole source of energy and biomass. A subset of methylotrophs are the methanotrophs which have the unique ability to utilize methane as a sole energy source. Although a large number of these organisms are known, few of these microbes have been successfully harnessed to industrial processes for the synthesis of materials. Although single carbon substrates are cost effective energy sources, difficulty in genetic manipulation of these microorganisms as well as a dearth of information about their genetic machinery has limited their use primarily to the synthesis of native products. For example the commercial applications of biotransformation of methane have historically fallen broadly into three categories: 1) Production of single cell protein, (Sharpe D. H. BioProtein Manufacture 1989. Ellis Horwood series in applied science and industrial technology. New York: Halstead Press.) (Villadsen, John, *Recent Trends Chem. React. Eng.*, [Proc. Int. Chem. React. Eng. Conf.], 2nd (1987), Volume 2, 320–33. Editor(s): Kulkarni, B. D.; Mashelkar, R. A.; Sharma, M. M. Publisher: Wiley East., New Delhi, India; Naguib, M., Proc. OAPEC Symp. Petroprotein, [Pap.] (1980), Meeting Date 1979, 253–77 Publisher: Organ. Arab Pet. Exporting Countries, Kuwait, Kuwait.); 2) epoxidation of alkenes for production of chemicals (U.S. Pat. No. 4,348,476); and 3) biodegradation of chlorinated pollutants (Tsien et al., *Gas, Oil, Coal, Environ. Biotechnol.* 2, [Pap. Int. IGT Symp. *Gas, Oil, Coal, Environ. Biotechnol.*], 2nd (1990), 83–104. Editor(s): Akin, Cavit; Smith, Jared. Publisher: Inst. Gas Technol., Chicago, Ill.; WO 9633821; Merkley et al., *Biorem. Recalcitrant Org.*, [Pap. Int. In Situ On-Site Bioreclam. Symp.], 3rd (1995), 165–74. Editor(s): Hinchee, Robert E; Anderson, Daniel B.; Hoeppel, Ronald E. Publisher: Battelle Press, Columbus, Ohio.: Meyer et al., *Microb. Releases* (1993), 2(1), 11–22). Even here, the commercial success of the methane biotransformation has been limited to epoxidation of alkenes due to low product yields, toxicity of products and the large amount of cell mass required to generate product associated with the process.

The commercial utility of methylotrophic organisms is reviewed in Lidstrom and Stirling (Annu. Rev. Microbiol. 44:27–58 (1990)). Little commercial success has been documented, despite numerous efforts involving the application of methylotrophic organisms and their enzymes (Lidstrom and Stirling, supra, Table 3). In most cases, it has been discovered that the organisms have little advantage over other well-developed host systems. Methanol is frequently cited as a feedstock which should provide both economic and quality advantages over other more traditional carbohydrate raw materials, but thus far this expectation has not been significantly validated in published works.

One of the most common classes of single carbon metabolizers are the methanotrophs. Methanotrophic bacteria are defined by their ability to use methane as a sole source of carbon and energy. Methane monooxygenase is the enzyme required for the primary step in methane activation and the product of this reaction is methanol (Murrell et al., *Arch. Microbiol.* (2000), 173(5–6), 325–332). This reaction occurs at ambient temperature and pressures whereas chemical transformation of methane to methanol requires temperatures of hundreds of degrees and high pressure (Grigoryan, E. A., *Kinet. Catal.* (1999), 40(3), 350–363; WO 2000007718; U.S. Pat. No. 5,750,821). It is this ability to transform methane under ambient conditions along with the abundance of methane that makes the biotransformation of methane a potentially unique and valuable process.

Many methanotrophs contain an inherent isoprenoid pathway which enables these organisms to synthesize other non-endogenous isoprenoid compounds. Since methanotrophs can use one carbon substrate (methane or methanol) as an energy source, it is possible to produce carotenoids at low cost.

Current knowledge in the field concerning methylotrophic organisms and carotenoids leads to the following conclusions. First, there is tremendous commercial incentive arising from abundantly available C1 sources, which could be used as a feedstock for C1 organisms and which should provide both economic and quality advantages over other more traditional carbohydrate raw materials. Secondly, there is abundant knowledge available concerning organisms that possess carotenogenic biosynthetic genes, the function of those genes, and the upper isoprene pathway which produces carotenogenic precursor molecules. Finally, numerous methylotrophic organisms exist in the art which are themselves pigmented, and thereby possess portions of the necessary carotenoid biosynthetic pathway.

Despite these available tools, the art does not reveal any C1 metabolizers which have been genetically engineered to make specific carotenoids of choice, for large scale commercial value. It is hypothesized that the usefulness of these organisms for production of a larger range of chemicals is constrained by limitations including, relatively slow growth rates of methanotrophs, limited ability to tolerate methanol as an alternative substrate to methane, difficulty in genetic engineering, poor understanding of the roles of multiple carbon assimilation pathways present in methanotrophs, and potentially high costs due to the oxygen demand of fully saturated substrates such as methane. The problem to be solved, therefore is to provide a cost effective method for the microbial production of carotenoid compounds, using organisms which utilize C1 compounds as their carbon and energy source.

Applicants have solved the stated problem by engineering microorganisms which are able to use single carbon substrates as sole carbon sources for the production of carotenoid compounds.

SUMMARY OF THE INVENTION

The invention provides a method for the production of a carotenoid compound comprising:
(a) providing a transformed C1 metabolizing host cell comprising:
   (i) suitable levels of isopentenyl pyrophosphate; and
   (ii) at least one isolated nucleic acid molecule encoding an enzyme in the carotenoid biosynthetic pathway under the control of suitable regulatory sequences;
(b) contacting the host cell of step (a) under suitable growth conditions with an effective amount of a C1 carbon substrate whereby an carotenoid compound is produced.

Preferred C1 carbon substrates of the invention are selected from the group consisting of methane, methanol, formaldehyde, formic acid, methylated amines, methylated thiols, and carbon dioxide. Preferred C1 metabolizers are methylotrophs and methanotrophs. Particularly preferred C1 metabolizers are those that comprise a functional Embden-Meyerhof carbon pathway, said pathway comprising a gene encoding a pyrophosphate dependent phosphofructokinase enzyme. Optionally the preferred host may comprise at least one gene encoding a fructose bisphosphate aldolase enzyme.

Suitable levels of isopentenyl pyrophosphate may be endogenous to the host, or may be provided by heterologusly introduced upper pathway isoprenoid genes such as D-1-deoxyxylulose-5-phosphate synthase (Dxs), D-1-deoxyxylulose-5-phosphate reductoisomerase (Dxr), 2C-methyl-d-erythritol cytidylyltransferase (IspD), 4-diphosphocytidyl-2-C-methylerythritol kinase (IspE), 2C-methyl-d-erythritol 2,4-cyclodiphosphate synthase (IspF), CTP synthase (PyrG) and lytB.

In an alternate embodiment the invention provides a method for the over-production of carotenoid production in a transformed C1 metabolizing host comprising:

(a) providing a transformed C1 metabolizing host cell comprising:
   (i) suitable levels of isopentenyl pyrophosphate; and
   (ii) at least one isolated nucleic acid molecule encoding an enzyme in the carotenoid biosynthetic pathway under the control of suitable regulatory sequences; and
   (iii) either:
      1) multiple copies of at least one gene encoding an enzyme selected from the group consisting of D-1-deoxyxylulose-5-phosphate synthase (Dxs), D-1-deoxyxylulose-5-phosphate reductoisomerase (Dxr), 2C-methyl-d-erythritol cytidylyltransferase (IspD), 4-diphosphocytidyl-2-C-methylerythritol kinase (IspE), 2C-methyl-d-erythritol 2,4-cyclodiphosphate synthase (IspF), CTP synthase (PyrG) and lytB; or
      2) at least one gene encoding an enzyme selected from the group consisting of D-1-deoxyxylulose-5-phosphate synthase (Dxs), D-1-deoxyxylulose-5-phosphate reductoisomerase (Dxr), 2C-methyl-d-erythritol cytidylyltransferase (IspD), 4-diphosphocytidyl-2-C-methylerythritol kinase (IspE), 2C-methyl-d-erythritol 2,4-cyclodiphosphate synthase (IspF), CTP synthase (PyrG) and lytB operable linked to a strong promoter.
(b) contacting the host cell of step (a) under suitable growth conditions with an effective amount of a C1 carbon substrate whereby a carotenoid compound is over-produced.

BRIEF DESCRIPTION OF THE DRAWINGS, SEQUENCE DESCRIPTIONS AND BIOLOGICAL DEPOSITS

FIG. 1 illustrates the upper isoprene pathway and lower carotenoid biosynthetic pathway.

FIG. 2 provides microarray expression data for key carbon pathway genes, as expressed in *Methylomonas* 16a.

Figure 1A:
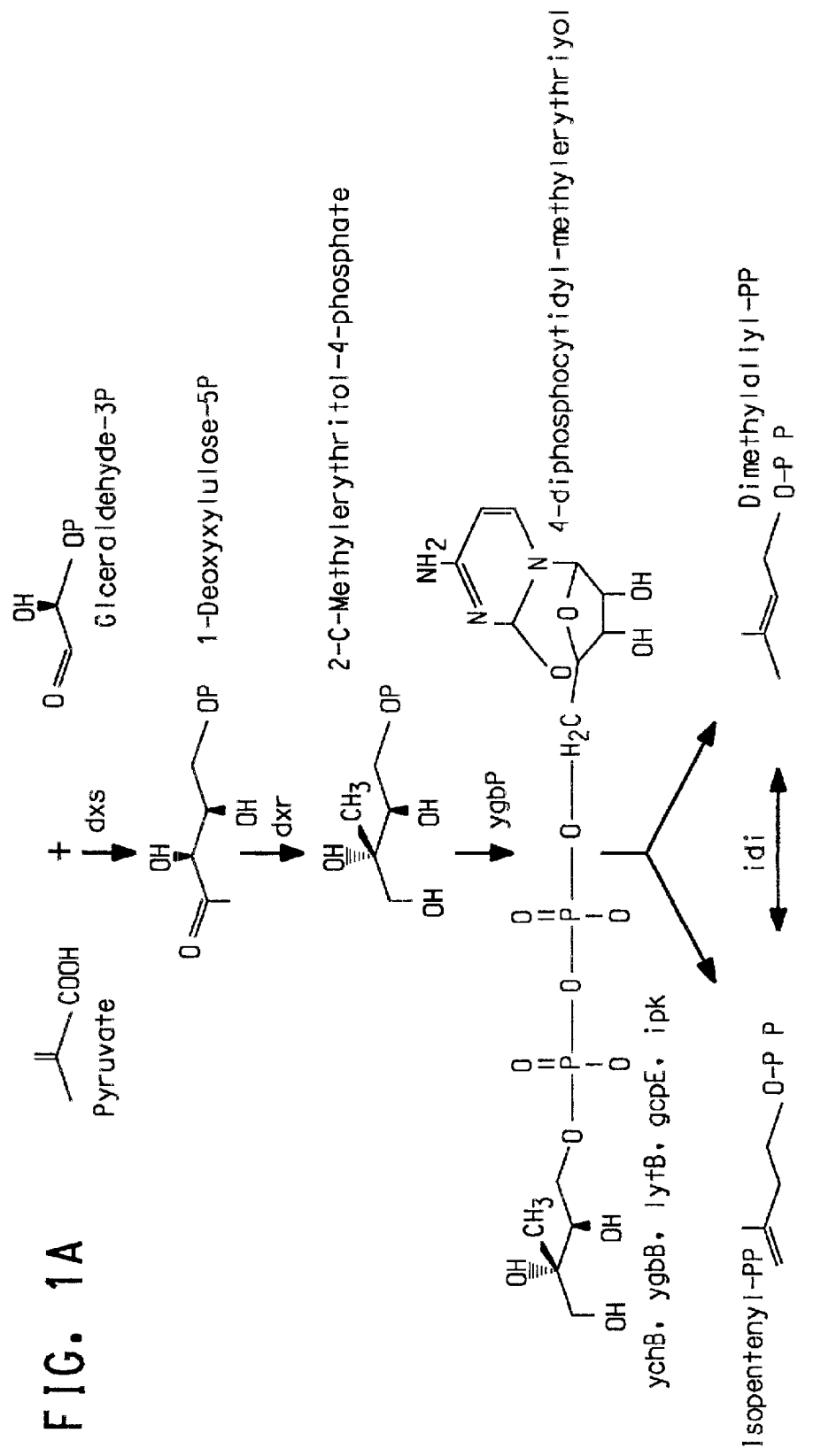

The invention can be more fully understood from the following detailed description and the accompanying sequence descriptions which form a part of this application.

The following sequences conform with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1–38 are full length genes or proteins as identified in Table 1.

TABLE 1

Summary of Gene and Protein SEQ ID Numbers

| Description | SEQ ID Nucleic acid | SEQ ID Peptide |
|---|---|---|
| Phosphofructokinase pyrophosphate dependent | 1 | 2 |
| KHG/KDPG Aldolase | 3 | 4 |
| dxs | 5 | 6 |
| dxr | 7 | 8 |
| ispD (ygbP) | 9 | 10 |
| ispE (ychB) | 11 | 12 |
| ispF (ygbB) | 13 | 14 |
| pyrG | 15 | 16 |
| lytB | 17 | 18 |
| ispA | 19 | 20 |
| CrtN1 | 21 | 22 |
| CrtN2 | 23 | 24 |
| crtE | 25 | 26 |
| crtX | 27 | 28 |
| crtY | 29 | 30 |
| crtI | 31 | 32 |
| crtB | 33 | 34 |
| crtZ | 35 | 36 |
| crtO | 37 | 38 |

SEQ ID Nos:39–40 are amplification primers for the HMPS promoter

SEQ ID Nos:41–42 are amplification primers for the crtO gene from *Rhodococcus*.

SEQ ID NOs:43 and 44 are the primer sequences used to amplify the crt cluster of *Pantoea stewartii*.

SEQ ID NOs:45–47 are the primer sequences used to amplify the 16s rRNA of *Rhodococcus erythropolis* AN 12.

SEQ ID NOs:48 and 49 are the primer sequences used to amplify the crtO gene.

SEQ ID NOs: 50–54 are promoter sequences for the HMPS gene and primers used to amplify that promoter.

SEQ ID NOs:55 and 56 are the primer sequences used to amplify the dxs gene.

SEQ ID NOs:57 and 58 are the primer sequences used to amplify the dxr gene.

SEQ ID NOs:59 and 60 are the primer sequences used to amplify the lytB gene.

Applicants made the following biological deposits under the terms of the Budapest Treaty on the International Recognition of the Deposit of Micro-organisms for the Purposes of Patent Procedure:

| Depositor Identification Reference | International Depository Designation | Date of Deposit |
|---|---|---|
| Methylomonas 16a | ATCC PTA 2402 | August 22, 2000 |

DETAILED DESCRIPTION OF THE INVENTION

The present method is useful for the creation of recombinant organisms that have the ability to produce various carotenoid compounds. Nucleic acid fragments encoding a variety of enzymes implicated in the carotenoid biosynthetic pathway have been cloned into microorganisms which use single carbon substrates as a sole carbon source for the production of carotenoid compounds.

There is a general practical utility for microbial production of carotenoid compounds as these compounds are very difficult to make chemically (Nelis and Leenheer, *Appl. Bacteriol.* 70:181–191 (1991)). Most carotenoids have strong color and can be viewed as natural pigments or colorants. Furthermore, many carotenoids have potent antioxidant properties and thus inclusion of these compounds in the diet is thought to be healthful. Well-known examples are β-carotene and astaxanthin. Additionally, carotenoids are required elements of aquaculture. Salmon and shrimp aquaculture are particularly useful applications for this invention as carotenoid pigmentation is critically important for the value of these organisms. (F. Shahidi, J. A. Brown, Carotenoid pigments in seafood and aquaculture: Critical reviews in food *Science* 38(1): 1–67 (1998)). Finally, carotenoids have utility as intermediates in the synthesis of steroids, flavors and fragrances and compounds with potential electro-optic applications.

The disclosure below provides a detailed description of the selection of the appropriate C1 metabolizing microorganism for transformation and the production of various carotenoid compounds in high yield.

In this disclosure, a number of terms and abbreviations are used. The following definitions are provided.

The term "Embden-Meyerhof pathway" refers to the series of biochemical reactions for conversion of hexoses such as glucose and fructose to important cellular 3-carbon intermediates such as glyceraldehyde-3-phosphate, dihydroxyacetone phosphate, phosphophenol pyruvate and pyruvate. These reactions typically proceed with net yield of biochemically useful energy in the form of ATP. The key enzymes unique to the Embden-Meyerhof pathway are the phosphofructokinase and fructose-1,6 bisphosphate aldolase.

The term "Entner-Douderoff pathway" refers to a series of biochemical reactions for conversion of hexoses such as glucose or fructose to the important 3-carbon cellular intermediates pyruvate and glyceraldehyde-3-phosphate without any net production of biochemically useful energy. The key enzymes unique to the Entner-Douderoff pathway are the 6-phosphogluconate dehydratase and a ketodeoxyphosphogluconate aldolase.

The term "diagnostic" as it relates to the presence of a gene in a pathway refers to evidence of the presence of that pathway, where a gene having that activity is identified. Within the context of the present invention the presence of a gene encoding a pyrophosphate dependant phosphofructokinase is "diagnostic" for the presence of the Embden-Meyerhof carbon pathway and the presence of gene encoding a ketodeoxyphosphogluconate aldolase is "diagnostic" for the presence of the Entner-Douderoff carbon pathway.

The term "yield" is defined herein as the amount of cell mass produced per gram of carbon substrate metabolized.

The term "carbon conversion efficiency" is a measure of how much carbon is assimilated into cell mass and is calculated assuming a biomass composition of $CH_2O_{0.5}N_{0.25}$.

The term "$C_1$ carbon substrate" refers to any carbon-containing molecule that lacks a carbon-carbon bond. Examples are methane, methanol, formaldehyde, formic acid, formate, methylated amines (e.g., mono-, di-, and tri-methyl amine), methylated thiols, and carbon dioxide.

The term "C1 metabolizer" refers to a microorganism that has the ability to use an single carbon substrate as a sole source of energy and biomass. C1 metabolizers will typically be methylotrophs and/or methanotrophs.

The term "methylotroph" means an organism capable of oxidizing organic compounds which do not contain carbon-carbon bonds. Where the methylotroph is able to oxidize CH4, the methylotroph is also a methanotroph.

The term "methanotroph" means a prokaryote capable of utilizing methane as a substrate. Complete oxidation of methane to carbon dioxide occurs by aerobic degradation pathways. Typical examples of methanotrophs useful in the present invention include but are not limited to the genera *Methylomonas*, *Methylobacter*, *Methylococcus*, and *Methylosinus*.

The term "high growth methanotrophic bacterial strain" refers to a bacterium capable of growth with methane or methanol as sole carbon and energy source which possess a functional Embden-Meyerhof carbon flux pathway resulting in a yield of cell mass per gram of C1 substrate metabolized. The specific "high growth methanotrophic bacterial strain" described herein is referred to as "*Methylomonas* 16a" or "16a", which terms are used interchangeably.

The term "*Methylomonas* 16a" and "*Methylomonas* 16a sp." Are used interchangeably and refer to the *Methylomonas* strain used in the present invention.

The term "isoprenoid compound" refers to any compound which is derived via the pathway beginning with isopentenyl pyrophosphate (IPP) and formed by the head-to-tail condensation of isoprene units which may be of 5, 10, 15, 20, 30 or 40 carbons in length. There term "isoprenoid pigment" refers to a class of isoprenoid compounds which typically have strong light absorbing properties.

The term "upper isoprene pathway" refers to any of the following genes and gene products associated with the isoprenoid biosynthetic pathway including the dxs gene (encoding 1-deoxyxylulose-5-phosphate synthase), the dxr gene (encoding 1-deoxyxylulose-5-phosphate reductoisomerase), the "ispD" gene (encoding the 2C-methyl-D-erythritol cytidyltransferase enzyme; also known as ygbP), the "ispE" gene (encoding the 4-diphosphocytidyl-2-C-methylerythritol kinase; also known as ychB), the "ispF" gene (encoding a 2C-methyl-d-erythritol 2,4-cyclodiphosphate synthase; also known as ygbB), the "pyrG" gene (encoding a CTP synthase); the "lytB" gene involved in the formation of dimethylallyl diphosphate; and the gcpE gene involved in the synthesis of 2-C-methyl-D-erythritol 4-phosphate in the isoprenoid pathway.

The term "Dxs" refers to the 1-deoxyxylulose-5-phosphate synthase enzyme encoded by the dxs gene.

The term "Dxr" refers to the 1-deoxyxylulose-5-phosphate reductoisomerase enzyme encoded by the dxr gene.

The term "YgbP" or "IspD" refers to the 2C-methyl-D-erythritol cytidyltransferase enzyme encoded by the ygbP or ispD gene. The names of the gene, ygbP or ispD, are used interchangeably in this application. The names of gene product, YgbP or IspD are used interchangeably in this application.

The term "YchB" or "IspE" refers to the 4-diphosphocytidyl-2-C-methylerythritol kinase enzyme encoded by the ychB or ispE gene. The names of the gene, ychB or ispE, are used interchangeably in this application. The names of gene product, YchB or IspE are used interchangeably in this application.

The term "YgbB" or "IspF" refers to the 2C-methyl-d-erythritol 2,4-cyclodiphosphate synthase enzyme encoded by the ygbB or ispF gene. The names of the gene, ygbB or ispF, are used interchangeably in this application. The names of gene product, YgbB or IspF are used interchangeably in this application.

The term "PyrG" refers to a CTP synthase enzyme encoded by the pyrG gene.

The term "IspA" refers to Geranyltransferase or farnesyl diphosphate synthase enzyme as one of prenyl transferase family encoded by ispA gene.

The term "LytB" refers to protein having a role in the formation of dimethylallyl-pyrophosphate in the isoprenoid pathway and which is encoded by lytB gene.

The term "gcpE" refers to a protein having a role in the formation of 2-C-methyl-D-erythritol 4-phosphate in the isoprenoid pathway (Altincicek et al., *J. Bacteriol.* (2001), 183(8), 2411–2416; Campos et al., FEBS Lett. (2001), 488(3), 170–173)

The term "lower carotenoid biosynthetic pathway" refers to any of the following genes and gene products associated with the isoprenoid biosynthetic pathway, which are involved in the immediate synthesis of phytoene (whose synthesis represents the first step unique to biosynthesis of carotenoids) or subsequent reactions. These genes and gene products include the "ispA" gene (encoding geranyltransferase or farnesyl diphosphate synthase), the "ctrN" and "ctrN 1" genes (encoding diapophytoene dehydrogenases), the "crtE" gene (encoding geranylgeranyl pyrophosphate synthase), the "crtX" gene (encoding zeaxanthin glucosyl transferase), the "crtY" gene (encoding lycopene cyclase), the "crtI" gene (encoding phytoene desaturase), the "crtB" gene (encoding phytoene synthase), the "crtZ" gene (encoding β-carotene hydroxylase), and the "crtO" gene (encoding a β-carotene ketolase). Additionally, the term "carotenoid biosynthetic enzyme" is an inclusive term referring to any and all of the enzymes in the present pathway including CrtE, CrtX, CrtY, CrtI, CrtB, CrtZ, and CrtO.

The term "IspA" refers to the protein encoded by the ispA gene, and whose activity catalyzes a sequence of 3 prenyl-transferase reactions in which geranyl pyrophosphate (GPP), farnesyl pyrophosphate (FPP), and geranylgeranyl pyrophosphate (GGPP) are formed.

The term "CrtN1" or "CrtN, copy1" refers to copy 1 of the diapophytoene dehydrogenase enzyme encoded by crtN1 gene.

The term "CrtN2" or "CrtN copy2" refers to copy 2 of the diapophytoene dehydrogenase enzyme(Crt) encoded by crtN2 gene.

The term "CrtE" refers to geranylgeranyl pyrophosphate synthase enzyme encoded by crtE gene which converts trans-trans-farnesyl diphosphate and isopentenyl diphosphate into pyrophosphate and geranylgeranyl diphosphate.

The term "CrtX" refers to the zeaxanthin glucosyl transferase enzyme encoded by the crtX gene, and which glycosolates zeaxanthin to produce zeaxanthin-β-diglucoside.

The term "CrtY" refers to the lycopene cyclase enzyme encoded by the crtY gene and which catalyzes conversion of lycopene to β-carotene.

The term "CrtI" refers to the phytoene desaturase enzyme encoded by the crtI gene and which converts phytoene into lycopene via the intermediaries of phytofluene, zeta-carotene, and neurosporene by the introduction of 4 double bonds.

The term "CrtB" refers to the phytoene synthase enzyme encoded by the crtB gene which catalyses the reaction from prephytoene diphosphate to phytoene.

The term "CrtZ" refers to the β-carotene hydroxylase enzyme encoded by crtZ gene which catalyses the hydroxylation reaction from β-carotene to zeaxanthin.

The term "CrtO" refers to the β-carotene ketolase enzyme encoded by crtO gene which catalyses conversion of β-carotene into canthaxanthin (two ketone groups) via echinenone (one ketone group) as the intermediate.

The term "Carotenoid compound" is defined as a class of hydrocarbons (carotenes) and their oxygenated derivatives (xanthophylls) consisting of eight isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All carotenoids may be formally derived from the acyclic C40H56 structure (Formula I below), having a long central chain of conjugated double bonds, by (i) hydrogenation, (ii) dehydrogenation, (iii) cyclization, or (iv) oxidation, or any combination of these processes.

Formula I

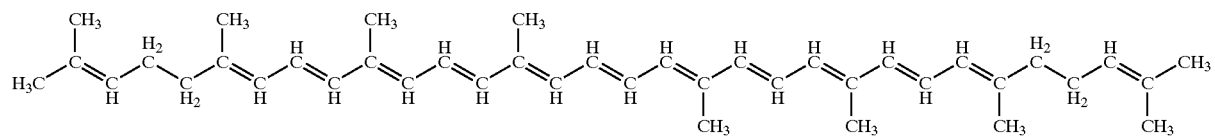

(I)

This class also includes certain compounds that arise from certain rearrangements of the carbon skeleton (I), or by the (formal) removal of part of this structure.

For convenience carotenoid formulae are often written in a shorthand form as

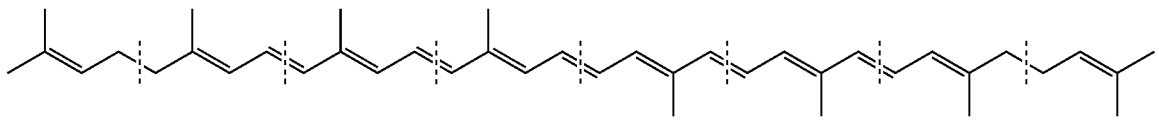

(IA)

where the broken lines indicate formal division into isoprenoid units.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

"Gene" refers to a nucleic acid fragment that is capable of being expressed as a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs.

Sequence alignments and percent identity calculations may be performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional preferred set of stringent conditions include 0.1×SSC, 0.1% SDS, 65° C. and washed with 2×SSC, 0.1% SDS followed by 0.1×SSC, 0.1% SDS).

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

Identification and Isolation of C1 Metabolizing Microorganisms

The present invention provides for the expression of genes involved in the biosynthesis of carotenoid compounds in microorganisms which are able to use single carbon substrates as a sole energy source. Such microorganisms are referred to herein as C1 metabolizers. The host microorganism may be any C1 metabolizer which has the ability to synthesize isopentenyl pyrophosphate (IPP) the precursor for many of the carotenoids.

Many C1 metabolizing microorganisms are known in the art which are able to use a variety of single carbon substrates. Single carbon substrates useful in the present invention include but are not limited to methane, methanol, formaldehyde, formic acid, methylated amines (e.g. mono-, di- and tri-methyl amine), methylated thiols, and carbon dioxide.

All C1 metabolizing microorganisms are generally classified as methylotrophs. Methylotrophs may be defined as any organism capable of oxidizing organic compounds which do not contain carbon-carbon bonds. A subset of methylotrophs are the methanotrophs, which have the distinctive ability to oxidize methane. Facultative methylotrophs have the ability to oxidize organic compounds which do not contain carbon-carbon bonds, but may also use other carbon substrates such as sugars and complex carbohydrates for energy and biomass. Obligate methylotrophs are those organisms which are limited to the use of organic compounds which do not contain carbon-carbon bonds for the generation of energy and obligate methanotrophs are those obligate methylotrophs that have the ability to oxidize methane.

Facultative methylotrophic bacteria are found in many environments, but are isolated most commonly from soil, landfill and waste treatment sites. Many facultative methylotrophs are members of the β, and γ subgroups of the Proteobacteria (Hanson et al., *Microb. Growth C1 Compounds.*, [Int. Symp.], 7th (1993), 285–302. Editor(s): Murrell, J. Collin; Kelly, Don P. Publisher: Intercept, Andover, UK; Madigan et al., *Brock Biology of Microorganisms*, 8th edition, Prentice Hall, UpperSaddle River, N.J. (1997)). Facultative methylotrophic bacteria suitable in the present invention include but are not limited to, *Methylophilus, Methylobacillus, Methylobacterium, Hyphomicrobium, Xanthobacter, Bacillus, Paracoccus, Nocardia, Arthrobacter, Rhodopseudomonas*, and *Pseudomonas*.

The ability to utilize single carbon substrates is not limited to bacteria but extends also to yeasts and fungi. A number of yeast genera are able to use single carbon substrates in addition to more complex materials as energy sources. Specific methylotrophic yeasts useful in the present invention include but are not limited to *Candida, Hansenula, Pichia, Torulopsis*, and *Rhodotorula*.

Those methylotrophs having the additional ability to utilize methane are referred to as methanotrophs. Of particular interest in the present invention are those obligate methanotrophs which are methane utilizers but which are obliged to use organic compounds lacking carbon-carbon bonds. Exemplary of these organisms are included in, but not limited to, the genera *Methylomonas, Methylobacter, Mehtylococcus, Methylosinus, Methylocyctis, Methylomicrobium*, and *Methanomonas*.

Of particular interest in the present invention are high growth obligate methanotrophs having an energetically favorable carbon flux pathway. For example, Applicants have discovered a specific strain of methanotroph having several pathway features which make it particularly useful for carbon flux manipulation. This type of strain has served as the host in the present application and is known as *Methylomonas* 16a (ATCC PTA 2402).

The present strain contains several anomalies in the carbon utilization pathway. For example, based on genome sequence data, the strain is shown to contain genes for two pathways of hexose metabolism. The Entner-Douderoff Pathway, which utilizes the keto-deoxy phosphogluconate aldolase enzyme, is present in the strain. It is generally well accepted that this is the operative pathway in obligate methanotrophs. Also present however is the Embden-Meyerhof Pathway, which utilizes the fructose bisphosphate aldolase enzyme. It is well known that this pathway is either not present or not operative in obligate methanotrophs. Energetically, the latter pathway is most favorable and allows greater yield of biologically useful energy, which ultimately results in greater yield production of cell mass and other cell mass-dependent products in *Methylomonas* 16a. The activity of this pathway in the present 16a strain has been confirmed through microarray data and biochemical evidence measuring the reduction of ATP. Although the 16a strain has been shown to possess both the Embden-Meyerhof and the Entner-Douderoff pathway enzymes, the data suggests that the Embden-Meyerhof pathway enzymes are more strongly expressed than the Entner-Douderoff pathway enzymes. This result is surprising and counter to existing beliefs on the glycolytic metabolism of methanotrophic bacteria. Applicants have discovered other methanotrophic bacteria having this characteristic, including for example, *Methylomonas clara* and *Methylosinus sporium*. It is likely that this activity has remained undiscovered in methanotrophs due to the lack of activity of the enzyme with ATP, the typical phosphoryl donor for the enzyme in most bacterial systems.

A particularly novel and useful feature of the Embden-Meyerhof pathway in strain 16a is that the key phosphofructokinase step is pyrophosphate dependent instead of ATP dependent. This feature adds to the energy yield of the pathway by using pyrophosphate instead of ATP. Because of its significance in providing an energetic advantage to the strain, this gene in the carbon flux pathway is considered diagnostic for the present strain.

Comparison of the pyrophosphate dependent phosphofructokinase gene sequence (SEQ ID NO:1) and deduced amino acid sequence (SEQ ID NO:2) to public databases reveals that the most similar known sequence is about 63% identical to the amino acid sequence of reported herein over length of 437 amino acids using a Smith-Waterman alignment algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). More preferred amino acid fragments are at least about 80%–90% identical to the sequences herein. Most preferred are nucleic acid fragments that are at least 95% identical to the amino acid fragments reported herein. Similarly, preferred pyrophosphate dependent phosphofructokinase encoding nucleic acid sequences corresponding to the instant gene are those encoding active proteins and which are at least 80% identical to the nucleic acid sequences of reported herein. More preferred pyrophosphate dependent phosphofructokinase nucleic acid fragments are at least 90% identical to the sequences herein. Most preferred are pyrophosphate dependent phosphofructokinase nucleic acid fragments that are at least 95% identical to the nucleic acid fragments reported herein.

Figure 2:
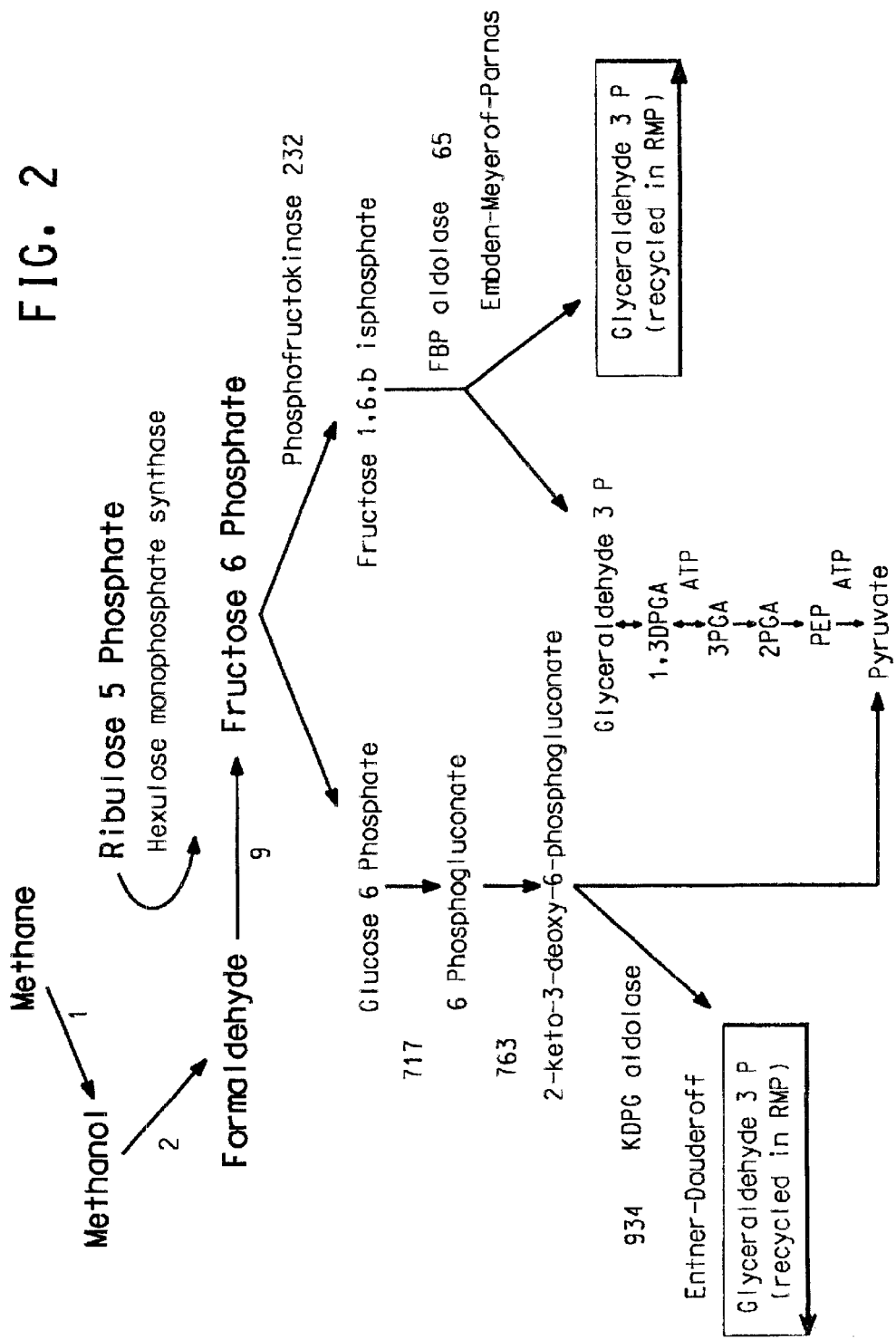

A further distinguishing characteristic of the present strain is revealed when examining the "cleavage" step which occurs in the Ribulose Monophosphate Pathway, or RuMP cycle. This cyclic set of reactions converts methane to biomolecules in methanotrophic bacteria. The pathway is comprised of three phases, each phase being a series of enzymatic steps (FIG. 2). The first step is "fixation" or incorporation of C-1 (formaldehyde) into a pentose to form a hexose or six-carbon sugar. This occurs via a condensation reaction between a 5-carbon sugar (pentose) and formaldehyde and is catalyzed by the hexulose monophosphate synthase enzyme. The second phase is termed "cleavage" and results in splitting of that hexose into two 3-carbon molecules. One of those three-carbon molecules is recycled back through the RuMP pathway, while the other 3-carbon fragment is utilized for cell growth. In methanotrophs and methylotrophs, the RuMP pathway may occur as one of three variants. However, only two of these variants are commonly found, identified as the FBP/TA (fructose bisphosphotase/transaldolase) pathway or the KDPG/TA (keto deoxy phosphogluconate/transaldolase) pathway (Dijkhuizen L., G. E. Devries. The Physiology and biochemistry of aerobic methanol-utilizing gram negative and gram positive bacteria. In: *Methane and Methanol Utilizers* (1992), eds. Colin Murrell and Howard Dalton; Plenum Press:NY).

The present strain is unique in the way it handles the "cleavage" steps as genes were found that carry out this conversion via fructose bisphosphate as a key intermediate. The genes for fructose bisphosphate aldolase and transaldolase were found clustered together on one piece of DNA. Secondly, the genes for the other variant involving the keto deoxy phosphogluconate intermediate were also found clustered together. Available literature teaches that these organisms (methylotrophs and methanotrophs) rely solely on the KDPG pathway and that the FBP-dependent fixation pathway is utilized by facultative methylotrophs (Dijkhuizen et al., supra). Therefore the latter observation is expected whereas the former is not. The finding of the FBP genes in an obligate methane utilizing bacterium is both surprising and suggestive of utility. The FBP pathway is energetically favorable to the host microorganism due to the fact that less energy (ATP) is utilized than is utilized in the KDPG pathway. Thus organisms that utilize the FBP pathway may have an energetic advantage and growth advantage over those that utilize the KDPG pathway. This advantage may also be useful for energy-requiring production pathways in the strain. By using this pathway a methane-utilizing bacterium may have an advantage over other methane utilizing organisms as production platforms for either single cell protein or for any other product derived from the flow of carbon through the RuMP pathway.

Accordingly the present invention provides a method for the production of a carotenoid compound comprising providing a transformed C1 metabolizing host cell which (a) grows on a C1 carbon substrate selected from the group consisting of methane and methanol; and (b) comprises a functional Embden-Meyerhof carbon pathway, said pathway comprising a gene encoding a pyrophosphate dependent phosphofructokinase enzyme.

Isolation of C1 Metabolizing Microorganisms

The C1 metabolizing microorganisms of the present invention are ubiquitous and many have been isolated and characterized. A general scheme for isolation of these strains includes addition of an inoculum into a sealed liquid mineral salts media, containing either methane or methanol. Care must be made of the volume:gas ratio and cultures are typically incubated between 25–55° C. Typically, a variety of different methylotrophic bacteria can be isolated from a first enrichment, if it is plated or streaked onto solid media when growth is first visible. Methods for the isolation of methanotrophs are common and well known in the art (See for example Thomas D. Brock in Biotechnology: *A Textbook of Industrial Microbiology*, Second Edition (1989) Sinauer Associates, Inc., Sunderland, Mass.; Deshpande, Mukund V., *Appl. Biochem. Biotechnol.*, 36: 227 (1992); or Hanson, R. S. et al. *The Prokaryotes: a handbook on habitats, isolation, and identification of bacteria*; Springer-Verlag: Berlin, New York, 1981; Volume 2, Chapter 118).

As noted above, preferred C1 metabolizer is one that incorporates an active Embden-Meyerhof pathway as indicated by the presence of a pyrophosphate dependent phosphofructokinase. It is contemplated that the present teaching will enable the general identification and isolation of similar strains. For example, the key characteristics of the present high growth strain are that it is an obligate methanotroph, using only either methane of methanol as a sole carbon source and possesses a functional Embden-Meyerhof, and particularly a gene encoding a pyrophosphate dependent phosphofructokinase. Methods for the isolation of methanotrophs are common and well known in the art (See for example Thomas D. Brock supra or Deshpande, supra). Similarly, pyrophosphate dependent phosphofructokinase has been well characterized in mammalian systems and assay methods have been well developed (see for example Schliselfeld et al. *Clin. Biochem.* (1996), 29(1), 79–83; Clark et al., *J. Mol. Cell. Cardiol.* (1980),12(10), 1053–64. The contemporary microbiologist will be able to use these techniques to identify the present high growth strain.

Genes Involved in Carotenoid Production.

The enzyme pathway involved in the biosynthesis of carotenoids can be conveniently viewed in two parts, the upper isoprenoid pathway providing for the conversion of pyruvate and glyceraldehyde-3-phosphate to isopentenyl pyrophosphate and the lower carotenoid biosynthetic pathway, which provides for the synthesis of phytoene and all subsequently produced carotenoids. The upper pathway is ubiquitous in many C1 metabolizing microorganisms and in these cases it will only be necessary to introduce genes that comprise the lower pathway for the biosynthesis of the desired carotenoid. The key division between the two pathways concerns the synthesis of isopentenyl pyrophosphate (IPP). Where IPP is naturally present only elements of the lower carotenoid pathway will be needed. However, it will be appreciated that for the lower pathway carotenoid genes to be effective in the production of carotenoids, it will be necessary for the host cell to have suitable levels of IPP within the cell. Where IPP synthesis is not provided by the host cell, it will be necessary to introduce the genes necessary for the production of IPP. Each of these pathways will be discussed below in detail.

The Upper Isoprenoid Pathway

Figure 1B:
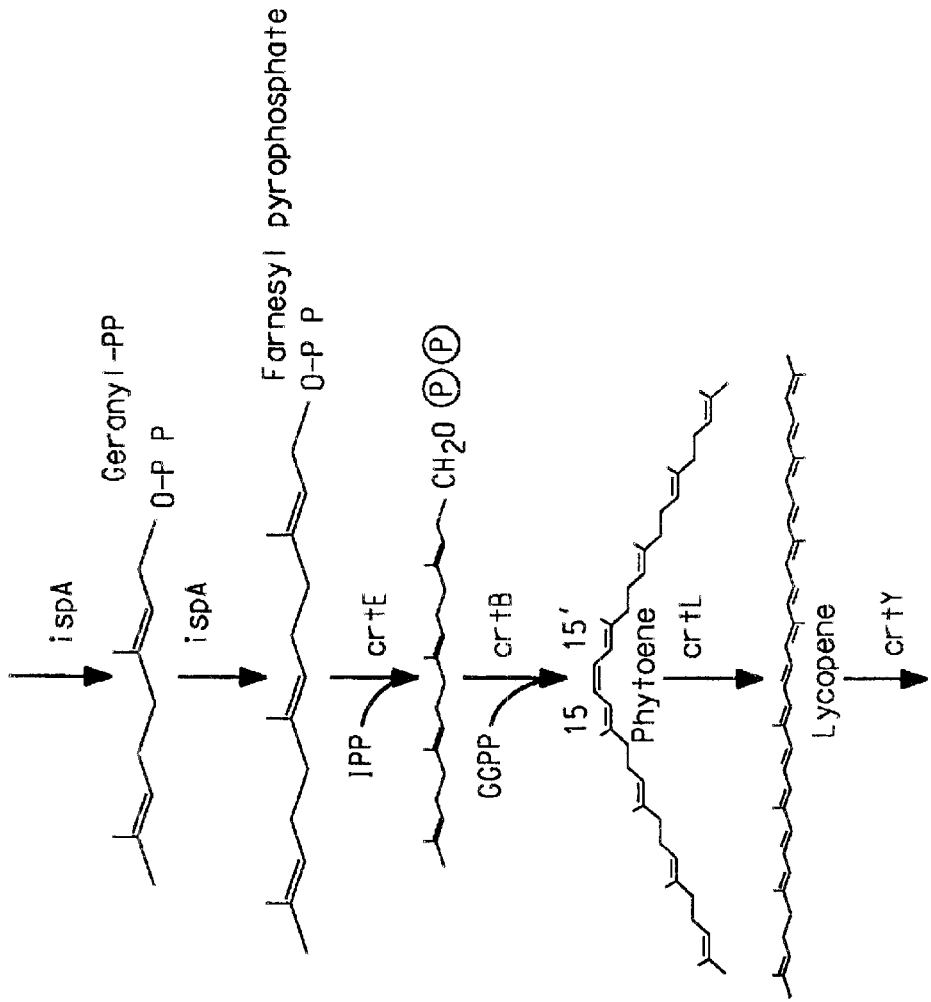

IPP biosynthesis occurs through either of two pathways. First, IPP may be synthesized through the well-known acetate/mevalonate pathway. However, recent studies have demonstrated that the mevalonate-dependent pathway does not operate in all living organisms. An alternate mevalonate-independent pathway for IPP biosynthesis has been characterized in bacteria and in green algae and higher plants (Horbach et al., *FEMS Microbiol. Lett.* 111:135–140(1993); Rohmer et al, *Biochem.* 295: 517–524 (1993); Schwender et al., *Biochem.* 316: 73–80 (1996); Eisenreich et al., *Proc. Natl. Acad. Sci. USA* 93: 6431–6436 (1996)). Many steps in both isoprenoid pathways are known (FIG. 1). For example, the initial steps of the alternate pathway leading to the production of IPP have been studied in *Mycobacterium tuberculosis* by Cole et al. (*Nature* 393:537–544 (1998)). The first step of the pathway involves the condensation of two 3-carbon molecules (pyruvate and D-glyceraldehyde 3-phosphate) to yield a 5-carbon compound known as D-1-deoxyxylulose-5-phosphate. This reaction occurs by the DXS enzyme, encoded by the dxs gene. Next, the isomerization and reduction of D-1-deoxyxylulose-5-phosphate yields 2-C-methyl-D-erythritol-4-phosphate. One of the enzymes involved in the isomerization and reduction process is D-1-deoxyxylulose-5-phosphate reductoisomerase (DXR), encoded by the gene dxr. 2-C-methyl-D-erythritol-4-phosphate is subsequently converted into 4-diphosphocytidyl-2C-methyl-D-erythritol in a CTP-dependent reaction by the enzyme encoded by the non-annotated gene ygbP (Cole et al., supra). Recently, however, the ygbP gene was renamed as ispD as a part of the isp gene cluster (SwissProtein Accession #Q46893).

Next, the $2^{nd}$ position hydroxy group of 4-diphosphocytidyl-2C-methyl-D-erythritol can be phosphorylated in an ATP-dependent reaction by the enzyme encoded by the ychB gene. This product phosphorylates 4-diphosphocytidyl-2C-methyl-D-erythritol, resulting in 4-diphosphocytidyl-2C-methyl-D-erythritol 2-phosphate. The ychB gene was renamed as ispE, also as a part of the isp gene cluster (SwissProtein Accession #P24209). Finally, the product of ygbB gene converts 4-diphosphocytidyl-2C-methyl-D-erythritol 2-phosphate to 2C-methyl-D-erythritol 2,4-cyclodiphosphate in a CTP-dependent manner. This gene has also been recently renamed, and belongs to the isp gene cluster. Specifically, the new name for the ygbB gene is ispF (SwissProtein Accession #P36663).

It is known that 2C-methyl-D-erythritol 2,4-cyclodiphosphate can be further converted into IPP to ultimately produce carotenoids in the carotenoid biosynthesis pathway. However, the reactions leading to the production of isopentenyl monophosphate from 2C-methyl-D-erythritol 2,4-cyclodiphosphate are not yet well-characterized. The enzymes encoded by the lytB and gcpE genes (and perhaps others) are thought to participate in the reactions leading to formation of isopentenyl pyrophosphate (IPP) and dimethylallyl pyrophosphate (DMAPP).

IPP may be isomerized to DMAPP via IPP isomerase, encoded by the idi gene, however this enzyme is not essential for survival and may be absent in some bacteria using 2-C-methyl-D-erythritol 4-phosphate (MEP) pathway. Recent evidence suggests that the MEP pathway branches before IPP and separately produces IPP and DMAPP via the lytB gene product. A lytB knockout mutation is lethal in *E. coli* except in media supplemented with both IPP and DMAPP.

Genes encoding elements of the upper pathway are known from a variety of plant, animal, and bacterial sources, as shown in Table 2.

TABLE 2

Sources of Genes Encoding the Upper Isoprene Pathway

| Gene | Genbank Accession Number and Source Organism |
| --- | --- |
| dxs | AF035440, *Escherichia coli* |
|  | Y18874, *Synechococcus* PCC6301 |
|  | AB026631, Streptomyces sp. CL190 |
|  | AB042821, *Streptomyces griseolosporeus* |
|  | AF111814, *Plasmodium falciparum* |
|  | AF143812, *Lycopersicon esculentum* |
|  | AJ279019, *Narcissus pseudonarcissus* |
|  | AJ291721, *Nicotiana tabacum* |
| dxr | AB013300, *Escherichia coli* |
|  | AB049187, *Streptomyces griseolosporeus* |
|  | AF111813, *Plasmodium falciparum* |
|  | AF116825, *Mentha x piperita* |
|  | AF148852, *Arabidopsis thaliana* |
|  | AF182287, *Artemisia annua* |
|  | AF250235, *Catharanthus roseus* |
|  | AF282879, *Pseudomonas aeruginosa* |
|  | AJ242588, *Arabidopsis thaliana* |
|  | AJ250714, *Zymomonas mobilis* strain ZM4 |
|  | AJ292312, *Klebsiella pneumoniae,* |
|  | AJ297566, *Zea mays* |
| ispD | AB037876, *Arabidopsis thaliana* |
|  | AF109075, *Clostridium difficile* |
|  | AF230736, *Escherichia coli* |
|  | AF230737, *Arabidopsis thaliana* |
| ispE | AF216300, *Escherichia coli* |
|  | AF263101, *Lycopersicon esculentum* |
|  | AF288615, *Arabidopsis thaliana* |

TABLE 2-continued

Sources of Genes Encoding the Upper Isoprene Pathway

| Gene | Genbank Accession Number and Source Organism |
| --- | --- |
| ispF | AB038256, *Escherichia coli* mecs gene |
|  | AF230738, *Escherichia coli* |
|  | AF250236, *Catharanthus roseus* (MECS) |
|  | AF279661, *Plasmodium falciparum* |
|  | AF321531, *Arabidopsis thaliana* |
| pyrG | AB017705, *Aspergillus oryzae* |
|  | AB064659, *Aspergillus kawachii* |
|  | AF061753, *Nitrosomonas europaea* |
|  | AF206163, *Solorina crocea* |
|  | L22971, *Spiroplasma citri* |
|  | M12843, *E. coli* |
|  | M19132, *Emericella nidulans* |
|  | M69112, *Mucor circinelloides* |
|  | U15192, *Chlamydia trachomatis* |
|  | U59237, Synechococcus PCC7942 |
|  | U88301, *Mycobacterium bovis* |
|  | X06626, *Aspergillus niger* |
|  | X08037, *Penicillium chrysogenum* |
|  | X53601, *P. blakesleeanus* |
|  | X67216, *A. brasilense* |
|  | Y11303, *A. fumigatus* |
|  | Y13811, *Aspergillus oryzae* |
|  | NM_001905 |
|  | *Homo sapiens* CTP synthase (CTPS), mRNA |
|  | NM_016748, *Mus musculus* cytidine 5'-triphosphate synthase (Ctps), mRNA |
|  | NM_019857 |
|  | *Homo sapiens* CTP synthase II (CTPS2), |
|  | X68196 |
|  | mRNAS.cerevisiae ura8 gene for CTP synthetase |
|  | XM_013134 |
|  | BC009408, *Homo sapiens*, CTP synthase, clone MGC10396 IMAGE 3355881 |
|  | *Homo sapiens* CTP synthase II (CTPS2), mRNA XM_046801 |
|  | *Homo sapiens* CTP synthase II (CTPS2), mRNA XM_046802 |
|  | *Homo sapiens* CTP synthase II (CTPS2), mRNA XM_046803 |
|  | *Homo sapiens* CTP synthase II (CTPS2), mRNA XM_046804 |
|  | *Homo sapiens* CTP synthase II (CTPS2), mRNA Z47198, *A. parasiticus* pksA gene for polyketide synthase |
| lytB | AF027189, Acinetobacter sp. BD4I 3 |
|  | AF098521, *Burkholderia pseudomallei* |
|  | AF291696, *Streptococcus pneumoniae* |
|  | AF323927, *Plasmodium falciparum* gene |
|  | M87645, *Bacillus subtillis* |
|  | U38915, Synechocystis sp. |
|  | X89371, *C. jejuni* |
| gcpE | sp O67496 |
|  | sp P54482 |
|  | tr Q9pky3 |
|  | tr Q9Z8H0 |
|  | sp O84060 |
|  | sp P27433 |
|  | sp P44667 |
|  | tr Q9ZLL0 |
|  | sp O33350 |
|  | pir S77159 |
|  | tr Q9WZZ3 |
|  | sp O83460 |
|  | tr Q9JZ40 |
|  | tr Q9PPMI |
|  | tr Q9RXC9 |
|  | tr AAG07190 |
|  | tr Q9KTX1 |

The most preferred source of genes for the upper isoprene pathway in the present invention is from *Methylomonas* 16a. *Methylomonas* 16a is particularly well suited for the present invention, as the methanotroph is naturally pink-pigmented, producing a 30-carbon carotenoid. Thus, the organism is well-endowed with the genes of the upper isoprene pathway. Sequences of these preferred genes are presented as the following SEQ ID numbers: the dxs gene (SEQ ID NO:5), the dxr gene (SEQ ID NO:7), the "ispD" gene (SEQ ID NO:9), the "ispE" gene (SEQ ID NO:11), the "ispF" gene (SEQ ID NO:13), the "pyrG" gene (SEQ ID NO:15), and the "lytB" gene (SEQ ID NO:17).

The Lower Carotenoid Biosynthetic Pathway

The formation of phytoene is the first "true" step unique in the biosynthesis of carotenoids and produced via the lower carotenoid biosynthetic pathway, despite the compound's being colorless. The synthesis of phytoene occurs via isomerization of IPP to dimethylallyl pyrophosphate (DMAPP). This reaction is followed by a sequence of 3 prenyltransferase reactions. Two of these reactions are catalyzed by ispA, leading to the creation of geranyl pyrophosphate (GPP; a 10-carbon molecule) and farnesyl pyrophosphate (FPP; 15-carbon molecule).

The gene crtN1 and N2 convert farnesyl pyrophosphate to naturally occurring 16A 30-carbon pigment.

The gene crtE, encoding GGPP synthetase is responsible for the $3^{rd}$ prenyltransferase reaction which may occur, leading to the synthesis of phytoene. This reaction adds IPP to FPP to produce a 20-carbon molecule, geranylgeranyl pyrophosphate (GGPP).

Finally, a condensation reaction of two molecules of GGPP occur to form phytoene (PPPP), the first 40-carbon molecule of the lower carotenoid biosynthesis pathway. This enzymatic reaction is catalyzed by crtB, encoding phytoene synthase.

Lycopene, which imparts a "red"-colored spectra, is produced from phytoene through four sequential dehydrogenation reactions by the removal of eight atoms of hydrogen, catalyzed by the gene crtI (encoding phytoene desaturase). Intermediaries in this reaction are phtyofluene, zeta-carotene, and neurosporene.

Lycopene cyclase (crtY) converts lycopene to β-carotene.

β-carotene is converted to zeaxanthin via a hydroxylation reaction resulting from the activity of β-carotene hydroxylase (encoded by the crtZ gene). B-cryptoxanthin is an intermediate in this reaction.

β-carotene is converted to canthaxanthin by β-carotene ketolase encoded by the crtW gene. Echinenone in an intermediate in this reaction. Canthaxanthin can then be converted to astaxanthin by β-carotene hydroxylase encoded by the crtZ gene. Adonbirubrin is an intermediate in this reaction.

Zeaxanthin can be converted to zeaxanthin-β-diglucoside. This reaction is catalyzed by zeaxanthin glucosyl transferase (crtX).

Zeaxanthin can be converted to astaxanthin by β-carotene ketolase encoded by crtW, crtO or bkt. Adonixanthin is an intermediate in this reaction.

Spheroidene can be converted to spheroidenone by spheroidene monooxygenase encoded by crtA.

Nerosporene can be converted spheroidene and lycopene can be converted to spirilloxanthin by the sequential actions of hydroxyneurosporene synthase, methoxyneurosporene desaturase and hydroxyneurosporene-O-methyltransferase encoded by the crtC, crtD and crtF genes, respectively.

β-carotene can be converted to isorenieratene by b-carotene desaturase encoded by crtU.

Genes encoding elements of the lower carotenoid biosynthetic pathway are known from a variety of plant, animal, and bacterial sources, as shown in Table 3.

TABLE 3

Sources of Genes Encoding the Lower Carotenoid Biosynthetic Pathway

| Gene | Genbank Accession Number and Source Organism |
| --- | --- |
| ispA | AB003187, *Micrococcus luteus* |
| | AB016094, *Synechococcus elongatus* |
| | AB021747, *Oryza sativa* FPPSI gene for farnesyl diphosphate synthase |
| | AB028044, *Rhodobacter sphaeroides* |
| | AB028046, *Rhodobacter capsulatus* |
| | AB028047, *Rhodovulum sulfidophilum* |
| | AF112881 and AF136602, *Artemisia annua* |
| | AF384040, *Mentha x piperita* |
| | D00694, *Escherichia coli* |
| | D13293, *B. stearothermophilus* |
| | D85317, *Oryza sativa* |
| | X75789, *A. thaliana* |
| | Y12072, *G. arboreum* |
| | Z49786, *H. brasiliensis* |
| | U80605, *Arabidopsis thaliana* farnesyl diphosphate synthase precursor (FPS1) mRNA, complete cds |
| | X76026, *K. lactis* FPS gene for farnesyl diphosphate synthetase, QCR8 gene for bc1 complex, subunit VIII |
| | X82542, *P. argentatum* mRNA for farnesyl diphosphate synthase (FPS1) |
| | X82543, *P. argentatum* mRNA for farnesyl diphosphate synthase (FPS2) |
| | BC010004, *Homo sapiens*, farnesyl diphosphate synthase (farnesyl pyrophosphate synthetase, dimethylallyltranstransferase, geranyltranstransferase), clone MGC 15352 IMAGE, 4132071, mRNA, complete cds |
| | AF234168, *Dictyostelium discoideum* farnesyl diphosphate synthase (Dfps) |
| | L46349, *Arabidopsis thaliana* farnesyl diphosphate synthase (FPS2) mRNA, complete cds |
| | L46350, *Arabidopsis thaliana* farnesyl diphosphate synthase (FPS2) gene, complete cds |
| | L46367, *Arabidopsis thaliana* farnesyl diphosphate synthase (FPSI) gene, alternative products, complete cds |
| | M89945, Rat farnesyl diphosphate synthase gene, exons 1–8 |
| | NM_002004, *Homo sapiens* farnesyl diphosphate synthase (farnesyl pyrophosphate synthetase, dimethylallyltranstransferase, geranyltranstransferase) (FDPS), mRNA |
| | U36376 *Artemisia annua* farnesyl diphosphate synthase (fps1) mRNA, complete cds |
| | XM_001352, *Homo sapiens* farnesyl diphosphate synthase (farnesyl pyrophosphate synthetase, dimethylallyltranstransferase, geranyltranstransferase) (FDPS), mRNA |
| | XM_034497 *Homo sapiens* farnesyl diphosphate synthase (farnesyl pyrophosphate synthetase, dimethylallyltranstransferase, geranyltranstransferase) (FDPS), mRNA |
| | XM_034498 *Homo sapiens* farnesyl diphosphate synthase (farnesyl pyrophosphate synthetase, dimethylallyltranstransferase, geranyltranstransferase) (FDPS), mRNA |
| | XM_034499 *Homo sapiens* farnesyl diphosphate synthase (farnesyl pyrophosphate synthetase, dimethylallyltranstransferase, geranyltranstransferase) (FDPS), mRNA |
| | XM_034500 *Homo sapiens* farnesyl diphosphate synthase (farnesyl pyrophosphate synthetase, dimethylallyltranstransferase, geranyltranstransferase) (FDPS), mRNA |
| crtN | X73889, *S. aureus* |
| crtE (GGPP Synthase) | AB000835, *Arabidopsis thaliana* |
| | AB016043 and AB019036, *Homo sapiens* |
| | AB016044, *Mus musculus* |

TABLE 3-continued

Sources of Genes Encoding the Lower Carotenoid Biosynthetic Pathway

| Gene | Genbank Accession Number and Source Organism |
|---|---|
| | AB027705 and AB027706, *Daucus carota* |
| | AB034249, *Croton sublyratus* |
| | AB034250, *Scoparia dulcis* |
| | AF020041, *Helianthus annuus* |
| | AF049658, *Drosophila melanogaster* signal recognition particle 19kDa protein (srp19) gene, partial sequence; and geranylgeranyl pyrophosphate synthase (quemao) gene, complete cds |
| | AF049659, *Drosophila melanogaster* geranylgeranyl pyrophosphate synthase mRNA, complete cds |
| | AF139916, *Brevibacterium linens* |
| | AF279807, *Penicillium paxilli* geranylgeranyl pyrophosphate synthase (ggs1) gene, complete |
| | AF279808 *Penicillium paxilli* dimethylallyl tryptophan synthase (paxD) gene, partial cds; and cytochrome P450 monooxygenase (paxQ), cytochrome P450 monooxygenase (paxP), PaxC (paxC), monooxygenase (paxM), geranylgeranyl pyrophosphate synthase (paxG), PaxU (paxU), and metabolite transporter (paxT) genes, complete cds |
| | AJ010302, *Rhodobacter sphaeroides* |
| | AJ133724, *Mycobacterium aurum* |
| | AJ276129, *Mucor circinelloides f. lusitanicus* carG gene for geranylgeranyl pyrophosphate synthase, exons 1–6 |
| | D85029 *Arabidopsis thaliana* mRNA for geranylgeranyl pyrophosphate synthase, partial cds |
| | L25813, *Arabidopsis thaliana* |
| | L37405, *Streptomyces griseus* geranylgeranyl pyrophosphate synthase (crtB), phytoene desaturase (cftE) and phytoene synthase (cftI) genes, complete cds |
| | U15778, *Lupinus albus* geranylgeranyl pyrophosphate synthase (ggps1) mRNA, complete cds |
| | U44876, *Arabidopsis thaliana* pregeranyigeranyl pyrophosphate synthase (GGPS2) mRNA, complete cds |
| | X92893, *C. roseus* |
| | X95596, *S. griseus* |
| | X98795, *S. alba* |
| | Y15112, *Paracoccus marcusii* |
| crtX | D90087, *E. uredovora* |
| | M87280 and M90698, *Pantoea agglomerans* |
| crtY | AF139916, *Brevibacterium linens* |
| | AF152246, *Citrus x paradisi* |
| | AF218415, Bradyrhizobium sp. ORS278 |
| | AF272737, *Streptomyces griseus* strain IFO13350 |
| | AJ133724, *Mycobacterium aurum* |
| | AJ250827, *Rhizomucor circinelloides f. lusitanicus* carRP gene for lycopene cyclase/phytoene synthase, exons 1–2 |
| | AJ276965, *Phycomyces blakesleeanus* carRA gene for phytoene synthase/lycopene cyclase, exons 1–2 |
| | D58420, *Agrobacterium aurantiacum* |
| | D83513, *Erythrobacter longus* |
| | L40176, *Arabidopsis thaliana* lycopene cyclase (LYC) mRNA, complete cds |
| | M87280, *Pantoea agglomerans* |
| | U50738, *Arabodopsis thaliana* lycopene epsilon cyclase mRNA, complete cds |
| | U50739 *Arabidosis thaliana* lycopene β cyclase mRNA, complete cds |
| | U62808, Flavobacterium ATCC21588 |
| | X74599 Synechococcus sp. Icy gene for lycopene cyclase |
| | X81787 *N. tabacum* CrtL-1 gene encoding lycopene cyclase |
| | X86221, *C. annuum* |

TABLE 3-continued

Sources of Genes Encoding the Lower Carotenoid Biosynthetic Pathway

| Gene | Genbank Accession Number and Source Organism |
|---|---|
| | X86452, *L. esculentum* mRNA for lycopene β-cyclase |
| | X95596, *S. griseus* |
| | X98796, *N. pseudonarcissus* |
| crtI | AB046992, *Citrus unshiu* CitPDS1 mRNA for phytoene desaturase, complete cds |
| | AF039585 *Zea mays* phytoene desaturase (pds1) gene promoter region and exon 1 |
| | AF049356 *Oryza sativa* phytoene desaturase precursor (Pds) mRNA, complete cds |
| | AF139916, *Brevibacterium linens* |
| | AF218415, Bradyrhizobium sp. ORS278 |
| | AF251014, *Tagetes erecta* |
| | AF364515, *Citrus x paradisi* |
| | D58420, *Agrobacterium aurantiacum* |
| | D83514, *Erythrobacter longus* |
| | L16237, *Arabidopsis thaliana* |
| | L37405, *Streptomyces griseus* geranylgeranyl pyrophosphate synthase (crtB), phytoene desaturase (cftE) and phytoene synthase (cftI) genes, complete cds |
| | L39266, *Zea mays* phytoene desaturase (Pds) mRNA, complete cds |
| | M64704, Soybean phytoene desaturase |
| | M88683, *Lycopersicon esculentum* phytoene desaturase (pds) mRNA, complete cds |
| | S71770, carotenoid gene cluster |
| | U37285, *Zea mays* |
| | U46919, *Solanum lycopersicum* phytoene desaturase (Pds) gene, partial cds |
| | U62808, Flavobacterium ATCC21588 |
| | X55289, Synechococcus pds gene for phytoene desaturase |
| | X59948, *L. esculentum* |
| | X62574, Synechocystis sp. pds gene for phytoene desaturase |
| | X68058 *C. annuum* pds1 mRNA for phytoene desaturase |
| | X71023 *Lycopersicon esculentum* pds gene for phytoene desaturase |
| | X78271, *L. esculentum* (Ailsa Craig) PDS gene |
| | X78434, *P. blakesleeanus* (NRRL1555) carB gene |
| | X78815, *N. pseudonarcissus* |
| | X86783, *H. pluvialis* |
| | Y14807, *Dunaliella bardawil* |
| | YI 5007, *Xanthophyllomyces dendrorhous* |
| | Y15112, *Paracoccus marcusii* |
| | Y15114, Anabaena PCC7210 crtP gene |
| | Z11165, *R. capsulatus* |
| crtB | AB001284, *Spirulina platensis* |
| | AB032797, *Daucus carota* PSY mRNA for phytoene synthase, complete cds |
| | AB034704, *Rubrivivax gelatinosus* |
| | AB037975, *Citrus unshiu* |
| | AF009954, *Arabidopsis thaliana* phytoene synthase (PSY) gene, complete cds |
| | AF139916, *Brevibacterium linens* |
| | AF152892, *Citrus x paradisi* |
| | AF218415, Bradyrhizobium sp. ORS278 |
| | AF220218, *Citrus unshiu* phytoene synthase (Psy1) mRNA, complete cds |
| | AJ010302, Rhodobacter |
| | AJ133724, *Mycobacterium aurum* |
| | AJ278287, *Phycomyces blakesleeanus* carRA gene for lycopene cyclase/phytoene synthase, |
| | AJ304825 *Helianthus annuus* mRNA for phytoene synthase (psy gene) |
| | AJ308385 *Helianthus annuus* mRNA for phytoene synthase (psy gene) |

TABLE 3-continued

Sources of Genes Encoding the Lower Carotenoid Biosynthetic Pathway

| Gene | Genbank Accession Number and Source Organism |
|---|---|
| | D58420, *Agrobacterium aurantiacum* |
| | L23424 |
| | *Lycopersicon esculentum* phytoene synthase (PSY2) mRNA, complete cds |
| | L25812, Arabidopsis |
| | L37405, *Streptomyces griseus* geranylgeranyl pyrophosphate synthase (crtB), phytoene desaturase (cftE) and phytoene synthase (cftI) genes, complete cds |
| | M38424 |
| | *Pantoea agglomerans* phytoene synthase (crtE) gene, complete cds |
| | M87280, *Pantoea agglomerans* |
| | S71770, carotenoid gene cluster |
| | U32636 |
| | *Zea mays* phytoene synthase (Y1) gene, complete cds |
| | U62808, Flavobacterium ATCC21588 |
| | U87626, *Rubrivivax gelatinosus* |
| | U91900, *Dunaliella bardawil* |
| | X52291, *Rhodobacter capsulatus* |
| | X60441, *L. esculentum* GTom5 gene for phytoene synthase |
| | X63873 |
| | Synechococcus PCC7942 pys gene for phytoene synthase |
| | X68017 |
| | *C. annuum* psy1 mRNA for phytoene synthase |
| | X69172 |
| | Synechocystis sp. pys gene for phytoene synthase |
| | X78814, *N. pseudonarcissus* |
| crtZ | D58420, *Agrobacterium aurantiacum* |
| | D58422, Alcaligenes sp. |
| | D90087, *E. uredovora* |
| | M87280, *Pantoea agglomerans* |
| | U62808, Flavobacterium ATCC21588 |
| | Y15112, *Paracoccus marcusli* |
| crtW | AF218415, Bradyrhizobium sp. ORS278 |
| | D45881, *Haematococcus pluvialis* |
| | D58420, *Agrobacterium aurantiacum* |
| | D58422, Alcaligenes sp. |
| | X86782, *H. pluvialis* |
| | Y15112, *Paracoccus marcusii* |
| crtO | X86782, *H. pluvialis* |
| | Y15112, *Paracoccus marcusii* |
| crtU | AF047490, *Zea mays* |
| | AF121947, *Arabidopsis thaliana* |
| | AF139916, *Brevibacterium linens* |
| | AF195507, *Lycopersicon esculentum* |
| | AF272737, *Streptomyces griseus* strain IFO13350 |
| | AF372617, *Citrus x paradisi* |
| | AJ133724, *Mycobacterium aurum* |
| | AJ224683, *Narcissus pseudonarcissus* |
| | D26095 and U38550, Anabaena sp. |
| | X89897, *C. annuum* |
| | Y15115, Anabaena PCC7210 crtQ gene |
| crtA (spheroidene monooxygenase) | AJ010302, *Rhodobacter sphaeroides* Z11165 and X52291, *Rhodobacter capsulatus* |
| crtC | AB034704, *Rubrivivax gelatinosus* |
| | AF195122 and AJ010302, *Rhodobacter sphaeroides* |
| | AF287480, *Chlorobium tepidum* |
| | U73944, *Rubrivivax gelatinosus* |
| | X52291 and Z11165, *Rhodobacter capsulatus* |
| | Z21955, *M. xanthus* |
| crtD (carotenoid 3, 4-desaturase | AJ010302 and X63204, *Rhodobacter sphaeroides* U73944, *Rubrivivax gelatinosus* X52291 and Z11165, *Rhodobacter capsulatus* |
| crtF (1-OH-carotenoid methylase) | AB034704, *Rubrivivax gelatinosus* AF288602, *Chloroflexus aurantiacus* AJ010302, *Rhodobacter sphaeroides* X52291 and Z11165, *Rhodobacter capsulatus* |

The most preferred source of genes for the lower carotenoid biosynthetic pathway in the present invention are from a variety of sources. The "ispA" gene (SEQ ID NO:19) is native to *Methylomonas* 16a, as the organism produces respiratory quinones and a 30-carbon carotenoid via the 2-C-methyl-D-erythritol 4-phosphate (MEP) pathway. However, *Methylomonas* does not synthesize the desired 40-carbon carotenoids. FPP is the end-product of the MEP pathway in *Methylomonas* 16A and is subsequently converted to its natural 30-carbon carotenoid by the action of the sqs, crtN1 and crtN2 gene products. As a native gene to the preferred host organism, the ispA gene (SEQ ID NO:19) is the most preferred source of the gene for the present invention.

The majority of the most preferred source of crt genes are primarily from *Panteoa stewartii*. Sequences of these preferred genes are presented as the following SEQ ID numbers: the crtE gene (SEQ ID NO:25), the crtX gene (SEQ ID NO:27), crtY (SEQ ID NO:29), the crtI gene (SEQ ID NO:31), the crtB gene (SEQ ID NO:33) and the crtZ gene (SEQ ID NO:35). Additionally, the crtO gene isolated from *Rhodococcus erythropolis* AN12 and presented as SEQ ID NO:37 is preferred in combination with other genes for the present invention.

By using various combinations of the genes presented in Table 3 and the preferred genes of the present invention, innumerable different carotenoids and carotenoid derivatives could be made using the methods of the present invention, provided sufficient sources of IPP are available in the host organism. For example, the gene cluster crtEXYIB enables the production of β-carotene. Addition of the crt Z to crtEXYIB enables the production of zeaxanthin, while the crt EXYIBZO cluster leads to production of astaxanthin and canthaxanthin.

It is envisioned that useful products of the present invention will include any carotenoid compound as defined herein including but not limited to antheraxanthin, adonixanthin, astaxanthin, canthaxanthin, capsorubin, β-cryptoxanthin alpha-carotene, beta-carotene, epsilon-carotene, echinenone, gamma-carotene, zeta-carotene, alpha-cryptoxanthin, diatoxanthin, 7,8-didehydroastaxanthin, fucoxanthin, fucoxanthinol, isorenieratene, lactucaxanthin, lutein, lycopene, neoxanthin, neurosporene, hydroxyneurosporene, peridinin, phytoene, rhodopin, rhodopin glucoside, siphonaxanthin, spheroidene, spheroidenone, spirilloxanthin, uriolide, uriolide acetate, violaxanthin, zeaxanthin-β-diglucoside, and zeaxanthin. Additionally the invention encompasses derivitization of these molecules to create hydroxy-, methoxy-, oxo-, epoxy-, carboxy-, or aldehydic functional groups, or glycoside esters, or sulfates.

Construction of Recombinant C1 Metabolizing Microorganisms

Methods for introduction of genes encoding the appropriate upper isoprene pathway genes or lower carotenoid biosynthetic pathway genes into a suitable C1 metabolizing host are common. Microbial expression systems and expression vectors containing regulatory sequences suitable for expression of heterologus genes in C1 metabolizing hosts are known. Any of these could be used to construct chimeric genes for expression of any of the above mentioned carotenoid biosynthetic genes. These chimeric genes could then be introduced into appropriate hosts via transformation to provide high level expression of the enzymes.

Vectors or cassettes useful for the transformation of suitable host cells are available. For example several classes of promoters may be used for the expression of genes encoding the present carotenoid biosynthetic genes in C1 metabolizers including, but not limited to endogenous promoters such as the deoxy-xylulose phosphate synthase or methanol dehydrogenase operon promoter (Springer et al. (1998) *FEMS Microbiol Lett* 160:119–124), the promoter for polyhydroxyalkanoic acid synthesis (Foellner et al. *Appl. Microbiol. Biotechnol.* (1993) 40:284–291), or promoters identified from native plasmids in methylotrophs (EP 296484). In addition to these native promoters, non-native promoters may also be used, as for example the promoter for the lactose operon Plac (Toyama et al. *Microbiology* (1997) 143:595–602; EP 62971) or a hybrid promoter such as Ptrc (Brosius et al. (1984) *Gene* 27:161–172). Similarly, promoters associated with antibiotic resistance, e.g. kanamycin (Springer et al. (1998) *FEMS Microbiol Lett* 160:119–124; Ueda et al. *Appl. Environ. Microbiol.* (1991) 57:924–926) or tetracycline (U.S. Pat. No. 4,824,786), are also suitable.

Once the specific regulatory element is selected, the promoter-gene cassette can be introduced into a C1 metabolizer on a plasmid containing either a replicon for episomal expression (Brenner et al. *Antonie Van Leeuwenhoek* (1991) 60:43–48; Ueda et al. *Appl. Environ. Microbiol.* (1991) 57:924–926) or homologous regions for chromosomal integration (Naumov et al. *Mol. Genet. Mikrobiol. Virusol.* (1986) 11:44–48).

Typically, the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Where accumulation of a specific carotenoid is desired it may be necessary to reduce or eliminate the expression of certain genes in the target pathway or in competing pathways that may serve as competing sinks for energy or carbon. Alternatively, it may be useful to over-express various genes upstream of desired carotenoid intermediates to enhance production.

Methods of up-regulating and down-regulating genes for this purpose have been explored. Where sequence of the gene to be disrupted is known, one of the most effective methods gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell. (See for example Hamilton et al. (1989) *J. Bacteriol.* 171:4617–4622, Balbas et al. (1993) *Gene* 136:211–213, Gueldener et al. (1996) *Nucleic Acids Res.* 24:2519–2524, and Smith et al. (1996) *Methods Mol. Cell. Biol.* 5:270–277.)

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to a UV radiation and then screened for the desired phenotype. Mutagenesis with chemical agents is also effective for generating mutants and commonly used substances include chemicals that affect non-replicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992).

Another non-specific method of gene disruption is the use of transposoable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element.

In the context of the present invention the disruption of certain genes in the terpenoid pathway may enhance the accumulation of specific carotenoids however, the decision of which genes to disrupt would need to be determined on an empirical basis. Candidate genes may include one or more of the prenyltransferase genes which, as described earlier, which catalyze the successive condensation of isopentenyl diphosphate resulting in the formation of prenyl diphosphates of various chain lengths (multiples of C-5 isoprene units). Other candidate genes for disruption would include any of those which encode proteins acting upon the terpenoid backbone prenyl diphosphates.

Similarly, over-expression of certain genes upstream of the desired product will be expected to have the effect of increasing the production of that product. For example, may of the genes in the upper isoprenoid pathway (D-1-deoxyxylulose-5-phosphate synthase (Dxs), D-1-deoxyxylulose-5-phosphate reductoisomerase (Dxr), 2C-methyl-d-erythritol cytidylyltransferase (IspD), 4-diphosphocytidyl-2-C-methylerythritol kinase (IspE), 2C-methyl-d-erythritol 2,4-cyclodiphosphate synthase (IspF), CTP synthase (PyrG) and lytB) could be expressed on multicopy plasmids, or under the influence of strong non-native promoters. In this fashion the levels of desired carotenoids may be enhanced.

Industrial Production of Carotenoids

Where commercial production of carotenoid compounds is desired according to the present invention, a variety of culture methodologies may be applied. For example, large-scale production of a specific gene product, over-expressed from a recombinant microbial host may be produced by both batch or continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

Commercial production of carotenoids using C1 metabolizers may also be accomplished with a continuous culture. A continuous culture is an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates for C1 metabolizing organisms. Suitable substrates may include but are not limited to one-carbon substrates such as carbon dioxide, methane or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415–32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485–489 (1990)). Hence it is contemplated that the source of carbon utilized in the present invention may encompass a wide variety of carbon containing substrates and will only be limited by the choice of organism.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial*

*Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. In any case where GCG program parameters were not prompted for, in these or any other GCG program, default values were used.

The meaning of abbreviations is as follows: "h" means hour(s), "min" means minute(s), "sec" means second(s), "d" means day(s), "mL" means milliliters, "L" means liters.

Microbial Cultivation, Preparation of Cell Suspensions, and Associated Analyses for *Methylomonas* 16a The following conditions were used throughout the experimental Examples for treatment of *Methylomonas* 16a, unless conditions were specifically specified otherwise.

*Methylomonas* 16a is typically grown in serum stoppered Wheaton bottles (Wheaton Scientific, Wheaton Ill.) using a gas/liquid ratio of at least 8:1 (i.e. 20 mL of Nitrate liquid "BTZ-3" media of 160 mL total volume). The standard gas phase for cultivation contained 25% methane in air. These conditions comprise growth conditions and the cells are referred to as growing cells. In all cases, the cultures were grown at 30° C. with constant shaking in a Lab-Line rotary shaker unless otherwise specified.

Nitrate Medium for *Methylomonas* 16A

Nitrate liquid medium, also referred to herein as "defined medium" or "BTZ-3" medium was comprised of various salts mixed with Solution 1 as indicated below (Tables 4 and 5) or where specified the nitrate was replaced with 15 mM ammonium chloride. Solution 1 provides the comosition for 100 fold concentrated stock solution of trace minerals.

TABLE 4

Solution 1*

|  | MW | Conc. (mM) | g per L |
|---|---|---|---|
| Nitriloacetic acid | 191.1 | 66.9 | 12.8 |
| $CuCl_2 \times 2H_2O$ | 170.48 | 0.15 | 0.0254 |
| $FeCl_2 \times 4H_2O$ | 198.81 | 1.5 | 0.3 |
| $MnCl_2 \times 4H_2O$ | 197.91 | 0.5 | 0.1 |
| $CoCl_2 \times 6H_2O$ | 237.9 | 1.31 | 0.312 |
| $ZnCl_2$ | 136.29 | 0.73 | 0.1 |
| $H_3BO_3$ | 61.83 | 0.16 | 0.01 |
| $Na_2MoO_4 \times 2H_2O$ | 241.95 | 0.04 | 0.01 |
| $NiCl_2 \times 6H_2O$ | 237.7 | 0.77 | 0.184 |

*Mix the gram amounts designated above in 900 mL of $H_2O$, adjust to pH = 7, and add $H_2O$ to an end volume of 1 L. Keep refrigerated.

TABLE 5

Nitrate liquid medium (BTZ-3)**

|  | MW | Conc. (mM) | g per L |
|---|---|---|---|
| $NaNO_3$ | 84.99 | 10 | 0.85 |
| $KH_2PO_4$ | 136.09 | 3.67 | 0.5 |
| $Na_2SO_4$ | 142.04 | 3.52 | 0.5 |
| $MgCl_2 \times 6H_2O$ | 203.3 | 0.98 | 0.2 |
| $CaCl_2 \times 2H_2O$ | 147.02 | 0.68 | 0.1 |
| 1 M HEPES (pH 7) | 238.3 |  | 50 mL |
| Solution 1 |  |  | 10 mL |

**Dissolve in 900 mL $H_2O$. Adjust to pH = 7, and add $H_2O$ to give 1 L. For agar plates: Add 15 g of agarose in 1 L of medium, autoclave, let cool down to 50° C., mix, and pour plates.

Assessment of Microbial Growth and Conditions for Harvesting Cells

Cells obtained for experimental purposes were allowed to grow to maximum optical density (O.D. 660~1.0). Harvested cells were obtained by centrifugation in a Sorval RC-5B centrifuge using a SS-34 rotor at 6000 rpm for 20 min. These cell pellets were resuspended in 50 mM HEPES buffer pH 7. These cell suspensions are referred to as washed, resting cells.

Microbial growth was assessed by measuring the optical density of the culture at 660 nm in an Ultrospec 2000 UV/Vis spectrophotometer (Pharmacia Biotech, Cambridge England) using a 1 cm light path cuvet. Alternatively microbial growth was assessed by harvesting cells from the culture medium by centrifugation as described above and, resuspending the cells in distilled water with a second centrifugation to remove medium salts. The washed cells were then dried at 105° C. overnight in a drying oven for dry weight determination.

Methane concentration was determined as described by Emptage et al. (1997 *Env. Sci. Technol.* 31:732–734), hereby incorporated by reference.

Nitrate and Nitrite Assays 1 mL samples of cell culture were taken and filtered through a 0.2 micron Acrodisc filter to remove cells. The filtrate from this step contains the nitrite or nitrate to be analyzed. The analysis was performed on a Dionex ion chromatograph 500 system (Dionex, Sunnyvale Calif.) with an AS3500 autosampler. The column used was a 4 mm Ion-Pac AS11-HC separation column with an AG-AC guard column and an ATC trap column. All columns are provided by Dionex.

The mobile phase was a potassium hydroxide gradient from 0 to 50 mM potassium hydroxide over a 12 min time interval. Cell temperature was 35° C. with a flow rate of 1 mL/min.

HPLC Analysis of Carotenoid Content

Cell pellets were extracted with 1 ml acetone by vortexing for 1 min and intermittent vortexing over the next 30 min. Cell debris was removed by centrifugation at 14,000×g for 10 min and the supernatants was collected and passed through a 0.45 $\mu$M filter. A Beckman System Gold® HPLC with Beckman Gold Nouveau Software (Columbia, Md.) was used for the study. The crude extraction (0.1 mL) was loaded onto a 125×4 mm RP8 (5 $\mu$m particles) column with corresponding guard column (Hewlett-Packard, San Fernando, Calif.). The flow rate was 1 mL/min, while the solvent program used was: 0–11.5 min 40% water/60% methanol; 11.5–20 min 100% methanol; 20–30 min 40% water/60% methanol. The spectral data was collected by a Beckman photodiode array detector (model 168).

Example 1

Isolation and Sequencing of *Methylomonas* 16a

The original environmental sample containing the isolate was obtained from pond sediment. The pond sediment was inoculated directly into defined medium with ammonium as nitrogen source under 25% methane in air. Methane was the sole source of carbon and energy. Growth was followed until the optical density at 660 nm was stable, whereupon the culture was transferred to fresh medium such that a 1:100 dilution was achieved. After 3 successive transfers with methane as sole carbon and energy source, the culture was plated onto growth agar with ammonium as nitrogen source and incubated under 25% methane in air. Many methanotrophic bacterial species were isolated in this manner. However, *Methylomonas* 16a was selected as the organism to study due to its rapid growth of colonies, large colony size, ability to grow on minimal media, and pink pigmentation indicative of an active biosynthetic pathway for carotenoids.

Genomic DNA was isolated from *Methylomonas* 16a according to standard protocols. Genomic DNA and library construction were prepared according to published protocols (Fraser et al., The Minimal Gene Complement of *Mycoplasma genitalium; Science* 270 (5235):397–403 (1995)). A cell pellet was resuspended in a solution containing 100 mM Na-EDTA pH 8.0, 10 mM Tris-HCl pH 8.0, 400 mM NaCl, and 50 mM $MgCl_2$.

Genomic DNA preparation After resuspension, the cells were gently lysed in 10% SDS, and incubated for 30 min at 55° C. After incubation at room temperature, proteinase K was added to 100 µg/mL and incubated at 37° C. until the suspension was clear. DNA was extracted twice with Tris-equilibrated phenol and twice with chloroform. DNA was precipitated in 70% ethanol and resuspended in a solution containing 10 mM Tris-HCl and 1 mM Na-EDTA (TE), pH 7.5. The DNA solution was treated with a mix of RNAases, then extracted twice with Tris-equilibrated phenol and twice with chloroform. This was followed by precipitation in ethanol and resuspension in TE.

Library construction 200 to 500 µg of chromosomal DNA was resuspended in a solution of 300 mM sodium acetate, 10 mM Tris-HCl, 1 mM Na-EDTA, and 30% glycerol, and sheared at 12 psi for 60 sec in an Aeromist Downdraft Nebulizer chamber (IBI Medical products, Chicago, Ill.). The DNA was precipitated, resuspended and treated with Bal31 nuclease. After size fractionation, a fraction (2.0 kb, or 5.0 kb) was excised and cleaned, and a two-step ligation procedure was used to produce a high titer library with greater than 99% single inserts.

Sequencing A shotgun sequencing strategy approach was adopted for the sequencing of the whole microbial genome (Fleischmann, R. et al., Whole-Genome Random sequencing and assembly of *Haemophilus influenzae* Rd *Science* 269(5223):496–512 (1995)). Sequence was generated on an ABI Automatic sequencer using dye terminator technology (U.S. Pat. No. 5,366,860; EP 272,007) using a combination of vector and insert-specific primers. Sequence editing was performed in either DNAStar (DNA Star Inc.) or the Wisconsin GCG program (Wisconsin Package Version 9.0, Genetics Computer Group (GCG), Madison, Wis.) and the CONSED package (version 7.0). All sequences represent coverage at least two times in both directions.

Example 2

Identification and Characterization of Bacterial Genes from *Methylomonas*

All sequences from Example 1 were identified by conducting BLAST (Basic Local Alignment Search Tool; Altschul, S. F., et al., (1993) *J. Mol. Biol.* 215:403–410; see also www.ncbi.nim.nih.gov/BLAST/) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases). The sequences were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. All comparisons were done using either the BLASTNnr or BLASTXnr algorithm.

The results of these BLAST comparisons are given below in Table 6 for many critical genes of the present invention. Table 6 summarizes the sequence to which each *Methylomonas* gene has the most similarity (presented as % similarities, % identities, and expectation values). The table displays data based on the BLASTXnr algorithm with values reported in expect values. The Expect value estimates the statistical significance of the match, specifying the number of matches, with a given score, that are expected in a search of a database of this size absolutely by chance.

TABLE 6

Identification of Critical Methylomonas Genes Based on Sequence Homology

| Gene Name | Similarity Identified | SEQ ID | SEQ ID peptide | % Identity[a] | % Similarity[b] | E-value[c] | Citation |
|---|---|---|---|---|---|---|---|
| Phosphofructokinase pyrophosphate dependent | Phosphofructokinase pyrophosphate dependent gi\|150931\|gb\|AAA25675.1\|(M67447) | 1 | 2 | 63% | 83% | 1.7e-97 | Ladror et al., J. Biol. Chem. 266, 16550–16555 (1991) |
| KHG/KDPG | (AL352972) KHG/KDPG aldolase Streptomyces coelicolor | 3 | 4 | 59% | 72% | 1e-64 | Redenbach et al., Mol. Microbiol. 21 (1), 77–96 (1996) |
| dxs | 1-deoxyxylulose-5-phosphate synthase (*E. coli*) | 5 | 6 | 60% | 86% | 5.7e-149 | Lois et al., Proc. Natl. Acad. Sci. USA. 95 (5), 2105–2110 (1998) |

TABLE 6-continued

Identification of Critical Methylomonas Genes Based on Sequence Homology

| Gene Name | Similarity Identified | SEQ ID | SEQ ID peptide | % Identity[a] | % Similarity[b] | E-value[c] | Citation |
|---|---|---|---|---|---|---|---|
| dxr | 1-deoxy-d-xylulose 5-phosphate reductoisomerase (*E. coli*) | 7 | 8 | 55% | 78% | 3.3e-74 | Takahashi et al., Proc. Natl. Acad. USA 95:9879–9884 (1998) |
| ygbP/ispD | 2C-methyl-d-erythritol cytidylyltransferase (*E. coli*) | 9 | 10 | 52% | 74% | 7.7e-36 | Rohdich et al., Proc Natl Acad Sci USA 1999 Oct 12;96(21):11758–63 |
| ychB/IspE | 4-diphosphocytidyl-2-C-methylerythritol kinase (*E. coli*) | 11 | 12 | 50% | 73% | 8.8e-49 | Luttgen et al., Proc Natl Acad Sci USA.2000 Feb 1;97(3):1062–7. |
| ygbB/ispF | 2C-methyl-d-erythritol 2,4-cyclodiphosphate synthase (*E. coli*) | 13 | 14 | 69% | 84% | 1.6e-36 | Herz et al., Proc Natl Acad Sci U S A 2000 Mar 14;97(6):2486–90 |
| pyrG | CTP synthase (*E. coli*) | 15 | 16 | 67% | 89% | 2.4e-141 | Weng. et al., J. Biol. Chem. 261:5568–5574 (1986) |
| lytB | *Acinetobacter* sp BD413 Putative penicillin binding protein | 17 | 18 | 65 | 87 | 3.4e-75 | Genbank# G.I. 5915671 |
| lspA | Geranyltranstransferase (also farnesyl-diphosphate synthase) (*Synechococcus elongatus*) | 19 | 20 | 57% | 78% | 7.8e-56 | Ohto,et al., Plant Mol. Biol. 40 (2), 307–321 (1999) |
| crtN1 | diapophytoene dehydrogenase CrtN-copy 1 (*Heliobacillus mobilis*) | 21 | 22 | 34% | 72% | 4e-66 | Xiong, et al., .Proc. Natl. Acad. Sci. U.S.A. 95 (25), 14851–14856 (1998) |
| crtN2 | Diapophytoene dehydrogenase CrtN-copy 2 (*Staphylococcus aureus*) | 23 | 24 | 49% | 78% | 1.3e-76 | Genbank #: X97985 |

Example 3

Microarray for Gene Expression in *Methylomonas* 16a

All bacterial ORFs of *Methylomonas* were prepared for DNA microarray. The following Example presents the specific protocols utilized for microarray analysis.

Amplification of DNA regions for the construction of DNA microarray.

Specific primer pairs were used to amplify each protein specifying ORF of *Methylomonas* sp. strain 16a. Genomic DNA (10–30 ng) was used as the template. The PCR reactions were performed in the presence of HotStart Taq™ DNA polymerase (Qiagen, Valencia, Calif.) and dNTPs (Gibco BRL Life Science Technologies, Gaithersberg, Md.). Thirty-five cycles of denaturation at 95° C. for 30 sec, annealing at 55° C. for 30 sec, and polymerization at 72° C. for 2 min were conducted. The quality of PCR reactions was checked with electrophresis in a 1% argarose gel. The DNA samples were purified by the high-throughput PCR purification kit from Qiagen.

Arraying amplified ORFs. Before arraying, an equal volume of DMSO (10 μL) and DNA (10 μL) sample was mixed in 384-well microtiter plates. A generation II DNA spotter (Molecular Dynamics, Sunnyvale, Calif.) was used to array the samples onto coated glass slides (Telechem, Sunnyvale, Calif.). Each PCR product was arrayed in duplicate on each slide. After cross-linking by UV light, the slides were stored under vacuum in a desiccator at room temperature.

RNA Isolation. *Methylomonas* 16a was cultured in a defined medium with ammonium or nitrate (10 mM) as a nitrogen source under 25% methane in air. Samples of the minimal medium culture were harvested when the O.D. reached 0.3 at $A_{600}$ (exponential phase). Cell cultures were harvested quickly and ruptured in RLT buffer (Qiagen RNeasy Mini Kit, Valencia, Calif.) with a beads-beater (Bio101, Vista, Calif.). Debris was pelleted by centrifugation for 3 min at 14,000×g at 4° C. RNA isolation was completed using the protocol supplied with this kit. After on-column DNAase treatment, the RNA product was eluted with 50–100 μL RNAase-free water. RNA preparations were stored frozen at either −20 or −80° C.

Synthesis of fluorescent cDNA from total RNA. RNA samples (7 to 15 μg) and random hexamer primers (6 μg; Gibco BRL, Gaithersburg, Md.) were diluted with RNAase-free water to a volume of 25 μL. The sample was denatured at 70° C. for 10 min and then chilled on ice for 30 sec. After adding 14 μL of labeling mixture, the annealing was accomplished by incubation at room temperature for 10 min. The labeling mixture contained 8 μL of 5× enzyme buffer, 4 μL DTT (0.1 M), and 2 μL of 20× dye mixture. The dye mixture consisted of 2 mM of each dATP, dGTP, and dTTP, 1 mM dCTP, and 1 mM of Cy3-dCTP or Cy5-dCTP. After adding 1 to 1.5 µL of SuperScript II reverse transcriptase (200 units/mL, Life Technologies Inc., Gaithersburg, Md.), cDNA synthesis was allowed to proceed at 42° C. for 2 hr. The RNA was removed by adding 2 µL NaOH (2.5 N) to the reaction. After 10 min of incubation at 37° C., the pH was adjusted with 10 µL of HEPES (2 M). The labeled cDNA was then purified with a PCR purification kit (Qiagen, Valencia, Calif.). Labeling efficiency was monitored using either $A_{550}$ for Cy3 incorporation, or $A_{650}$ for Cy5.

Fluorescent labeling of genomic DNA. Genomic DNA was nebulized to approximately 2 kb pair fragments. Genomic DNA (0.5 to 1 µg) was mixed with 6 µg of random hexamers primers (Gibco BRL Life Science Technologies, Gaithersburg, Md.) in 15 µL of water. The mix was denatured by placement in boiling water for 5 min, followed by annealing on ice for 30 sec before transfer to room temperature. Then, 2 µL 5× Buffer 2 (Gibco BRL) and 2 ul dye mixture were added. The components of the dye mixture and the labeling procedure are the same as described above for RNA labeling, except that the Klenow fragment of DNA polymerase 1 (5 µg/µL, Gibco BRL) was used as the enzyme. After incubation at 37° C. for 2 hr, the labeled DNA probe was purified using a PCR purification kit (Qiagen, Valencia, Calif.).

Hybridization and washing. Slides were first incubated with prehybridization solution containing 3.5×SSC (Gibco BRL, Gaithersburg, Md.), 0.1% SDS (Gibco BRL), 1% bovine serum albumin (BSA, Fraction V, Sigma, St. Louis, Mo.). After prehybridization, hybridization solutions (Molecular Dynamics, Sunnyvale, Calif.) containing labeled probes were added to slides and covered with cover slips. Slides were placed in a humidified chamber in a 42° C. incubator. After overnight hybridization, slides were initially washed for 5 min at room temperature with a washing solution containing 1×SSC, 0.1% SDS and 0.1×SSC, 0.1% SDS. Slides were then washed at 65° C. for 10 min with the same solution for three times. After washing, the slides were dried with a stream of nitrogen gas.

Data Collection and Analysis. The signal generated from each slide was quantified with a laser scanner (Molecular Dynamics, Sunnyvale, Calif.). The images were analyzed with ArrayVision 4.0 software (Imaging Research, Inc., Ontario, Canada). The raw fluorescent intensity for each spot was adjusted by subtracting the background. These readings were exported to a spreadsheet for further analysis.

Example 4

Comparison of Gene Expression Levels in the Entner Douderoff Pathway as Compared with the Embeden Meyerof Pathway This Example presents microarray evidence demonstrating the use of the Embden-Meyerhoff pathway for carbon metabolism in the 16a strain.

FIG. 2 shows the relative levels of expression of genes for the Entner-Douderoff pathway and the Embden-Meyerhoff pathway. The relative transcriptional activity of each gene was estimated with DNA microarray as described previously (Example 3; Wei, et al., *J. Bact.* 183:545–556 (2001)).

Specifically, a single DNA microarray containing 4000 ORFs (open reading frames) of *Methylomonas* 16a was hybridized with probes generated from genomic DNA and total RNA. The genomic DNA of 16a was labeled with the Klenow fragment of DNA polymerase and fluorescent dye Cy-5, while the total RNA was labeled with reverse transcriptase and Cy-3. After hybridization, the signal intensities of both Cy-3 and Cy-5 for each spot in the array were quantified. The intensity ratio of Cy-3 and Cy-5 was then used to calculate the fraction of each transcript (as a percentage), according to the following formula: (gene ratio/sum of all ratio)×100. The value obtained reflects the relative abundance of mRNA of an individual gene. Accordingly, transcriptional activity of all the genes represented by the array can be ranked based on its relative mRNA abundance in a descending order. The numbers in FIG. 2 next to each step indicate the relative expression level of that enzyme. For example, mRNA abundance for the methane monooxygenase was the most highly expressed enzyme in the cell (ranked #1) because its genes had the highest transcriptional activity when the organism was grown with methane as the carbon source (FIG. 2). The next most highly expressed enzyme is methanol dehydrogenase (ranked #2). The hexulose-monophosphate synthase gene is one of the ten most highly expressed genes in cells grown on methane.

The genes considered "diagnostic" for Entner-Douderoff pathway are the 6-phosphogluconate dehydratase and the 2 keto-3-deoxy-6-phosphogluconate aldolase. In contrast, the phosphofructokinase and fructose bisphosphate aldolase are "diagnostic" of the Embden-Meyerhoff sequence. Messenger RNA transcripts of phosphofructokinase (ranked #232) and fructose bisphosphate aldolase (ranked #65) were in higher abundance than those for glucose 6 phosphate dehydrogenase (ranked #717), 6 phosphogluconate dehydratase (ranked #763) or the 2-keto-3-deoxy-6-gluconate aldolase. The data suggests that the Embden-Meyerhoff pathway enzymes are more strongly expressed than the Entner-Douderoff pathway enzymes. This result is surprising and counter to existing beliefs on the central metabolism of methanotrophic bacteria (Dijkhuizen, L., et al. The physiology and biochemistry of aerobic methanol-utilizing gram-negative and gram-positive bacteria. In: *Methane and Methanol Utilizers, Biotechnology Handbooks* 5. 1992. Eds: Colin Murrell, Howard Dalton; pp 149–157).

Example 5

Direct Enzymatic Evidence for a Pyrophosphate-Linked Phosphofructokinase

This example shows the evidence for the presence of a pyrophosphate-linked phosphofructokinase enzyme in the current strain, thereby confirming the functionality of the Embden-Meyerhoff pathway in the present *Methylomonas* strain.

Phosphofructokinase activity was shown to be present in *Methylomonas* 16a by using the coupled enzyme assay described below. Assay conditions are given in Table 7 below.

Coupled Assay Reactions

Phosphofructokinase reaction is measured by a coupled enzyme assay. Phosphofructokinase reaction is coupled with fructose 1,6, biphosphate aldolase followed by triosephosphate isomerase. The enzyme activity is measured by the disappearance of NADH.

Specifically, the enzyme phosphofructokinase catalyzes the key reaction converting fructose 6 phosphate and pyrophosphate to fructose 1,6 bisphosphate and orthophosphate. Fructose-1,6-bisphosphate is cleaved to 3-phosphoglyceraldehyde and dihydroxyacetonephosphate by fructose 1,6-bisphosphate aldolase. Dihydroxyacetone-phosphate is isomerized to 3-phosphoglyceraldehyde by triosephosphate isomerase. Glycerol phosphate dehydrogenase plus NADH and 3-phosphoglyceraldehyde yields the alcohol glycerol-3-phosphate and NAD. Disappearance of NADH is monitored at 340 nm using spectrophotometer (UltraSpec 4000, Pharmacia Biotech).

TABLE 7

Assay Protocol

| Reagent | Stock solution (mM) | Volume (μl) per 1 mL total reaction volume | Final assay concentration (mM) |
|---|---|---|---|
| Tris-HCl pH 7.5 | 1000 | 100 | 100 |
| $MgCl_2.2H_2O$ | 100 | 35 | 3.5 |
| $Na_4P_2O_7.10H_2O$ or ATP | 100 | 20 | 2 |
| Fructose-6-phophate | 100 | 20 | 2 |
| NADH | 50 | 6 | 0.3 |
| Fructose bisphosphate aldolase | 100 (units/mL) | 20 | 2 (units) |
| Triose phosphate isomerase/glycerol phosphate dehydrogenase | (7.2 units/μl) (0.5 units/μl) | 3.69 | 27 units 1.8 units |
| KCl | 1000 | 50 | 50 |
| H2O | | adjust to 1 mL | |
| Crude extract | | 0–50 | |

This coupled enzyme assay was further used to assay the activity in a number of other methanotrophic bacteria as shown below in Table 8. The data in Table 8 shows known ATCC strains tested for phosphofructokinase activity with ATP or pyrophosphate as the phosphoryl donor. These organisms were classified as either a Type I or Type X ribulose monophosphate-utilizing strains or a Type II serine utilizer. Established literature makes these types of classifications based on the mode of carbon incorporation, morphology, % GC content and the presence or absence of key specific enzymes in the organism.

TABLE 8

Comparison Of Pyrophosphate Linked And ATP Linked Phosphofructokinase Activity In Different Methanotrophic Bacteria

| Strain | Assimilation Type Pathway | | ATP-PFK umol NADH/ min/mg | Ppi-PFK umol NADH/ min/mg |
|---|---|---|---|---|
| Methylomonas 16a ATCC PTA 2402 | I | Ribulose monophosphate | 0 | 2.8 |
| Methylomonas agile ATCC 35068 | I | Ribulose monophosphate | 0.01 | 3.5 |
| Methylobacter Whittenbury ATCC 51738 | I | Ribulose monophosphate | 0.01 | 0.025 |
| Methylomonas clara ATCC 31226 | I | Ribulose monophosphate | 0 | 0.3 |
| Methylomicrobium albus ATCC 33003 | I | Ribulose monophosphate | 0.02 | 3.6 |
| Methylococcus capsulatus ATCC 19069 | X | Ribulose monophosphate | 0.01 | 0.04 |
| Methylosinus sporium ATCC 35069 | II | Serine | 0.07 | 0.4 |

Several conclusions may be drawn from the data presented above. First, it is clear that ATP (which is the typical phosphoryl donor for phosphofructokinase) is essentially ineffective in the phosphofructokinase reaction in methanotrophic bacteria. Only inorganic pyrophosphate was found to support the reaction in all methanotrophs tested. Secondly, not all methanotrophs contain this activity. The activity was essentially absent in *Methylobacter whittenbury* and in *Methylococcus capsulatus*. Intermediate levels of activity were found in *Methylomonas clara* and *Methylosinus sporium*. These data show that many methanotrophic bacteria may contain a hitherto unreported phosphofructokinase activity. It may be inferred from this that methanotrophs containing this activity have an active Embden-Meyerhoff pathway.

Example 6

Cloning of Carotenoid Genes from Pantoea stewartii

Primers were designed using the sequence from *Pantoea ananatis* to amplify a fragment by PCR containing a crt cluster of genes. These sequences included 5'-3':

```
ATGACGGTCTGCGCAAAAAAACACG    SEQ ID NO:43

GAGAAATTATGTTGTGGATTTGGAATGC    SEQ ID NO:44
```

Chromosomal DNA was purified from *Pantoea stewatii* (ATCC no. 8199) and Pfu Turbo polymerase (Stratagene, La Jolla, Calif.) was used in a PCR amplifcation reaction under the following conditions: 94° C., 5 min; 94° C. (1 min)-60° C. (1 min)-72° C. (10 min) for 25 cycles, and 72° C. for 10 min. A single product of approximately 6.5 kb was observed following gel electrophoresis. Taq polymerase (Perkin Elmer) was used in a ten min 72° C. reaction to add additional 3' adenoside nucleotides to the fragment for TOPO cloning into pCR4-TOPO (Invitrogen, Carlsbad, Calif.). Following transformation to *E. coli* DH5α (Life Technologies, Rockville, Md.) by electroporation, several colonies appeared to be bright yellow in color, indicating that they were producing a carotenoid compound. Following plasmid isolation as instructed by the manufacturer using the Qiagen (Valencia, Calif.) miniprep kit, the plasmid containing the 6.5 kb amplified fragment was transposed with pGPS1.1 using the GPS-1 Genome Priming System kit (New England Biolabs, Inc., Beverly, Mass.). A number of these transposed plasmids were sequenced from each end of the transposon. Sequence was generated on an ABI Automatic sequencer using dye terminator technology (U.S. Pat. No. 5,366,860; EP 272007) using transposon specific primers. Sequence assembly was performed with the Sequencher program (Gene Codes Corp., Ann Arbor Mich.).

Example 7

Cloning of *Rhodococcus erythropolis* crtO

The present example describes the isolation, sequencing, and identification of a carotenoid biosynthetic pathway gene from *Rhodococcus erythropolis* AN12.
Isolation and Characterization of Strain AN12

Strain AN12 of *Rhodococcus erythropolis* was isolatd on the basis of being able to grow on aniline as the sole source of carbon and energy. Bacteria that grew on aniline were isolated from an enrichment culture. The enrichment culture was established by inoculating 1 ml of activated sludge into 10 ml of S12 medium (10 mM ammonium sulfate, 50 mM potassium phosphate buffer (pH 7.0), 2 mM $MgCl_2$, 0.7 mM $CaCl_2$, 50 μM $MnCl_2$, 1 μM $FeCl_3$, 1 μM $ZnCl_3$, 1.72 μM CuSO$_4$, 2.53 µM CoCl$_2$, 2.42 µM Na$_2$MoO$_2$, and 0.0001% FeSO$_4$) in a 125 ml screw cap Erlenmeyer flask. The activated sludge was obtained from a wastewater treatment facility. The enrichment culture was supplemented with 100 ppm aniline added directly to the culture medium and was incubated at 25° C. with reciprocal shaking. The enrichment culture was maintained by adding 100 ppm of aniline every 2–3 days. The culture was diluted every 14 days by replacing 9.9 ml of the culture with the same volume of S12 medium. Bacteria that utilized aniline as a sole source of carbon and energy were isolated by spreading samples of the enrichment culture onto S12 agar. Aniline (5 µL) was placed on the interior of each petri dish lid. The petri dishes were sealed with parafilm and incubated upside down at room temperature (approximately 25° C.). Representative bacterial colonies were then tested for the ability to use aniline as a sole source of carbon and energy. Colonies were transferred from the original S12 agar plates used for initial isolation to new S12 agar plates and supplied with aniline on the interior of each petri dish lid. The petri dishes were sealed with parafilm and incubated upside down at room temperature (approximately 25° C.).

The 16S rRNA genes of each isolate were amplified by PCR and analyzed as follows. Each isolate was grown on R2A agar (Difco Laboratories, Bedford, Mass.). Several colonies from a culture plate were suspended in 100 µl of water. The mixture was frozen and then thawed once. The 16S rRNA gene sequences were amplified by PCR using a commercial kit according to the manufacturer's instructions (Perkin Elmer) with primers HK12 (5'-GAGTTTGATCCTGGCTCAG-3') (SEQ ID NO:45) and HK13 (5'-TACCTTGTTACGACTT-3') (SEQ ID NO:46). PCR was performed in a Perkin Elmer GeneAmp 9600 (Norwalk, Conn.). The samples were incubated for 5 min at 94° C. and then cycled 35 times at 94° C. for 30 sec, 55° C. for 1 min, and 72° C. for 1 min. The amplified 16S rRNA genes were purified using a commercial kit according to the manufacturer's instructions (QIAquick PCR Purification Kit, Qiagen, Valencia, Calif.) and sequenced on an automated ABI sequencer. The sequencing reactions were initiated with primers HK12, HK13, and HK14 (5'-GTGCCAGCAGYMGCGGT-3') (SEQ ID NO:47, where Y=C or T, M=A or C). The 16S rRNA gene sequence of each isolate was used as the query sequence for a BLAST search (Altschul, et al., *Nucleic Acids Res.* 25:3389–3402(1997)) of GenBank for similar sequences.

A 16S rRNA gene of strain AN12 was sequenced and compared to other 16S rRNA sequences in the GenBank sequence database. The 16S rRNA gene sequence from strain AN12 was at least 98% similar to the 16S rRNA gene sequences of high G+C Gram positive bacteria belonging to the genus *Rhodococcus*.

Preparation of Genomic DNA for Sequencing and Sequence Generation

Genomic DNA preparation. *Rhodococcus erythropolis* AN12 was grown in 25 mL NBYE medium (0.8% nutrient broth, 0.5% yeast extract, 0.05% Tween 80) till mid-log phase at 37° C. with aeration. Bacterial cells were centrifuged at 4,000 g for 30 min at 4° C. The cell pellet was washed once with 20 ml 50 mM Na$_2$CO$_3$ containing 1M KCl (pH 10) and then with 20 ml 50 mM NaOAc (pH 5). The cell pellet was gently resuspended in 5 ml of 50 mM Tris-10 mM EDTA (pH 8) and lysozyme was added to a final concentration of 2 mg/mL. The suspension was incubated at 37° C. for 2 h. Sodium dodecyl sulfate was then added to a final concentration of 1% and proteinase K was added to 100 µg/ml final concentration. The suspension was incubated at 55° C. for 5 h. The suspension became clear and the clear lysate was extracted with equal volume of phenol:chloroform:isoamyl alcohol (25:24:1). After centrifuging at 17,000 g for 20 min, the aqueous phase was carefully removed and transferred to a new tube. Two volumes of ethanol were added and the DNA was gently spooled with a sealed glass pasteur pipet. The DNA was dipped into a tube containing 70% ethanol, then air dried. After air drying, DNA was resuspended in 400 µl of TE (10 mM Tris-1 mM EDTA, pH 8) with RNaseA (100 µg/mL) and stored at 4° C.

Library construction. 200 to 500 µg of chromosomal DNA was resuspended in a solution of 300 mM sodium acetate, 10 mM Tris-HCl, 1 mM Na-EDTA, and 30% glycerol, and sheared at 12 psi for 60 sec in an Aeromist Downdraft Nebulizer chamber (IBI Medical products, Chicago, Ill.). The DNA was precipitated, resuspended and treated with Bal31 nuclease (New England Biolabs, Beverly, Mass.). After size fractionation by 0.8% agarose gel electrophoresis, a fraction (2.0 kb, or 5.0 kb) was excised, cleaned and a two-step ligation procedure was used to produce a high titer library with greater than 99% single inserts.

Sequencing. A shotgun sequencing strategy approach was adopted for the sequencing of the whole microbial genome (Fleischmann, Robert et al., Whole-Genome Random sequencing and assembly of *Haemophilus influenzae* Rd *Science*, 269:1995).

Sequence was generated on an ABI Automatic sequencer using dye terminator technology (U.S. Pat. No. 5,366,860; EP 272007) using a combination of vector and insert-specific primers. Sequence editing was performed in either DNAStar (DNA Star Inc., Madison, Wis.) or the Wisconsin GCG program (Wisconsin Package Version 9.0, Genetics Computer Group (GCG), Madison, Wis.) and the CONSED package (version 7.0). All sequences represent coverage at least two times in both directions.

Sequence Analysis of CrtO

Two ORFs were identified in the genomic sequence of *Rhodococcus erythropolis* AN12 which shared homology to two different phytoene dehydrogenases. One ORF was designated CrtI and had the highest homology (45% identity, 56% similarity) to a putative phytoene dehydrogenase from *Streptomyces coelicolor* A3(2). The other ORF (originally designated as CrtI2, now as CrtO) had the highest homology (35% identity, 50% similarity; White O. et al *Science* 286 (5444), 1571–1577 (1999)) to a probable phytoene dehydrogenase DR0093 from *Deinococcus radiodurans*. Subsequent examination of the protein by motif analysis indicated that the crtO might function as a ketolase.

In Vitro Assay for Ketolase Activity of *Rhodococcus* CrtO

To confirm if crtO encoded a ketolase, the *Rhodococcus* crtO gene in *E. coli* was expressed was assayed for the presence of ketolase activity in vitro. The crtO gene was amplified from AN12 using the primers crtI2-N: ATGAGCGCATTTCTCGACGCC (SEQ ID NO:48) and crtI2-C: TCACGACCTGCTCGAACGAC (SEQ ID NO:49). The amplified 1599 bp full-length crtO gene was cloned into pTrcHis2-TOPO cloning vector (Invitrogen, Carlsbad, Calif.) and transformed into TOP10 cells following manufacture's instructions. The construct (designated pDCQ117) containing the crtO gene cloned in the forward orientation respective to the trc promoter on the vector was confirmed by restriction analysis and sequencing.

The in vitro enzyme assay was performed using crude cell extract from *E. coli* TOP10 (pDCQ117) cells expressing crtO. 100 ml of LB medium containing 100 µg/ml ampicillin was inoculated with 1 ml fresh overnight culture of TOP10 (pDCQ117) cells. Cells were grown at 37° C. with shaking at 300 rpm until OD$_{600}$ reached 0.6. Cells were then induced with 0.1 mM IPTG and continued growing for additional 3 hrs. Cell pellets harvested from 50 ml culture by centrifugation (4000 g, 15 min) were frozen and thawed once, and resuspended in 2 ml ice cold 50 mM Tris-HCl (pH7.5) containing 0.25% TritonX-100. 10 μg of β-carotene substrate (Spectrum Laboratory Products, Inc.) in 50 μl of acetone was added to the suspension and mixed by pipetting. The mixture was divided into two tubes and 250 mg of zirconia/silica beads (0.1 mm, BioSpec Products, Inc, Bartlesville, Okla.) was added to each tube. Cells were broken by bead beating for 2 min, and cell debris was removed by spinning at 10000 rpm for 2 min in an Eppendorf microcentrifuge 5414C. The combined supernatant (2 ml) was diluted with 3 ml of 50 mM Tris pH 7.5 buffer in a 50 ml flask, and the reaction mixture was incubated at 30° C. with shaking at 150 rpm for different lengths of time. The reaction was stopped by addition of 5 ml methanol and extraction with 5 ml diethyl ether. 500 mg of NaCl was added to separate the two phases for extraction. Carotenoids in the upper diethyl ether phase was collected and dried under nitrogen. The carotenoids were re-dissolved in 0.5 ml of methanol, for HLPC analysis, using a Beckman System Gold® HPLC with Beckman Gold Nouveau Software (Columbia, Md.). 0.1 ml of the crude acetone extraction was loaded onto a 125×4 mm RP8 (5 μm particles) column with corresponding guard column (Hewlett-Packard, San Fernando, Calif.). The flow rate was 1 ml/min and the Solvent program was 0–11.5 min 40% water/60% methanol, 11.5–20 min 100% methanol, 20–30 min 40% water/60% methanol. Spectral data was collected using a Beckman photodiode array detector (model 168).

Three peaks were identified at 470 nm in the 16 hr reaction mixture. When compared to standards, it was determined that the peak with a retention time of 15.8 min was β-carotene and the peak with retention time of 13.8 min was canthaxanthin. The peak at 14.8 min was most likely echinenone, the intermediate with only one ketone group addition. In the 2 hr reaction mixture, the echinenone intermediate was the only reaction product and no canthaxanthin was produced. Longer incubation times resulted in higher levels of echinenone and the appearance of a peak corresponding to canthaxanthin. Canthaxanthin is the final product in this step representing the addition of two ketone groups (Table 9). To confirm that the ketolase activity was specific for crtO gene, the assay was also performed with extracts of control cells that would not use β-carotene as the substrate. No product peaks were detected in the control reaction mixture.

In summary, the in vitro assay data confirmed that crtO encodes a ketolase, which converted β-carotene into canthaxanthin (two ketone groups) via echinenone (one ketone group) as the intermediate. This symmetric ketolase activity of *Rhodococcus* CrtO is different from what was reported for the asymmetric function of *Synechocystis* CrtO.

TABLE 9

HPLC Analysis Of The In Vitro Reaction Mixtures With Rhodococcus CrtO

|  | Canthaxanthin 474 nm 13.8 min | Echinenone 459 nm 14.8 min | β-carotene 449 nm 474 nm 15.8 min |
|---|---|---|---|
| 0 hr | 0% | 0% | 100% |
| 2 hr | 0% | 14% | 86% |
| 16 hr | 16% | 28% | 56% |
| 20 hr | 30% | 35% | 35% |

Example 8

All sequences from Examples 6 and 7 were identified by conducting BLAST (Basic Local Alignment Search Tool; Altschul, S. F., et al., (1993) *J. Mol. Biol.* 215:403–410; see also www.ncbi.nlm.nih.gov/BLAST/) searches for similarity to sequences contained in the BLAST "nr" database, according to the methodology of Example 2.

The results of these BLAST comparisons are given below in Table 10. The table displays data based on the BLASTXnr algorithm with values reported in expect values. The Expect value estimates the statistical significance of the match, specifying the number of matches, with a given score, that are expected in a search of a database of this size absolutely by chance.

TABLE 10

Identification of Carotenoid Genes Based on Sequence Homology

| Gene Name | Similarity Identified | SEQ ID | SEQ ID Peptide | % Identity[a] | % Similarity b | E-value[c] | Citation |
|---|---|---|---|---|---|---|---|
| crtE | Geranylgeranyl pryophosphate synthetase (or GGPP synthetase, or farnesyltranstransferase) EC 2.5.1.29 gi\|117509\|sp\|P21684\|CRTE_PAN AN GERANYLGERANYL PYROPHOSPHATE SYNTHETASE (GGPP SYNTHETASE) (FARNESYLTRANSTRANSFERA SE) | 25 | 26 | 83 | 88 | e-137 | Misawa et al., J. Bacteriol. 172 (12), 6704–6712 (1990) |

TABLE 10-continued

Identification of Carotenoid Genes Based on Sequence Homology

| Gene Name | Similarity Identified | SEQ ID | SEQ ID Peptide | % Identity[a] | % Similarity b | E-value[c] | Citation |
|---|---|---|---|---|---|---|---|
| crtX | Zeaxanthin glucosyl transferase EC 2.4.1.- gi\|1073294\|pir\|\|S52583 crtX protein - Erwinia herbicola | 27 | 28 | 75 | 79 | 0.0 | Lin et al., Mol. Gen. Genet. 245 (4), 417–423 (1994) |
| crtY | Lycopene cyclase gi\|1073295\|pir\|\|S52585 dycopene cyclase - Erwinia herbicola | 29 | 30 | 83 | 91 | 0.0 | Lin et al., Mol. Gen. Genet. 245 (4), 417–423 (1994) |
| crtI | Phytoene desaturaseEC 1.3.-.- gi\|1073299\|pir\|\|S52586 phytoene dehydrogenase (EC 1.3.-.-)- Erwinia herbicola | 31 | 32 | 89 | 91 | 0.0 | Lin et al., Mol. Gen. Genet. 245 (4), 417–423 (1994) |
| crtB | Phytoene synthaseEC2.5.1.- gi\|1073300\|pir\|\|S52587 prephytoene pyrophosphate synthase - Erwinia herbicola | 33 | 34 | 88 | 92 | e-150 | Lin et al., Mol. Gen. Genet. 245 (4), 417–423 (1994) |
| crtZ | -carotene hydroxylase gi\|117526\|sp\|P21688\|CRTZ_PAN AN -CAROTENE HYDROXYLASE | 35 | 36 | 88 | 91 | 3e-88 | Misawa et al., J. Bacteriol. 172 (12, 6704–6712 (1990) |
| crtO | sIr0088 - Synechocystis hypothetical protein | 37 | 38 | 35 | 64% | — | White O. et al Science 286 (5444), 1571–1577 (1999) Fernandez-Gonzalez, et al., J. Biol. Chem., 1997, 272:9728–9733 |

Example 9

Expression of β-carotene in *Methylomonas* 16A Growing on Methane

The crt gene cluster comprising the crtEXYIBZ genes from *Pantoea stewartii* (Example 6) was introduced into *Methylomonas* 16a to enable the synthesis of desirable 40-carbon carotenoids.

Primers were designed using the sequence from *Erwinia uredovora* to amplify a fragment by PCR containing the crt genes. These sequences included 5'-3':

```
ATGACGGTCTGCGCAAAAAAACACG          SEQ ID 43

GAGAAATTATGTTGTGGATTTGGAATGC        SEQ ID 44
```

Chromosomal DNA was purified from *Pantoea stewadtii* (ATCC no. 8199) and Pfu Turbo polymerase (Stratagene, La Jolla, Calif.) was used in a PCR amplifcation reaction under the following conditions: 94° C., 5 min; 94° C. (1 min)-60° C. (1 min)-72° C. (10 min) for 25 cycles, and 72° C. for 10 min. A single product of approximately 6.5 kb was observed following gel electrophoresis. Taq polymerase (Perkin Elmer) was used in a ten minute 72° C. reaction to add additional 3' adenoside nucleotides to the fragment for TOPO cloning into pCR4-TOPO (Invitrogen, Carlsbad, Calif.). Following transformation to *E. coli* DH5α (Life Technologies, Rockville, Md.) by electroproation, several colonies appeared to be bright yellow in color indicating that they were producing a carotenoid compound For introduction into *Methylomonas* 16a, the crt gene cluster from pCR4-crt was first subcloned into the unique EcoRI site within the chloramphenicol-resistance gene of the broad host range vector, pBHR1 (MoBiTec, LLC, Marco Island, Fla.). pBHR1 (500 ng) was linearized by digestion with EcoRI (New England Biolabs, Beverly, Mass.) and then dephosphorylated with calf intestinal alkaline phosphatase (Gibco/BRL, Rockville, Md.). pCR4-crt was digested with EcoRI and the 6.3 kb EcoRI fragment containing the crt gene cluster (crtEXYIB) was purified following gel electrophoresis in 0.8% agarose (TAE). This DNA fragment was ligated to EcoRI-digested pBHR1 and the ligated DNA was used to transform *E. coli* DH5α by electroporation. Transformants were selected on LB medium containing 50 ug/ml kanamycin.

Figure 3A:
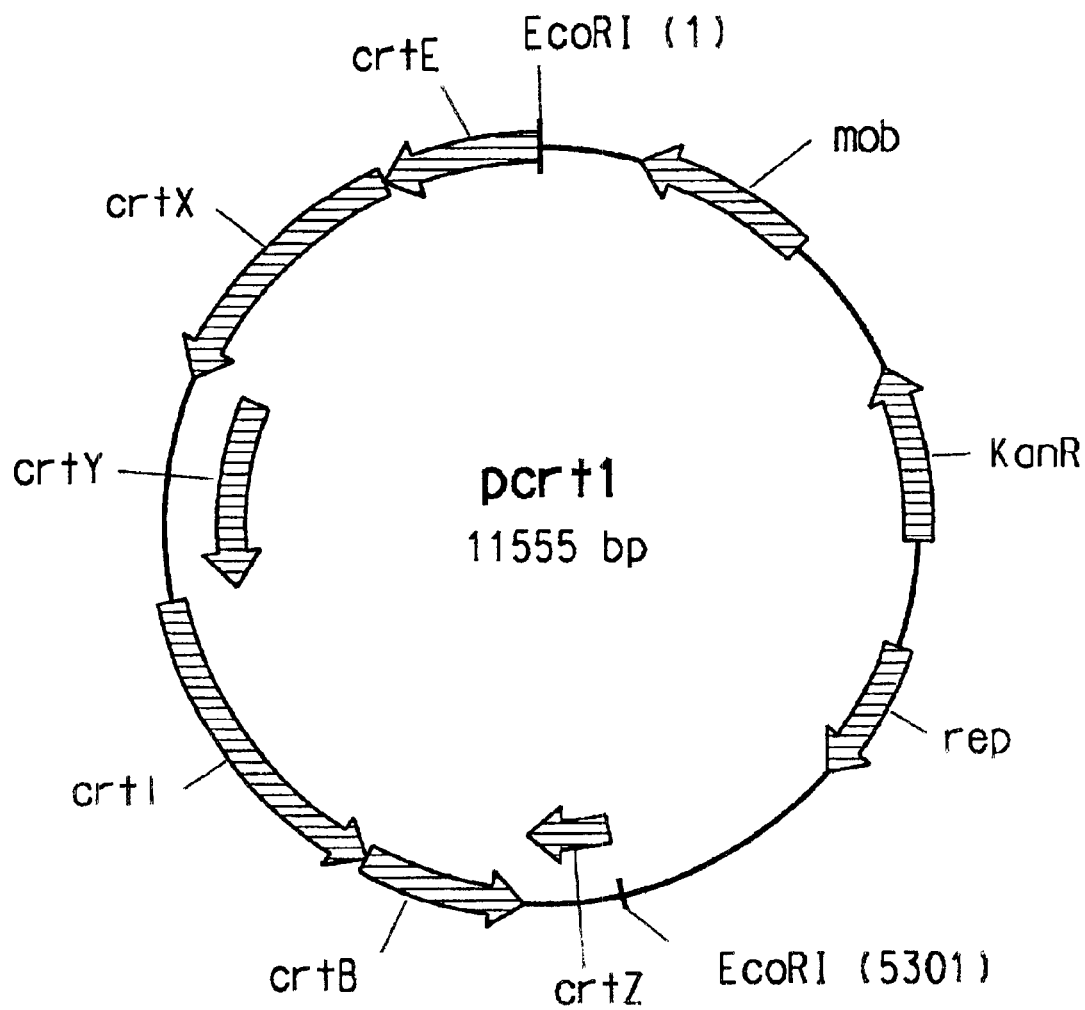
FIG. 3 shows plasmid pcrt1 and HPLC spectra verifying synthesis of β-carotene in those *Methylomonas* containing plasmid pcrt1.
Figure 3B:
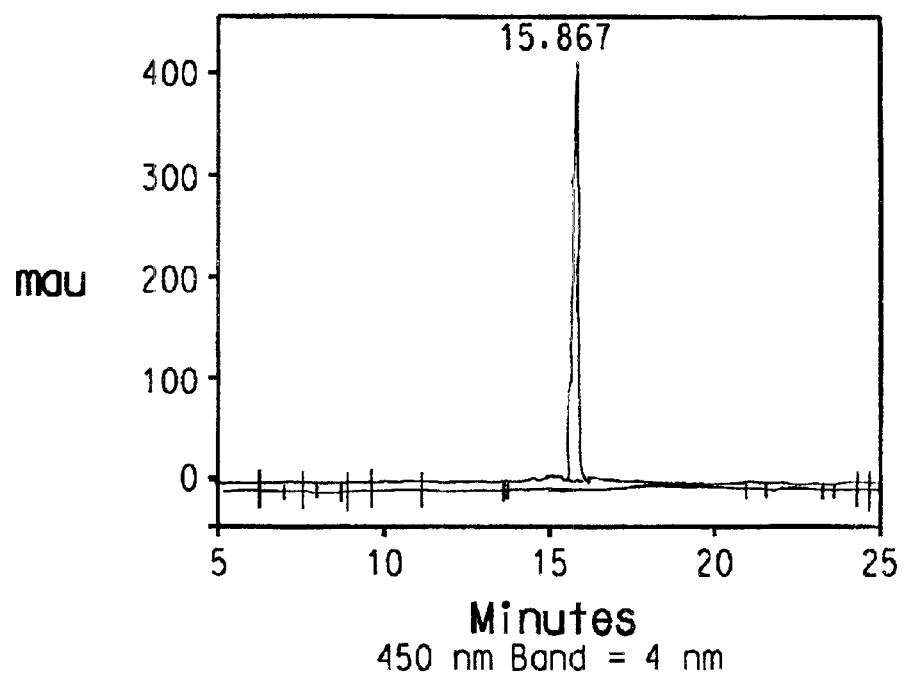
Figure 3C:
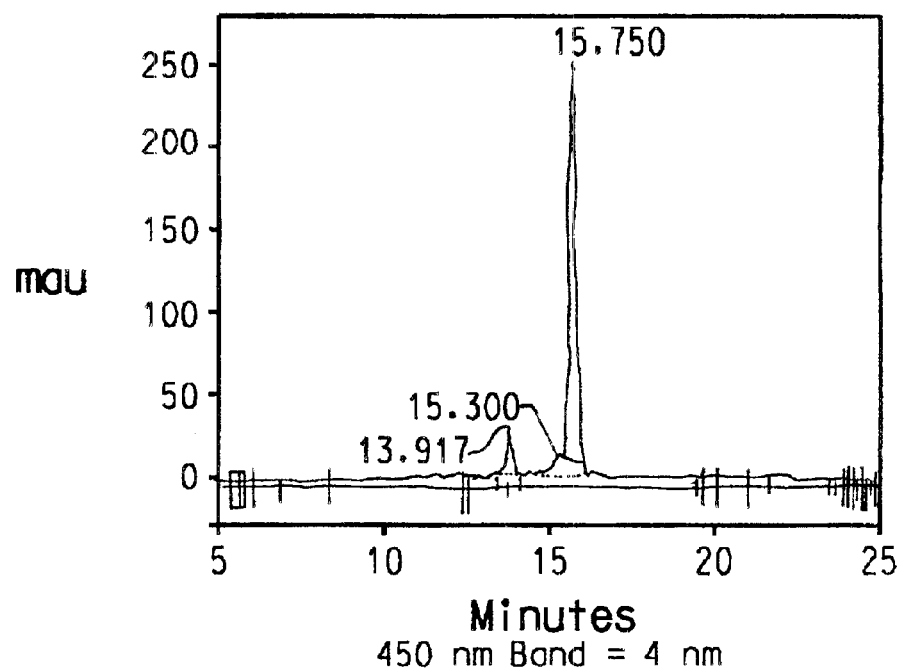

Several isolates were found to be sensitive to chloramphenicol (25 ug/ml) and demonstrated a yellow colony phenotype after overnight incubation at 37° C. Analysis of the plasmid DNA from these transformants confirmed the presence of the crt gene cluster cloned in the same orientation as the pBHR1 chloramphenicol-resistance gene and this plasmid was designated pCrt1 (FIG. 3). In contrast, analysis of the plasmid DNA from transformants demonstrating a white colony phenotype confirmed the presence of the crt gene cluster cloned in the opposite orientation as the pBHR1 chloramphenicol-resistance gene and this plasmid was designated pCrt2. These results suggested that functional expression of the crt gene cluster was directed from the pBHR1 cat promoter.

Plasmid pcrt1 was transferred into *Methylomonas* 16a by tri-parental conjugal mating. The *E. Coli* helper strain containing pRK2013 and the *E. coli* DH5α donor strain containing pCrt1 were grown overnight in LB medium containing kanamycin (50 μg/mL), washed three times in LB, and resuspended in a volume of LB representing approximately a 60-fold concentration of the original culture volume. The *Methylomonas* 16a recipient was grown for 48 hours in Nitrate liquid "BTZ-3" medium (General Methods) in an atmosphere containing 25% (v/v) methane, washed three times in BTZ-3, and resuspended in a volume of BTZ-3 representing a 150-fold concentration of the original culture volume. The donor, helper, and recipient cell pastes were combined on the surface of BTZ-3 agar plates containing 0.5% (w/v) yeast extract in ratios of 1:1:2 respectively.

Plates were maintained at 30° C. in 25% methane for 16–72 hours to allow conjugation to occur, after which the cell pastes were collected and resuspended in BTZ-3. Dilutions were plated on BTZ-3 agar containing kanamycin (50 μg/mL) and incubated at 30° C. in 25% methane for up to 1 week. Transconjugants were streaked onto BTZ-3 agar with kanamycin (50 μg/mL) for isolation. Analysis of plasmid DNA isolated from these transconjugants confirmed the presence of pCrt1 (FIG. 3).

For analysis of carotenoid composition, transconjugants were cultured in 25 ml BTZ-3 containing kanamycin (50 μg/mL) and incubated at 30° C. in 25% methane as the sole carbon source for up to 1 week. The cells were harvested by centrifugation and frozen at −20° C. After thawing, the pellets were extracted and carotenoid content was analyzed by HPLC according to the methodology of the General Methods.

HPLC analysis of extracts from *Methylomonas* 16a containing pCrt1 confirmed the synthesis of β-carotene. The left panel of FIG. 3 shows the HPLC results obtained using the β-carotene standard and a single peak is present at 15.867 min. Similarly, the right panel of FIG. 3 shows the HPLC profile obtained for analysis of *Methylomonas* 16a transconjugant cultures containing the pCrt1 plasmid. A similar peak at 15.750 min is indicative of β-carotene in the cultures.

Example 10

Expression of Zeaxanthin in *Methylomonas* 16A Growing on Methane

Figure 4A:
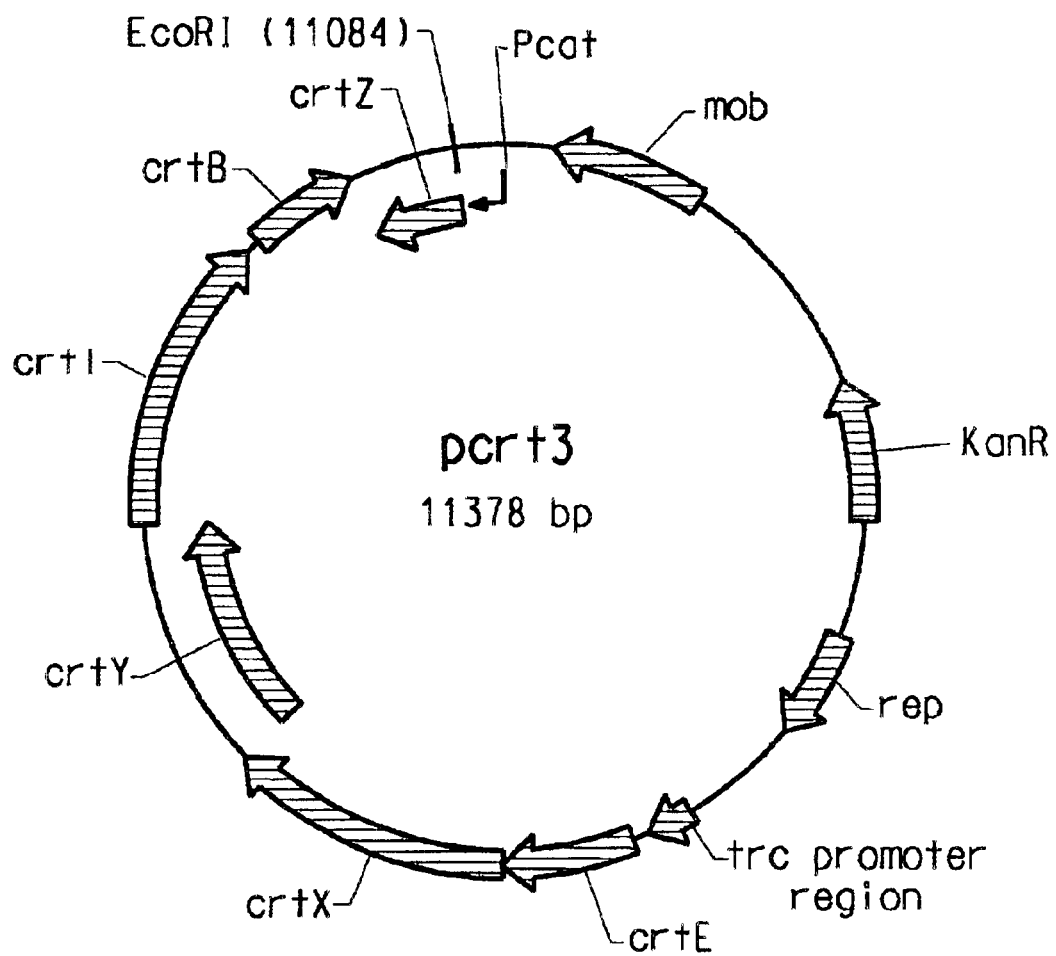
FIG. 4 shows plasmid pcrt3 and HPLC spectra verifying synthesis of zeaxanthin and its mono- and di-glucosides in those *Methylomonas* containing plasmid pcrt3.
Figure 4B:
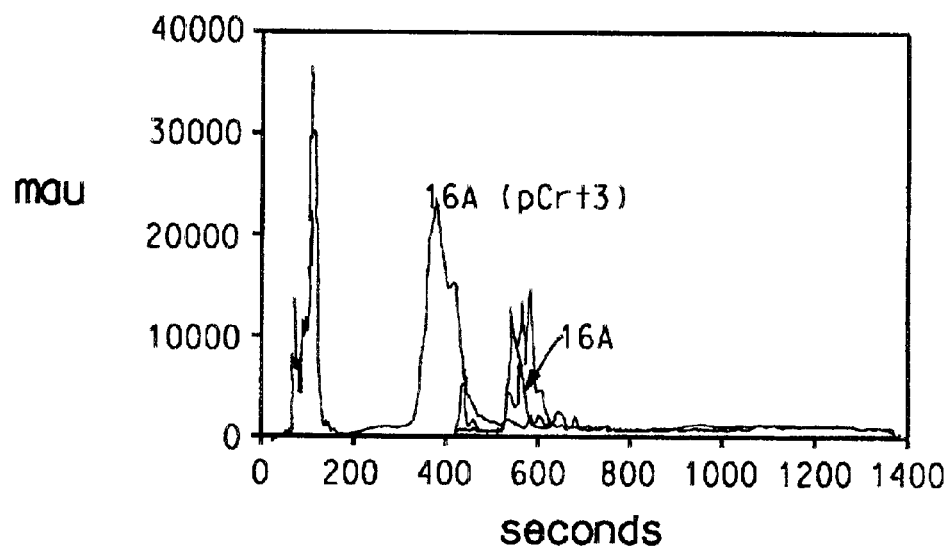
Figure 4C:
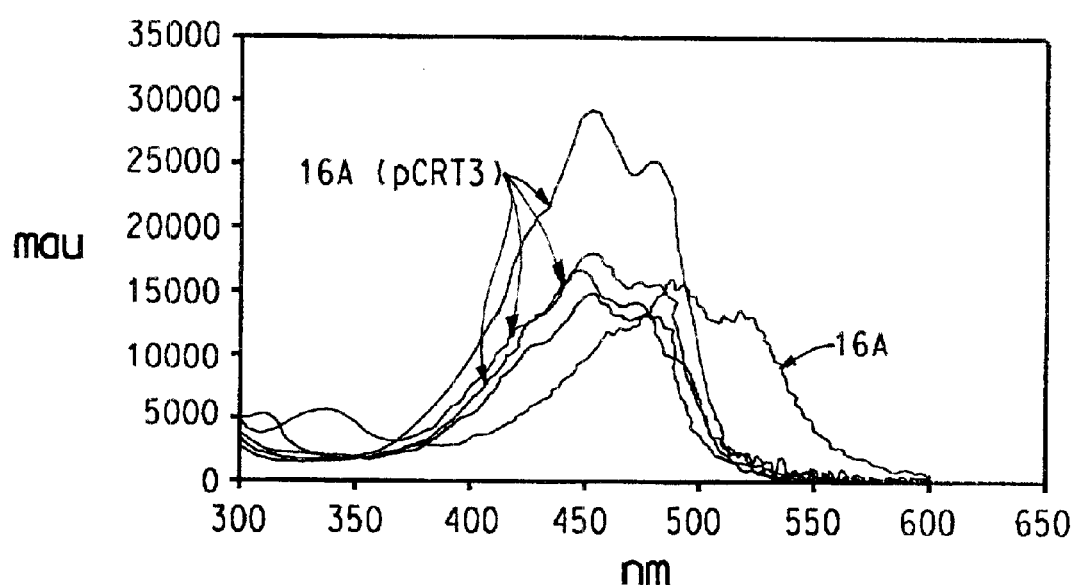

To enable the synthesis of zeaxanthin in *Methylomonas* 16a, the crt gene cluster from pTrcHis-crt2 (as described above) was subcloned into the chloramphenicol-resistance gene of the broad host range vector, pBHR1 (MoBiTec, LLC, Marco Island, Fla.). pBHR1 (500 ng) was digested sequentially with EcoRI and ScaI and the 4876 bp EcoRI-ScaI DNA fragment was purified following gel electrophoresis in 0.8% agarose (TAE). Plasmid pTrcHis-crt2 was digested simultaneously with SspI and EcoRI and the 6491 bp SspI-EcoRI DNA fragment containing the crt gene cluster (crtEXYIB) under the transcriptional control of the *E. coli* trc promoter was purified following gel electrophoresis in 0.8% agarose (TAE). The 6491 bp SspI-EcoRI fragment was ligated to the 4876 bp EcoRI-ScaI fragment and the ligated DNA was used to transform *E. coli* DH5α by electroporation. Transformants were selected on LB medium containing 50 ug/ml kanamycin. Several kanamycin-resistant isolates were also sensitive to chloramphenicol (25 ug/ml) and demonstrated yellow colony color after overnight incubation at 37° C. Analysis of the plasmid DNA from these transformants confirmed the presence of the crt gene cluster cloned into pBHR1 under the transcriptional control of the *E. coli* trc promoter and were designated as pCrt3. The plasmid map for this pCrt3 construct is shown in FIG. 4. The $P_{cat}$ promoter is illustrated with a small bold black arrow, in contrast to the large wide arrows, representing specific genes as labeled.

Plasmid pCrt3 was transferred into *Methylomonas* 16a by tri-parental conjugal mating, as described above for pCrt1 (Example 9). Transconjugants containing this plasmid demonstrated yellow colony color following growth on BTZ-3 agar with kanamycin (50 μg/mL) and methane as the sole carbon source.

HPLC analysis of extracts from *Methylomonas* 16A containing pCrt3 revealed the presence of zeaxanthin and its mono- and diglucosides. These results are shown in FIG. 4. The left panel shows the HPLC profile of extracts from *Methylomonas* 16A or *Methylomonas* 16A containing the pcrt3. The right panel shows the UV spectra of the individual peaks displayed in the HPLC profile and demonstrate the synthesis of zeaxanthin and its mono- and di-glucosides in *Methylomonas* 16A containing pcrt3. These results suggested that the crtEXYIB genes were functionally expressed from the trc promoter while the crtZ gene was transcribed in the opposite orientation from the pBHR1 cat promoter in *Methylomonas* 16A.

One skilled in the art would expect that deletion of crtX from this and subsequent plasmids should enable the production of zeaxanthin without formation of the mono- and di-glucosides. Furthermore, a plasmid in which the crtEY-IBZ genes are expressed in the same orientation from one or more promoters may be expected to alleviate potential transcriptional interference and enhance the synthesis of zeaxanthin. This would readily be possible using standard cloning techniques know to those skilled in the art.

Example 11

Expression of Zeaxanthin in *Methylomonas* 16A Growing on Methane, with an Optimized HMPS Promoter Analysis of gene array data following growth of *Methylomonas* 16a on methane suggested the hexoulose-monophosphate synthase (HMPS) to be one of the ten most highly expressed genes. Thus, one may use the DNA sequences comprising the HMPS promoter to direct high-level expression of heterologous genes, including those in the *P. stewartii* crt gene cluster, in *Methylomonas* 16A. Analysis of the 5'-DNA sequences upstream from the HMPS gene identified potential transcription initiation sites in both DNA strands using the NNPP/neural network prokaryotic promoter prediction program from Baylor College of Medicine Predictions concerning the forward strand of the H6P synthase are shown below in Table 11; similar results are shown below in Table 12 for the reverse strand.

TABLE 11

Promoter Predictions for H6P synthase-Forward Strand

| Start | End | Score | Promoter Sequence* |
|---|---|---|---|
| 63 | 108 | 0.93 | GAGAATTGGCTGAAAAACCAAATAAATAACAAAATTTAG (SEQ ID NO:50) CGAGTAAATGG |
| 119 | 164 | 0.91 | TTCAATTGACAGGGGGGCTCGTTCTGATTTAGAGTTGC (SEQ ID NO:51) TGCCAGCTTTTT |

TABLE 11-continued

Promoter Predictions for H6P synthase-Forward Strand

Start End Score Promoter Sequence*

| Start | End | Score | Promoter Sequence | |
|---|---|---|---|---|
| 211 | 256 | 0.85 | GGGTTGTCCAGATGTTGGTGAGCGGTCCTTATAACTAT<br>AACTGTAACAAT | (SEQ ID NO:52) |

*The transcription start sites are indicated in bold text.

TABLE 12

Promoter Predictions for H6P synthase-Reverse Strand

| Start | End | Score | Promoter Sequence | |
|---|---|---|---|---|
| 284 | 239 | 0.89 | TTAATGGTCTTGCCATGAGATGTGCTCCGATTGTTACAG<br>TTATAGTTATA | (SEQ ID NO:53) |
| 129 | 84 | 0.95 | CCCCCTGTCAATTGAAAGCCCGCCATTTACTCGCTAAAT<br>TTTGTTATTTA | (SEQ ID NO:54) |

*The transcription start sites are indicated in bold text.

Based on these sequences, the following primers were used in a polymerase chain reaction (PCR) to amplify a 240 bp DNA sequence comprising the HMPS promoter from *Methylomonas* 16a genomic DNA:

5' CCGAGTACTGAAGCGGGTTTTTGCAGGGAG 3' (SEQ ID NO:39)

5' GGGCTAGCTGCTCCGATTGTTACAG 3' (SEQ ID NO:40)

Figure 5A:
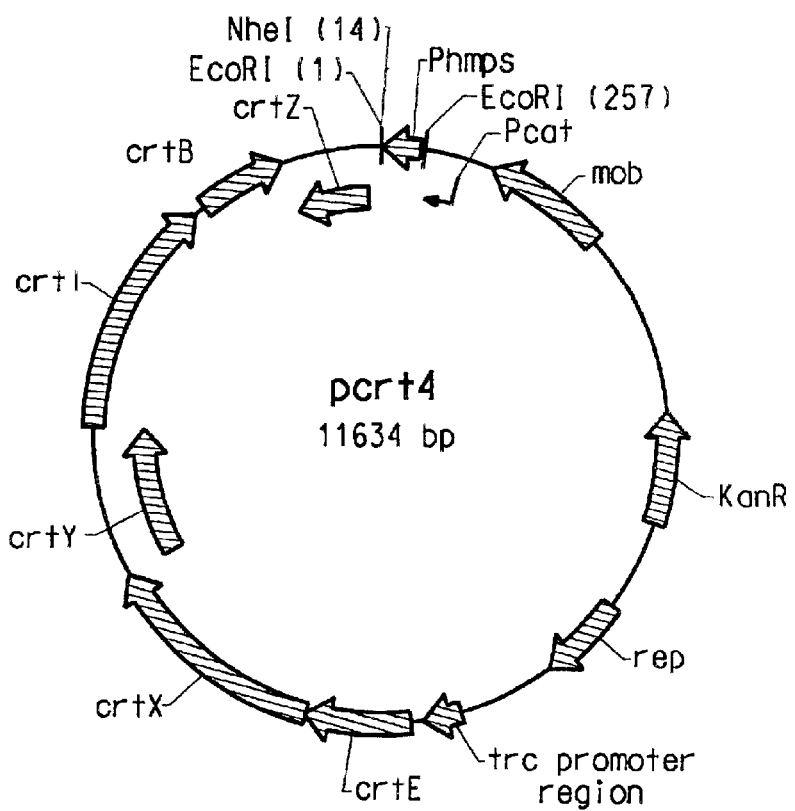
FIG. 5 shows plasmid pcrt4 and HPLC spectra verifying synthesis of zeaxanthin and its mono- and di-glucosides in those *Methylomonas* containing plasmid pcrt4.
Figure 5B:
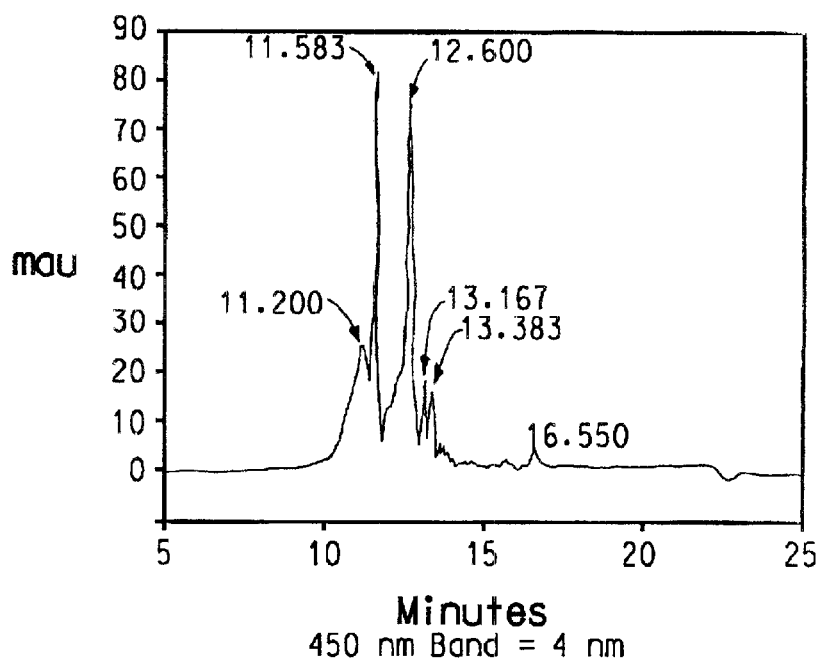

The PCR conditions were: 94° C. for 2 min, followed by 35 cycles of 94° C. for 1 min, 50° C. for 1 min and 72° C. for 2 min, and final extension at 72° C. for 5 min. After purification, the 240 bp PCR product was ligated to pCR2.1 (Invitrogen, Carlsbad, Calif.) and transformed into *E. coli* DH5α by electroporation. Analysis of the plasmid DNA from transformants that demonstrated white colony color on LB agar containing kanamycin (50 µg/ml) and X-gal identified the expected plasmid, which was designated pHMPS. PHMPS was digested with EcoRI and the 256 bp DNA fragment containing the HMPS promoter was purified following gel electrophoresis in 1.5% agarose (TEA). This DNA fragment was ligated to pCrt3 previously digested with EcoRI and dephosphorylated with calf intestinal alkaline phosphatase. The ligated DNA was used to transform *E. coli* DH5α by electroporation. Analysis of plasmid DNA from transformants that demonstrated yellow colony color on LB agar containing kanamycin (50 µg/ml) identified the expected plasmid, designated pCrt4, containing the crtEXYIB genes under the transcriptional control of the trc promoter and the crtZ gene under the transcriptional control of the hmps promoter (FIG. 5).

Plasmid pCrt4 was transferred into *Methylomonas* 16a by tri-parental conjugal mating. Transconjugants containing this plasmid demonstrated yellow colony color following growth on BTZ-3 agar with kanamycin (50 µg/mL) and methane as the sole carbon source. HPLC analysis of extracts from *Methylomonas* 16a containing pCrt4 revealed the presence of zeaxanthin, and its mono- and di-glucosides, thereby confirming expression of the crtZ gene. This data is shown in FIG. 5. Peaks with retention times of 13.38 min, 12.60 min and 11.58 min correspond to zeaxanthin, a mixture of zeaxanthin mono-glucosides and zeaxanthin diglucoside, respectively,

Example 12

Expression of Canthaxanthin and Astaxanthin in *Methylomonas* 16A Growing on Methane To enable the synthesis of canthaxanthin and astaxanthin in *Methylomonas* 16a, the *Rhodococcus erythropolis* AN 12 crtO gene encoding β-carotene ketolase (Example 7) was cloned into pcrt4. The crtO gene was amplified by PCR from pDCQ117 (Example 7) using the following primers to introduce convenient SpeI and NheI restriction sites as well as the ribosome binding site found upstream of crtE which was presumably recognized in *Methylomonas* 16a.

5'-AGCAGCTAGCGGAGGAATAAACCATGAGCGCATTTCTC-3' (SEQ ID NO:41)

5'-GACTAGTCACGACCTGCTCGAACGAC-3' (SEQ ID NO:42)

The PCR conditions were: 95° C. for 5 min, 35 cycles of 95° C. for 30 sec, 45–60° C. gradient with 0.15° C. decrease/cycle for 30 sec and 72° C. for 90 sec, and a final extension at 72° C. for 7 min. The 1653 bp PCR product was purified following gel electrophoresis in 1.0% agarose (TAE), digested simultaneously with SpeI and NheI restriction endonucleases and then ligated to pCrt4 previously digested with NheI and dephosphorylated with calf intestinal alkaline phosphatase. The ligated DNA was used to transform *E. coli* DH5α by electroporation.

Figure 6A:
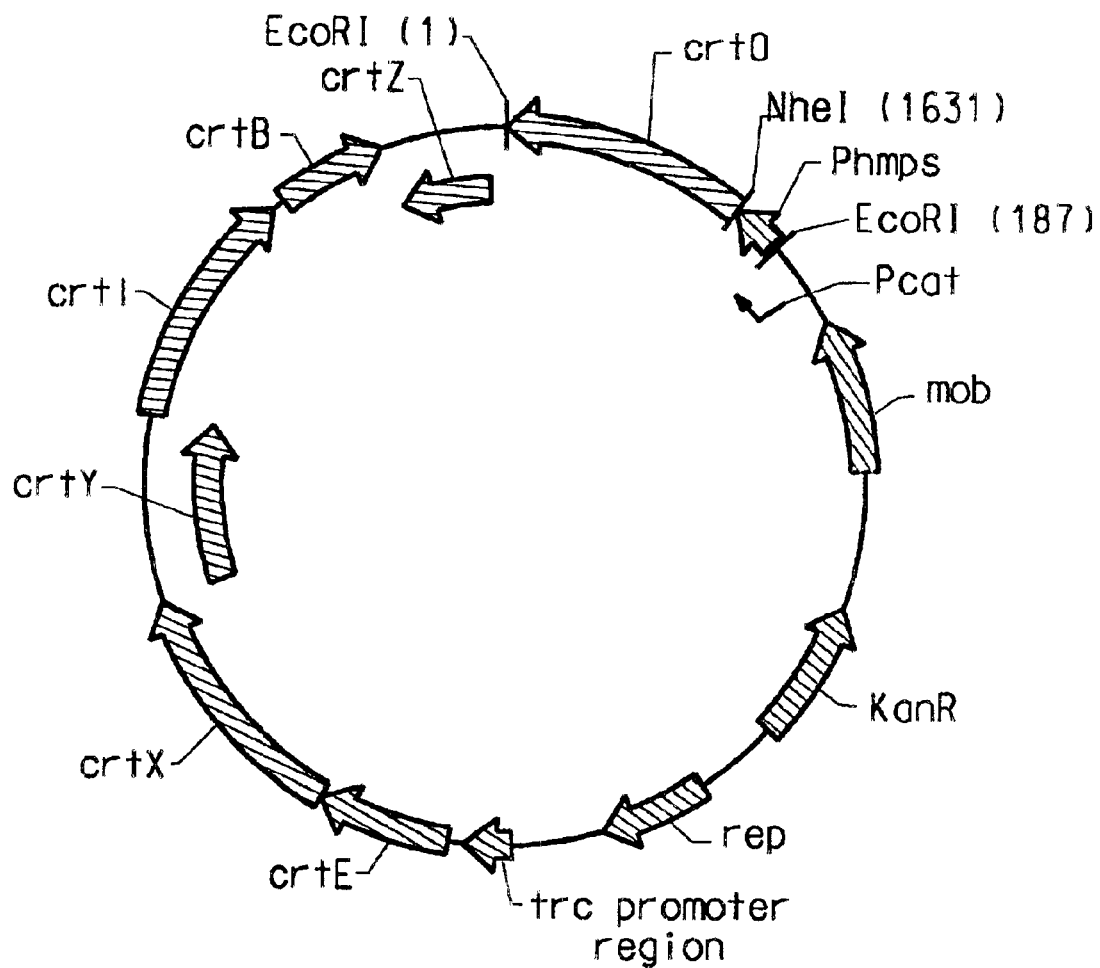
FIG. 6 shows plasmid pcrt4.1 and HPLC spectra verifying synthesis of canthaxanthin and astaxanthin in those *Methylomonas* containing plasmid pcrt4.1.
Figure 6B:
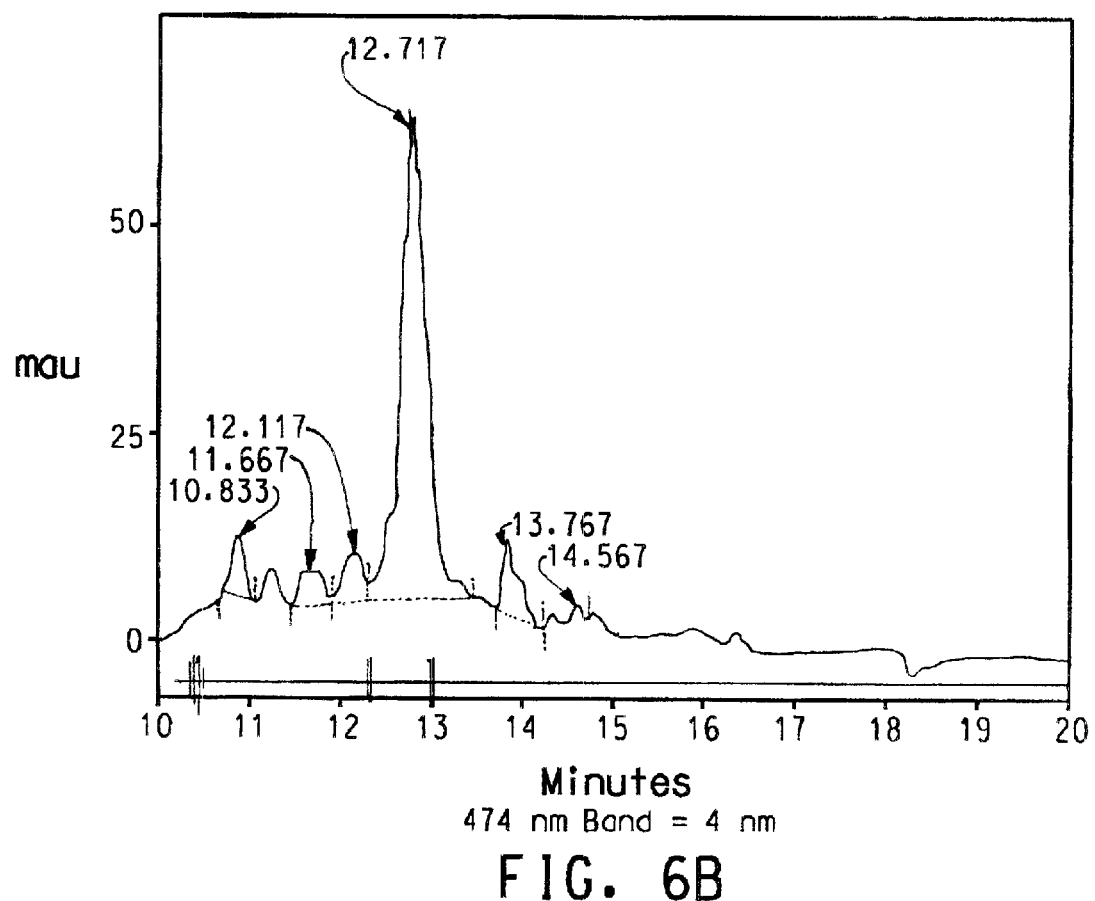
Figure 6C:
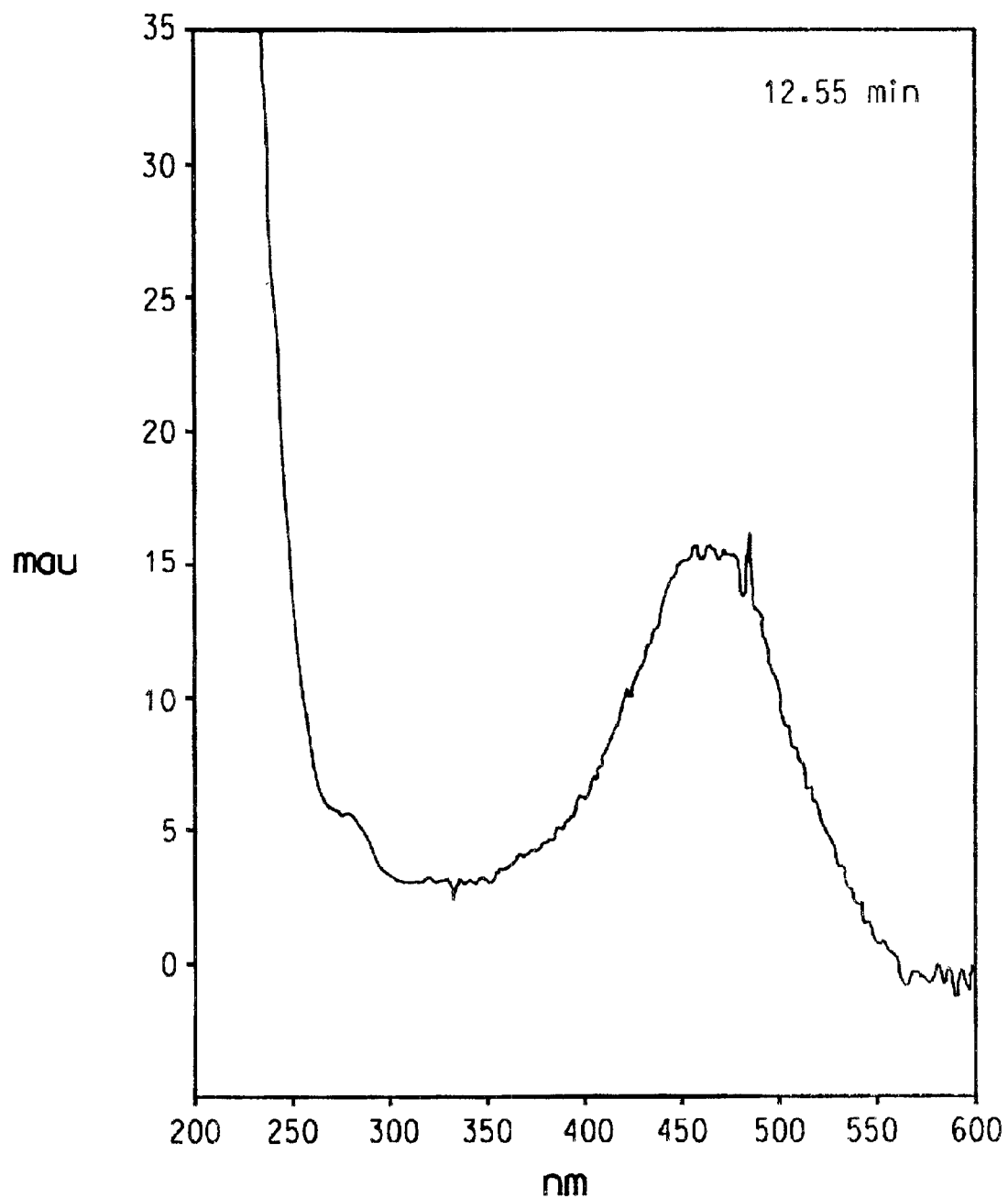

Analysis of plasmid DNA from transformants that demonstrated yellow colony color on LB agar containing kanamycin (50 ug/ml) identified the expected plasmid, designated pCrt4.1, in which the crtEXYIB genes were cloned under the transcriptional control of the trc promoter and the crtO and crtZ genes were cloned under the transcriptional control of the hmps promoter This plasmid construct is shown in FIG. 6. Upon prolonged incubation, transformants containing pcrt4.1 demonstrated a salmon pink colony color.

Plasmid pCrt4.1 was transferred into *Methylomonas* 16a by tri-parental conjugal mating. Transconjugants containing this plasmid demonstrated orange colony color following growth on BTZ-3 agar with kanamycin (50 µg/mL) and methane as the sole carbon source. HPLC analysis of extracts of *Methylomonas* 16a containing pCrt4.1 are shown in FIG. 6. These results revealed the presence of the endogenous *Methylomonas* 16a 30-carbon carotenoid (retention time of 12.717 min) as well as canthaxanthin (retention time of 13.767 min). The retention time of the wild-type pigment is very close to that expected for astaxanthin. Analysis of a shoulder on this peak confirmed the presence of astaxanthin The predominant formation of the wild-type 16A pigment in this strain suggested transcriptional interference of the crtEXYIB operon by high-level expression of the crtOZ operon from the strong hmps promoter. In addition, it is hypothesized that the cat promoter on the pBHR1 vector may be directing expression of crtOZ in concert with the hmps promoter. Plasmids in which the crtEYIBZO genes are expressed in the same orientation from one or more promoters may be expected to alleviate potential transcriptional interference and thereby enhance the synthesis of canthaxanthin and astaxanthin.

Example 13

Enhanced Synthesis of the Native Carotenoid of *Methylomonas* 16A by Amplification of Upper Isoprenoid Pathway Genes Native isoprene pathway genes dxs and dxr were amplified from the *Methylomonas* 16a genome by using PCR with the following primers.
Dxs Primers:
Forward reaction: aaggatccgcgtattcgtactc (contains a Bam HI site, SEQ ID NO:55).
Reverse reaction: ctggatccgatctagaaataggctcgagttgtcgttcagg (contains a Bam HI and a Xho I site, SEQ ID NO:56).
Dxr Primers:
Forward reaction: aaggatcctactcgagctgacatcagtgct (contains a Bam HI and a Xho I site, SEQ ID NO:57).
Reverse reaction: gctctagatgcaaccagaatcg (contains a Xba I site, SEQ ID NO:58).

The expected PCR products of dxs and dxr genes included sequences of 323 bp and 420 bp, respectively, upstream of the start codon of each gene in order to ensure that the natural promoters of the genes were present. The PCR program (in Perkin-Elmer, Norwalk, Conn.) was as follows: denaturing 95° C. (900 sec); 35 cycles of 94° C. (45 sec), 58° C. (45 sec), 72° C. (60 sec); final elongation 72° C. (600 sec). The reaction mixture (50 ul total volume) contained: 25 µl Hot Star master mix (Qiagen, Valencia, Calif.), 0.75 µl genomic DNA (approx. 0.1 ng), 1.2 µl sense primer (=10 pmol), 1.2 µl antisense primer (=10 pmol), 21.85 µl deionized water.

Standard procedures (Sambrook, J., Fritsch, E. F. and Maniatis, T. *Molecular Cloning: A Laboratory Manual*, Second Edition, Cold Spring Harbor Laboratory Press, Cold Spring Harbor (1989)), were used in order to clone dxs and dxr into pTJS75::lacZ:Tn5Kn, a low-copy, broad-host plasmid (Schmidhauser and Helinski *J. Bacteriology*. Vol. 164:446–455 (1985)).

For isolation, concentration, and purification of DNA, Qiagen kits (Valencia, Calif.) were used. Enzymes for the cloning were purchased from Gibco/BRL (Rockville, Md.) or NEB (Beverly, Mass.). To transfer plasmids into *E. coli*, One Shot Top10 competent cells (Invitrogen, Carlsbad, Calif.), cuvettes (0.2 cm; Invitrogen), and Bio-Rad Gene Pulser III (Hercules, Calif.) with standard settings were used for electroporation.

Figure 7A:
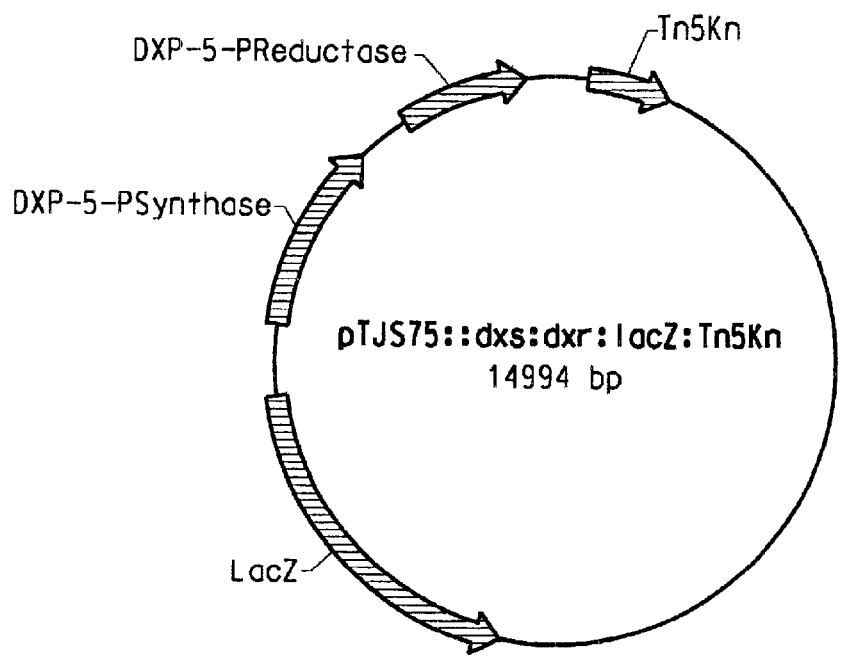
FIG. 7 shows plasmid pTJS75::dxs:dxr:lacZ:Tn5Kn and production of the native carotenoid in those *Methylomonas* containing plasmid pTJS75::dxs:dxr:lacZ:Tn5Kn. Additionally, the construct pcrt4.1 is shown.
Figure 7B:
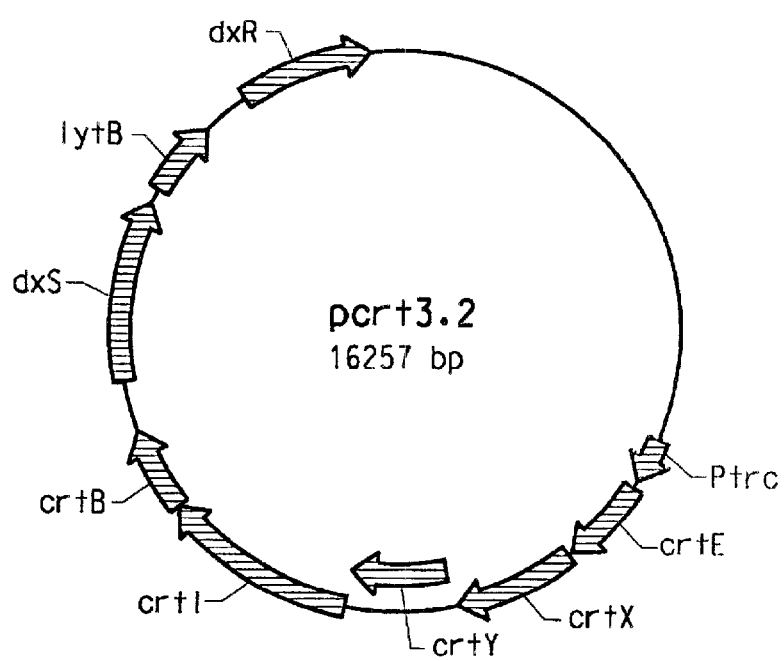
Figure 7C:
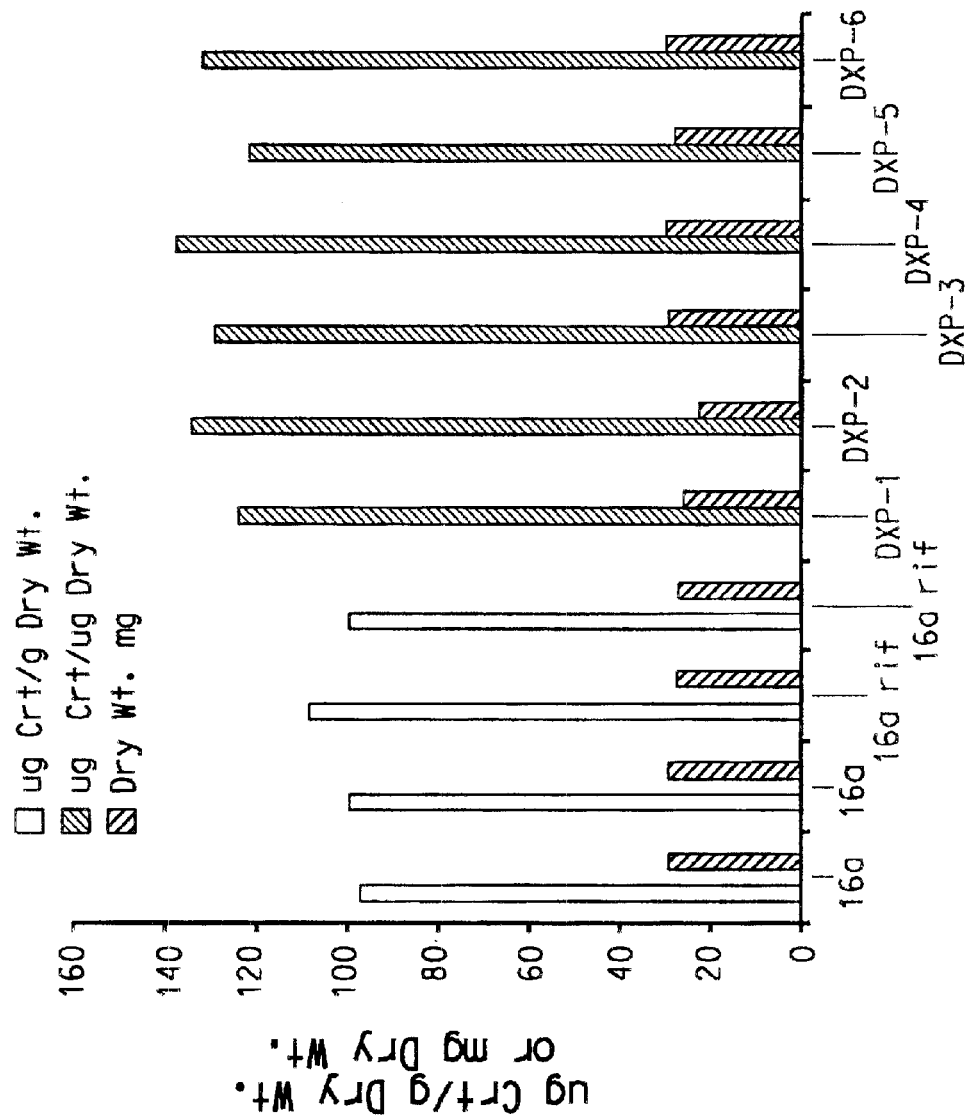

First, dxs was cloned into the Bam HI site, which was located between the lacZ gene and the Tn5Kn cassette of pTJS75::lacZ:Tn5Kn. The resulting plasmids were isolated from *E. coli* transformants growing on LB+ kanamycin (Kn, 50 µg/mL). The plasmid containing the insert in direction of the Kn-resistance gene (as confirmed by restriction analysis) was chosen for further cloning. The dxr gene was cloned in between dxs and the Tn5Kn cassette by using the Xho I and Xba I sites. The anticipated plasmid was isolated from *E. coli* transformants. The presence of dxs and dxr in the plasmid was confirmed by restriction analysis and sequencing. The resulting plasmid, pTJS75::dxs:dxr:lacZ:Tn5Kn is shown in FIG. 7.

The plasmid pTJS75::dxs:dxr:lacZ:Tn5Kn was transferred from *E. coli* into *Methylomonas* 16a by triparental conjugation. A spontaneous rifampin (Rif)-resistant isolate of strain *Methylomonas* 16a was used as the recipient to speed the isolation of the methanotroph from contaminating *E. coli* following the mating. Six separately isolated kanamycin-resistant *Methylomonas* 16a transconjugants were used for carotenoid content determination.

For carotenoid determination, six 100 mL cultures of transconjugants (in BTZ+50 µg/mL Kn) were grown under methane (25%) over the weekend to stationary growth phase. Two cultures of each, the wild-type strain and its Rif-resistant derivative without the plasmid, served as a control to see whether there are different carotenoid contents in those strains and to get a standard deviation of the carotenoid determination. Cells were spun down, washed with distilled water, and freeze-dried (lyophilizer: Virtis, Gardiner, N.Y.) for 24 h in order to determine dry-weights. After the dry-weight of each culture, was determined, cells were extracted. First, cells were welled with 0.4 mL of water and let stand for 15 min. After 15 min, four mL of acetone was added and thoroughly vortexed to homogenize the sample. The samples were then shaken at 30° C. for 1 hr. After 1 hr, the cells were centrifuged. Pink coloration was observed in the supernatant. The supernatant was collected and pellets were extracted again with 0.3 mL of water and 3 mL of acetone. The supernatants from the second extraction were lighter pink in color. The supernatants of both extractions were combined, their volumes were measured, and analyzed spectrophotometrically. No qualitative differences were seen in the spectra between negative control and transconjugant samples. In acetone extract, a following observation was typical measured by spectrophotometer (shoulder at 460 nm, maxima at 491 and 522 nm) (Amersham Pharmacia Biotech, Piscataway, N.J.). For calculation of the carotenoid content, the absorption at 491 nm was read, the molar extinction coefficient of bacterioruberin (188,000) and a MW of 552 were used. The MW of the carotenoid (552 g/mol) was determined by MALDI-MS of a purified sample (Silica/Mg adsorption followed by Silica column chromatography, reference: Britton, G., Liaaen-Jensen, S., Pfander, H., Carotenoids Vol. 1a; Isolation and analysis, Birkhäuser Verlag, Basel, Boston, Berlin (1995)).

A crude acetone extract from *Methylomonas* 16a cells has a typical absorption spectrum (inflexion at 460 nm, maxima at 491 nm and 522 nm). HPLC analysis (as described in the General Methods, except solvent program: 0–10 min 15% water/85% methanol, then 100% methanol) of acetone extracts confirmed that one major carotenoid (net retention volume at about 6 mL) with the above mentioned absorption spectrum is responsible for the pink coloration of wild-type and transconjugant *Methylomonas* 16a cells. Because nothing else in the extract absorbs at 491 nm, carotenoid content was directly measured in the acetone extract with a spectrophotometer (Amersham Pharmacia Biotech, Piscataway, N.J.).

The molar extinction coefficient of bacterioruberin (188,000), was used for the calculation of the quantity.

The following formula was used (Lambert-Beer's law) to determine the quantity of carotenoid:

$$Ca = A_{491nm}/(d \times \epsilon \times v \times MW)$$

Ca: Carotenoid amount (g)
$A_{491nm}$: Absorption of acetone extract at 491 nm (-)
d: Light path in cuvette (1 cm)
$\epsilon$: Molar extinction coefficient (L/(mol×cm))
MW: Molecular weight (g/mol)
v: Volume of extract (L)

To get the carotenoid content, the calculated carotenoid amount has to be divided by the corresponding cell dry weight.

TABLE 13

Native Carotenoid contents in Methylomonas 16a cells

| Cultures | dry weight (mg) | carotenoid (g) | carotenoid content (μg/g) |
|---|---|---|---|
| 16a-1[a] | 30.8 | 3.00194E-06 | 97.5 |
| 16a-2[a] | 30.8 | 3.0865E-06 | 100.2 |
| 16a Rif-1[b] | 29.2 | 3.12937E-06 | 107.2 |
| 16a Rif-2[b] | 30.1 | 3.02014E-06 | 100.3 |
| dxp 1[c] | 28.2 | 3.48817E-06 | 123.7 |
| dxp 2[c] | 23.8 | 3.17224E-06 | 133.3 |
| dxp 3[c] | 31.6 | 4.01962E-06 | 127.2 |
| dxp 4[c] | 31.8 | 4.38899E-06 | 138.0 |
| dxp 5[c] | 28.4 | 3.4547E-06 | 121.6 |
| dxp 6[c] | 30.3 | 4.00817E-06 | 132.3 |

[a]Methylomonas 16a native strain
[b]Rif resistant derivative of Methylomonas 16a without plasmid
[c]transconjugants containing pTJS75::dxs:dxr:lacZ:Tn5Kn plasmid There were no significant differences between four negative controls. Likewise, there were no significant differences between six transconjugants. However, approximately 28% increase in average carotenoid production was observed in the transconjugants in comparison to the average carotenoid production in negative controls (Table 13; FIG. 7

In order to confirm the structure, *Methylobacterium rhodinum* (formerly *Pseudomonas rhodos*: ATCC No. 14821) of which C30-carotenoid was identified was used as a reference strain (Kleinig et al., Z. Naturforsch 34c, 181–185 (1979); Kleinig and Schmitt, Z. Naturforsch 37c, 758–760 (1982)). A saponified extract of *Methylobacterium rhodinum* and of *Methylomonas* 16a were compared by HPLC analysis under the same conditions as mentioned above. The results are shown as follows:

Saponified *M. rhodinum*: inflexion at 460 nm, maxima at 487 nm, 517 nm.
Net retention volume=1.9 mL.
Saponified *Methylomonas* 16a: inflexion at 460 nm, maxima at 488 nm, 518 nm.
Net retention volume=2.0 mL.

Example 14

Enhanced Synthesis of Genetically Engineered Carotenoids in *Methylomonas* 16A by Amplification of Upper Isoprenoid Pathway Genes The previous example (Example 13) demonstrated that amplification of the dxs and dxr genes in *Methylomonas* 16a increased the endogenous 30-carbon carotenoid content by about 30%. Amplification of dxs, dxr and other isoprenoid pathway genes, such as lytB, may be used to increase the metabolic flux into an engineered carotenoid pathway and thereby enhance production of 40-carbon carotenoids, such as β-carotene, zeaxanthin, canthaxanthin and astaxanthin. The lytB gene was amplified by PCR from *Methylomonas* 16a using the following primers that also introduced convenient XhoI restriction sites for subcloning:

5'-TGGCTCGAGAGTAAAACACTCAAG-3'    (SEQ ID NO:59)

5'-TAGCTCGAGTCACGCTTGC-3'         (SEQ ID NO:60)

The PCR conditions were: 95° C. for 5 min, 35 cycles of 95° C. for 30 sec, 47–62° C. gradient with 0.25° C. decrease/cycle for 30 sec and 72° C. for 1 min, and a final extension at 72° C. for 7 min.

Following purification, the 993 bp PCR product was digested with XhoI and ligated to pTJS75::dxs:dxr:lacZ:Tn5Kn, previously digested with XhoI and dephosphorylated with calf intestinal alkaline phosphatase. The ligated DNA was used to transform *E. coli* DH10B by electroporation. Analysis of the plasmid DNA from transformants selected on LB agar containing kanamycin (50 ug/ml) identified a plasmid in which the lytB gene was subcloned between the dxs and dxr genes in an operon under the control of the native dxs promoter. This operon was excised as a 4891 bp DNA fragment following sequential digestion with HindIII and BamHI restriction endonucleases, made blunt-ended by treatment with T4 DNA polymerase and purified following gel electrophoresis in 1.0% agarose (TAE). The purified DNA fragment was ligated to crt3 (Example 10) previously linearized within the crtZ gene by digestion with BstXI, made blunt-ended by treatment with T4 DNA polymerase and dephosphorylated with calf intestinal alkaline phosphatase. The ligated DNA was used to transform *E. coli* DH10B by electroporation and transformants were selected on LB agar containing kanamycin (50 ug/ml). Analysis of the plasmid DNA from transformants which demonstrated more intense yellow colony color than those containing crt3 identified a plasmid, designated pcrt3.2, containing both the crtEXYIB and dxs-lytB-dxr operons (FIG. 7).

HPLC analysis of extracts from *E. coli* containing pcrt3.2 confirmed the synthesis of β-carotene. Transfer of this plasmid into *Methylomonas* 16a by tri-parental conjugal mating will enhance production of β-carotene compared to transconjugants containing pcrt3.

Example 15

Industrial Production of β-Carotene in *Methylomonas* 16a Optical Density Measurements Growth of the *Methylomonas* culture was monitored at 600 nm using a Shimadzu 160U UV/Vis dual beam, recording spectrophotometer. Water was used as the blank in the reference cell. Culture samples were appropriately diluted with de-ionized water to maintain the absorbance values less than 1.0.

Dry Cell Weight Determination 20 mL of *Methylomonas* cell culture was filtered through a pre-weighed 0.2 μm filter (Type GTTP, Millipore, Bedford, Mass.) by vacuum filtration. Following filtration of biomass samples, filters were washed with 10 mL of de-ionized water and filtered under vacuum to dryness. Filters were then placed in a drying oven at 95° C. for 24 to 48 hr. After 24 hr; filters were cooled to room temperature and re-weighed. After recording the filter weight, the filters were returned to the drying oven and the process repeated at various time intervals until no further change in weight loss was recorded. Media contribution to the dry cell weight (DCW) measurement was obtained by filtering 20 mL of fermentation media prior to inoculation by the above procedure. Dry cell weight is calculated by the following formula:

$$DCW[=] \ [g \ mL^{-1}] = \frac{[(\text{weight of filter} + \text{cells}) - (\text{weight of filter})] - [(\text{weight of filter} + \text{media}) - (\text{weight of filter})]}{20 \ mL \ \text{culture volume}}$$

Ammonia Concentration Determination 3 mL culture samples for ammonia analyses were taken from the fermenter and centrifuged at 10,000×g and 4° C. for 10 min. The supernatant was then filtered through a 0.2 μm syringe filter (Gelman Lab., Ann Arbor, Mich.) and placed at −20° C. until analyzed. Ammonia concentration in the fermentation broth was determined by ion chromatography using a Dionex System 500 Ion Chromatograph (Dionex, Sunnyvale, Calif.) equipped with a GP40 Gradient Pump, AS3500 Autosampler, and ED40 Electrochemical Detector operating in conductivity mode with an SRS current of 100 mA. Separation of ammonia was accomplished using a Dionex CS12A column fitted with a Dionex CG12A Guard column. The columns and the chemical detection cell were maintained at 35° C. Isocratic elution conditions were employed using 22 mM $H_2SO_4$ as the mobile phase at a flowrate of 1 mL $min^{-1}$. The presence of ammonia in the fermentation broth was verified by retention time comparison with an $NH_4Cl$ standard. The concentration of ammonia in the fermentation broth was determined by comparison of area counts with a previously determined $NH_4Cl$ standard calibration curve. When necessary, samples were diluted with de-ionized water so as to be within the bounds of the calibration curve.

Carbon Dioxide Evolution Rate (CER) Determination

The carbon dioxide concentration in the exit gas stream from the fermenter was determined by gas chromatography (GC) using a Hewlett Packard 5890 Gas Chromatograph (Hewlett Packard, Avondale, Pa.) equipped with a TCD detector and HP19091 P-Q04, 32 m×32 μm×20 μm divinylbenzene/styrene porous polymer capillary column. Gas samples were withdrawn from the outlet gas stream through a sample port consisting of a polypropylene "T" to which the side arm was covered with a butyl rubber stopper. 200 μL samples were collected by piercing the rubber stopper with a Hamilton (Reno, Nev.) gas-tight GC syringe. Samples were collected after purging the barrel of the syringe a minimum of 4 times with the outlet gas. Immediately following sample collection, the volume in the syringe was adjusted to 100 μL and injected through a splitless injection port onto the column. Chromatographic conditions used for $CO_2$ determination were as follows: Injector Temperature (100 C.); Oven Temperature (35 C); Detector Temperature (140 C); Carrier Gas (Helium); Elution Profile (Isothermal); Column Head Pressure (15 psig). The presence of $CO_2$ in the exit gas stream was verified by retention time comparison with a pure component $CO_2$ standard. The concentration of $CO_2$ in the exit gas stream was determined by comparison of area counts with a previously determined $CO_2$ standard calibration curve. Standard gas cylinders (Robert's Oxygen, Kenneft Square, Pa.) containing $CO_2$ in the concentration range of 0.1% (v/v) to 10% (v/v) were used to generate the calibration curve.

The carbon dioxide evolution rate was calculated from the following formula:

$$CER[=] \ mmol \ hr^{-1} = \frac{\text{Exit Pressure} * CO_2 \ \text{concentration} * \text{inlet gas flowrate}}{R * \text{Absolute temperature of the exit gas stream}}$$

In the above equation the exit pressure from the fermenter was assumed to be equal to the atmospheric pressure. The inlet gas flowrate was calculated from the sum of the individual methane and air flowrates. R is the ideal gas constant=82.06 $cm^3$ atm $mol^{-1}$ $K^{-1}$. The absolute temperature of the exit gas stream was calculated by the following formula: T(K)=t(° C.)+273.15, where T is the absolute temperature in K, and t is the exit gas temperature in ° C. and was assumed to be equal to the ambient temperature.

β-Carotene Extraction and Determination by High Performance Liquid Chromatography (HPLC)

15–30 mL of the *Methylomonas* culture was centrifuged at 10,000×g and 4° C. for 10 min. The supernatant was decanted and the cell pellet frozen at −20° C. The frozen cell pellet was thawed at room temperature to which 2.5 mL of acetone was added. The sample was vortexed for 1 min and allowed to stand at room temperature for an additional 30 min before being centrifuged at 10,000×g and 4° C. for 10 min. The acetone layer was decanted and saved. The pellet was then re-extracted with an additional 2.5 mL of acetone, centrifuged, and the two acetone pools combined. Visual observation of the cell pellet revealed that all the β-carotene had been removed from the cells following the second extraction. The acetone pool was then concentrated to 1 mL under a stream of $N_2$, filtered through a 0.45 μm filter, and analyzed by HPLC.

Acetone samples containing β-carotene were analyzed using a Beckman System Gold HPLC (Beckman Coulter, Fullerton, Calif.) equipped with a model 125 ternary pump system, model 168 diode array detector, and model 508 autosampler. 100 μL of concentrated acetone extracts were injected onto a HP LichroCART 125-4, $C_8$ reversed phase HPLC column (Hewlett Packard, Avondale, Pa.). Peaks were integrated using Beckman Gold software. Retention time and spectral comparison confirmed peak identity with β-carotene pure component standards in the wavelength range from 220 to 600 nm. The retention time and spectral profiles of the β-carotene in the acetone extracts were an exact match to those obtained from the pure component β-carotene standards. The β-carotene concentrations in the acetone extracts were quantified by comparison of area counts with a previously determined calibration curve as described below. A wavelength of 450 nm, corresponding to the maximum absorbance wavelength of β-carotene in acetone, was used for quantitation.

A mobile consisting of methanol and water was used for reversed phase separation of β-carotene. The separation of β-carotene was accomplished using a linear gradient of 60% methanol and 40% water changing linearly over 11.5 minutes to 100% methanol. Under the chromatographic conditions employed, resolution of α-carotene from β-carotene could not be attained.

β-carotene calibration curves were prepared from stock solutions by dissolving 25 mg of β-carotene (96% purity, Spectrum Chemical Inc., New Brunswick, N.J.) in 100 mL of acetone. Appropriate dilutions of this stock solution were made to span the β-carotene concentrations encountered in the acetone extracts. Calibration curves constructed in this manner were linear over the concentration range examined.

Fermentation of *Methylomonas* 16a

Fermentation was performed as a fed-batch fermentation under nitrogen limitation using a 3 liter, vertical, stirred tank fermenter (B. Braun Biotech Inc., Allentown, Pa.) with a working volume of 2 liters. The fermenter was equipped with 2 six-bladed Rushton turbines and stainless steel headplate with fittings for pH, temperature, and dissolved oxygen probes, inlets for pH regulating agents, sampling tube for withdrawing liquid samples, and condenser. The exit gas line from the fermenter contained a separate port for sampling the exit gas stream for GC analysis of methane, $O_2$, and $CO_2$ concentrations. The fermenter was jacketed for temperature control with the temperature maintained constant at 30° C. through the use of an external heat exchanger. Agitation was maintained in the range of 870–885 rpm. The pH of the fermentation was maintained constant at 6.95 through the use of 2.5 M NaOH and 2 M $H_2SO_4$.

Methane was used as the sole carbon and energy source during the fermentation. The flow of methane to the fermenter was metered using a Brooks (Brooks Instrument, Hatfield, Pa.) mass flow controller. A separate mass flow controller was used to regulate the flow of air. Prior to entering the fermenter, the individual methane and air flows were mixed and filtered through a 0.2 μm in-line filter (Millipore, Bedford, Mass.) giving a total gas flowrate of 260 mL min$^{-1}$ (0.13 v/v/min) and methane concentration of 23% (v/v) in the inlet gas stream. The gas was delivered to the medium 3 cm below the lower Rushton turbine through a perforated pipe. 2 liters of a minimal salts medium of the composition given in Table 14 was used for the fermentation. Silicone antifoam (Sigma Chemical Co., St. Louis, Mo.) was added to a final concentration of 800 ppm prior to sterilization to suppress foaming. Before inoculating, the fermenter and it contents were sterilized by autoclaving for 1 hr at 121° C. and 15 psia. Once the medium had cooled, 4 mL of a 25 mg mL$^{-1}$ kanamycin stock solution was added to the fermentation medium to maintain plasmid selection pressure during the fermentation.

TABLE 14

Fermentation Media Composition

| Component | Amount (g L$^{-1}$) |
| --- | --- |
| NH$_4$Cl | 1.07 |
| KH$_2$PO$_4$ | 1 |
| MgCl$_2$*6H$_2$O | 0.4 |
| CaCl$_2$*2H$_2$O | 0.2 |
| 1M HEPES Solution (pH 7) | 50 mL L$^{-1}$ |
| Solution 1* | 30 mL L$^{-1}$ |
| Na$_2$SO$_4$ | 1 |

*Note: The compositon of Solution 1 is provided in the General Methods.

1 ml of frozen *Methylomonas* 16a containing plasmid pCRT1 was used to inoculate a 100 mL culture of sterile 0.5× minimal salts media containing 50 μg mL$^{-1}$ of kanamycin in a 500 mL Wheaton bottle sealed with a butyl rubber stopper and aluminum crimp cap. Methane was added to the culture by piercing the rubber stopper with a 60 mL syringe fitted with a 21 gauge needle to give a final methane concentration in the headspace of 25% (v/v). The inoculated medium was shaken for approximately 48 hr at 30° C. in a controlled environmental rotary shaker. When cell growth reached saturation, 5 mL of this culture was used to inoculate 2 100-mL cultures as described above. When the optical density of the cultures reached 0.8, 60 mL of each culture was used to inoculate the fermenter.

Samples were taken at 4–5 hr intervals during the course of the fermentation to monitor carotenoid production as a function of the growth phase of the organism. The specific growth rate of the culture was 0.13 hr$^{-1}$. No adjustment of air or methane flows was employed to prevent the culture from becoming oxygen limited during the course of the fermentation. Furthermore, the aeration and methane addition continued once the culture had stopped growing to explore β-carotene production in the absence of cell growth. Cessation of growth was indicated when no changes in optical density were observed, by the disappearance of ammonia from the fermentation media, and by an observed decrease in the CER. The β-carotene content of the cells, dry cell weight, ammonia levels, and carbon dioxide evolution rate were determined as described supra. The results are stated in Table 15 below.

TABLE 15

Fed-Batch Fermentation Results of *Methylomonas sp.* 16a/pCRT1

| Time (hr) | OD 600 | DCW[a] (g L$^{-1}$) | β-carotene Titer (μg gDCW$^{-1}$) | β-Carotene Titer (mg L$^{-1}$) | Ammonia Conc. (mM) | CER[b] (mmol hr$^{-1}$) | pO$_2$[c] (% Sat'n) |
| --- | --- | --- | --- | --- | --- | --- | --- |
| 0.0 | 0.351 | ND[d] | ND[d] | ND[d] | 23.7 | ND[d] | ND[d] |
| 37.7 | 1.59 | 0.54 | 2640 | 1.42 | 17.8 | 8.1 | 53.65 |
| 41.6 | 2.50 | 0.87 | 6300 | 5.51 | 13.9 | 13.2 | 33.50 |
| 45.9 | 4.27 | 1.55 | 7710 | 11.94 | 8.7 | 22.1 | 1.00 |
| 49.3 | 7.99 | 2.36 | 5050 | 12.07 | 0.12 | 19.4 | 0.0 |
| 53.5 | 11.68 | 3.44 | 4510 | 15.51 | 0 | 10.4 | 45.50 |
| 58.9 | 13.63 | 4.07 | 3960 | 15.85 | 0 | 4.2 | 65.85 |
| 63.8 | 13.80 | 3.87 | 4150 | 15.96 | 0 | 4.2 | 72.70 |
| 69.6 | 13.45 | 3.93 | 4890 | 19.01 | 0 | 2.0 | 75.30 |

[a]DCW = [Dry Cell Weight]
[b]CER = [Carbon Dioxide Evolution Rate]
[c]pO2 = [Dissolved Oxygen Concentration in Fermenter]
[d]ND = [Not Determined]

At 46 hr into the fermentation β-carotene titers reached a maximum titer of 7,710 ppm on a dry weight basis. Shortly after this time the β-carotene titer dropped substantially as the fermenter became oxygen limited as noted by the dissolved oxygen concentration. Thus, it is apparent that maintenance of high β-carotene titers is dependent on high oxygen tensions present in the fermentation media. Presumably higher β-carotene titers could be reached than reported here through better control of the dissolved oxygen concentration during the course of the fermentation. Maximum β-carotene productivities were calculated as 620 μg gDCW$^{-1}$ hr$^{-1}$ and 886 μg L$^{-1}$ hr$^{-1}$. In addition, β-carotene concentrations were found to stabilize at roughly 4,400 ppm as the cells transitioned into stationary phase. It is apparent that β-carotene titers are growth associated as well as dependent on oxygen tension.

What is claimed is:

1. A method for the production of a carotenoid compound comprising:
   (a) providing a transformed methylotrophic host cell comprising:
      (i) isopentenyl pyrophosphate; and
      (ii) at least one isolated nucleic acid molecule encoding an enzyme in the carotenoid biosynthetic pathway under the control of suitable regulatory sequences;
   (b) contacting the host cell of step (a) under suitable growth conditions with an effective amount of a C1 carbon substrate, selected from the group consisting of methane and methanol whereby an carotenoid compound is produced.

2. A method according to claim 1 wherein the methylotrophic host cell is a methanotroph selected from the group consisting of *Methylomonas, Methylobacter, Methylococcus, Methylosinus, Methylocyctis, Methylomicrobium, Methanomonas,* and *Methylophilu.*

3. A method according to claim 2 wherein the methanotrophic host is a high growth methanotrophic strain which comprises a functional Embden-Meyerhof carbon pathway, said pathway comprising a gene encoding a pyrophosphate dependent phosphofructokinase enzyme.

4. A method according to claim 3 wherein the gene encoding a pyrophosphate dependent phosphofructokinase enzyme has the amino acid sequence as set forth in SEQ ID NO:2.

5. A method according to claim 3 wherein the high growth methanotrophic bacterial strain optionally contains a functional Entner-Douderoff carbon pathway.

6. A method according to claim 3 wherein the high growth methanotrophic strain is *methylomonas* 16a having the ATCC designation ATCC PTA 2402.

7. A method according to claim 1 wherein the isolated nucleic acid molecule encodes a carotenoid biosynthetic enzyme selected from the group consisting of geranylgeranyl pyrophosphate (GGPP) synthase, phytoene synthase, phytoene desaturase, lycopene cyclase, β-carotene hydroxylase, zeaxanthin glucosyl transferase, β-carotene ketolase, β-carotene C-4 oxygenase, β-carotene desaturase, spheroidene monooxygenase, carotene hydratase, carotenoid 3,4-desaturase, 1-OH-carotenoid methylase, farnesyl diphosphate synthetase, and diapophytoene dehydrogenase.

8. A method according to claim 7 wherein the geranylgeranyl pyrophosphate (GGPP) synthase as the amino acid sequence as set forth in SEQ ID NO:26.

9. A method according to claim 7 wherein the phytoene synthase as the amino acid sequence as set forth in SEQ ID NO:34.

10. A method according to claim 7 wherein the phytoene desaturase as the amino acid sequence as set forth in SEQ ID NO:32.

11. A method according to claim 7 wherein the lycopene cyclase as the amino acid sequence as set forth in SEQ ID NO:30.

12. A method according to claim 7 wherein β-carotene hydroxylase as the amino acid sequence as set forth in SEQ ID NO:36.

13. A method according to claim 7 wherein zeaxanthin glucosyl transferase as the amino acid sequence as set forth in SEQ ID NO:28.

14. A method according to claim 7 wherein the isolated nucleic acid molecule encoding a carotenoid biosynthetic enzyme encodes a β-carotene ketolase having the amino acid sequence as set for the in SEQ ID NO:38.

15. A method according to claim 7 wherein the isolated nucleic acid molecule encoding a carotenoid biosynthetic enzyme encodes a farnesyl diphosphate synthetase having the amino acid sequence as set forth in SEQ ID NO:20.

16. A method according to claim 7 wherein the isolated nucleic acid molecule encoding a carotenoid biosynthetic enzyme encodes a diapophytoene dehydrogenase enzyme having the amino acid sequence selected from the group consisting of SEQ ID NO:22 and SEQ ID NO:24.

17. A method according to claim 2 wherein said methanotroph is *methylomonas* 16a ATCC PTA 2402.

18. A method according to claim 1 wherein isopentenyl pyrophosphate is provided by the expression of heterologous upper pathway isoprenoid pathway genes.

19. A method according to claim 18 wherein said upper pathway isoprenoid genes are selected from the group consisting of D-1-deoxyxylulose-5-phosphate synthase (Dxs), D-1-deoxyxylulose-5-phosphate reductoisomerase (Dxr), 2C-methyl-d-erythritol cytidylyltransferase (IspD), 4-diphosphocytidyl-2-methylerthritol kinase (IspE), 2C-methyl-d-erythritol 2,4-cyclodiphosphate synthase (IspF), CTP synthase (PyrG), lytB, and GcpE.

20. A method according to claim 1 wherein the carotenoid compound is selected from the group consisting of antheraxanthin, adonixanthin, astaxanthin, canthaxanthin, capsorubrin, β-cryptoxanthin alpha-carotene, beta-carotene, epsilon-carotene, echinenone, gamma-carotene, zeta-carotene, alpha-cryptoxanthin, diatoxanthin, 7,8-didehydroastaxanthin, fucoxanthin, fucoxanthinol, isorenieratene, lactucaxanthin, lutein, lycopene, neoxanthin, neurosporene, hydroxyneurosporene, peridinin, phytoene, rhodopin, rhodopin glucoside, siphonaxanthin, spheroidene, spheroidenone, spirilloxanthin, uriolide, uriolide acetate, violaxanthin, zeaxanthin-β-diglucoside, and zeaxanthin.

21. A method for the over-production of carotenoid production in a transformed methylotrophic host comprising:
(a) providing a transformed methylotrophic host cell comprising:
(i) isopentenyl pyrophosphate; and
(ii) at least one isolated nucleic acid molecule encoding an enzyme in the carotenoid biosynthetic pathway under the control of suitable regulatory sequences; and
(iii) either:
1) multiple copies of at least one gene encoding an enzyme selected from the group consisting of D1-deoxyxylulose-5-phosphate synthase (Dxs), D-1-deoxyxylulose-5-phosphate reductoisomerase (Dxr), 2C-methyl-d-erythritol cytidylyltransferase (IspD), 4-diphosphocytidyl-2-C-methylerythritol kinase (IspE), 2C-methyl-d-erythritol 2,4-cyclodiphosphate synthase (IspF), CTP synthase (PyrG) lytB and gcpE; or
2) at least one gene encoding an enzyme selected from the group consisting of D-1-deoxyxylulose-5-phosphate synthase (Dxs), D-1-deoxyxylulose-5-phosphate reductoisomerase (Dxr), 2C-methyl-d-erythritol cytidylyltransferase (IspD), 4-diphosphocytidyl-2-C-methylerythritol kinase (IspE), 2C-methyl-d-erythritol 2,4-cyclodiphosphate synthase (IspF), CTP synthase (PyrG), lytB and gcpE operably linked to a strong promoter;
(b) contacting the host cell of step (a) under suitable growth conditions with an effective amount of a C1 carbon substrate, selected from the group consisting of methane and methanol whereby a carotenoid compound is over-produced.

22. A method according to claim 21 wherein the at least one gene encoding an enzyme of either part (a)(iii)(1) or (a)(iii)(2) encodes an enzyme selected from the group consisting of SEQ ID NO:6, 8, 10, 12, 14, 16, and 18.

* * * * *